US012637469B2

(12) United States Patent
Qian et al.

(10) Patent No.: US 12,637,469 B2
(45) Date of Patent: May 26, 2026

(54) 1H-PYRAZOLE DERIVATIVE AND APPLICATION THEREOF AS DUAL TARGET INHIBITOR OF SYK AND VEGFR2

(71) Applicant: Ocumension Therapeutics (Suzhou) Co., Ltd., Suzhou city (CN)

(72) Inventors: Wenyuan Qian, Shanghai (CN); Hongjian Wang, Shanghai (CN); Liang Tan, Shanghai (CN); Shuhui Chen, Shanghai (CN)

(73) Assignee: OCUMENSION THERAPEUTICS (SUZHOU) CO., LTD., Suzhou City (CN)

( * ) Notice: Subject to any disclaimer, the term of this patent is extended or adjusted under 35 U.S.C. 154(b) by 861 days.

(21) Appl. No.: 17/904,460

(22) PCT Filed: Feb. 23, 2021

(86) PCT No.: PCT/CN2021/077482

§ 371 (c)(1),
(2) Date: Aug. 17, 2022

(87) PCT Pub. No.: WO2021/169958

PCT Pub. Date: Sep. 2, 2021

(65) Prior Publication Data

US 2023/0219960 A1 Jul. 13, 2023

(30) Foreign Application Priority Data

Feb. 24, 2020 (WO) ................ PCT/CN2020/076414

(51) Int. Cl.
*C07D 487/04* (2006.01)
*A61P 27/02* (2006.01)

(52) U.S. Cl.
CPC ............ *C07D 487/04* (2013.01); *A61P 27/02* (2018.01)

(58) Field of Classification Search
CPC ........... A61P 11/00; A61P 11/06; A61P 13/12; A61P 19/02; A61P 27/02; A61P 27/14; A61P 35/00; C07D 487/04; C07D 519/00
See application file for complete search history.

(56) References Cited

U.S. PATENT DOCUMENTS

| | | | | |
|---|---|---|---|---|
| 8,729,082 | B2 | 5/2014 | Koppitz et al. | |
| 2012/0128662 | A1 | 5/2012 | Koppitz et al. | |
| 2021/0284646 | A1 | 9/2021 | Wang et al. | |
| 2024/0132503 | A1 * | 4/2024 | Qian | C07C 65/03 |

FOREIGN PATENT DOCUMENTS

| | | | |
|---|---|---|---|
| CN | 1609105 | | 4/2005 |
| CN | 102413831 | | 4/2012 |
| CN | 110194772 | | 9/2019 |
| CN | 112225742 | A | 1/2021 |
| CN | 114591338 | | 6/2022 |
| CN | 114621232 | | 6/2022 |
| WO | 2006/091246 | A1 | 8/2006 |
| WO | 2010/135571 | | 11/2010 |
| WO | 2022/166548 | A1 | 8/2022 |

OTHER PUBLICATIONS

Peng et. al., “VEGFR-2 inhibitors and the therapeutic applications thereof: a patent review (2012-2016)”, Expert Opinion on Therapeutic Patents (Year: 2017).*
Wong et. al., “Targeting Syk as a treatment for allergic and autoimmune disorders”, Expert Opin Investig Drug (Year: 2004).*
English Translation of the International Search Report (ISR) for PCT/CN2021/077482 dated May 21, 2021, 2 pages.
Peng, et al. (2017) “VEGFR-2 inhibitors and the therapeutic applications thereof: a patent review (2012-2016).” Expert Opinion on Therapeutic Patents, 27:9, 987-1004.
Wong, et al. (2004) “Targeting Syk as a treatment for allergic and autoimmune disorders.” Expert Opin Investig Drug, 13(7):743-762.

* cited by examiner

*Primary Examiner* — Jeffrey H Murray
*Assistant Examiner* — Daniel John Burkett
(74) *Attorney, Agent, or Firm* — McDonnell Boehnen Hulbert & Berghoff, LLP

(57) ABSTRACT

The present disclosure relates to a class of spleen tyrosine kinase (Syk) and vascular endothelial growth factor receptor 2 (VEGFR2) dual inhibitors. Specifically, it discloses a compound represented by formula (I) or a pharmaceutically acceptable salt thereof, a method for preparing the compound, a method of inhibiting spleen tyrosine kinase (Syk) and vascular endothelial growth factor 2 in a subject, and a method of treating allergic, autoimmune and inflammatory diseases. The compound exhibits good Syk and VEGFR2 dual inhibitory activity as well as excellent targeting specificity, with no off-target selectivity issues. Additionally, the compound of the present disclosure has a high eye-to-blood ratio and is suitable for ocular administration.

40 Claims, 1 Drawing Sheet

1H-PYRAZOLE DERIVATIVE AND APPLICATION THEREOF AS DUAL TARGET INHIBITOR OF SYK AND VEGFR2

The invention claims the priority of: PCT/CN2020/076414, filed on Feb. 24, 2020.

TECHNICAL FIELD

The invention relates to a dual-target inhibitor of spleen tyrosine kinase (Syk) and vascular endothelial growth factor 2 (VEGFR2), in particular to a compound represented by formula (I) or a pharmaceutically acceptable salt thereof, and use thereof in the preparation of spleen tyrosine kinase (Syk) and vascular endothelial growth factor 2 (VEGFR2) dual inhibitor related pharmaceuticals.

BACKGROUND

Protein kinases (the largest family of human kinases) include more than 500 proteins. Spleen tyrosine kinase (Syk) is a member of the Syk family of tyrosine kinases and is a regulator of early B-cell development as well as mature B-cell activation, signal transduction and survival.

Syk is a non-receptor tyrosine kinase that plays an important role in immune receptor-mediated and integrin-mediated signal transduction in a variety of cell types, including B cells, macrophages, monocytes, mast cells, eosinophils, basophils, neutrophils, dendritic cells, T cells, natural killer cells, platelets and osteoclasts. The immunoreceptors described in this application include typical immunoreceptors and immunoreceptor-like molecules. Typical immune receptors include B-cell and T-cell antigen receptors and various immunoglobulin receptors (Fc receptors). Immune receptor-like molecules are structurally related to immune receptors or participate in similar signal transduction pathways, and they are mainly involved in non-adaptive immune functions (including neutrophil activation, natural killer cells recognition and osteoclast activity). Integrins are cell surface receptors that play key roles in the activation of both leukocyte adhesion and innate and acquired immunity.

Ligand binding results in the activation of both immunoreceptors and integrins, which lead to activation of Src family kinases, and immunoreceptor tyrosine activation motifs (ITAMs) in the cytoplasmic surface of receptor-associated transmembrane aptamers result in activation of Syk and subsequent phosphorylation and activation of downstream signal transduction pathways.

Syk is critical for B-cell activation via B-cell receptor (BCR) signal transduction. Once Syk binds to phosphorylated BCR, BCR is activated, thus causing early signal transduction events following BCR activation. B-cell signal transduction through BCR can lead to a wide range of biological exports, which in turn are dependent on the developmental stage of the B-cells. The strength and duration of the BCR signals must be precisely adjusted. Aberrant BCR-mediated signal transduction can result in dysregulated B-cell activation and/or the formation of pathogenic autoantibodies, leading to various autoimmune and/or inflammatory diseases. Mice lacking Syk exhibited impaired B-cell maturation, reduced immunoglobulin production, compromised T-cell-independent immune responses, and a significant reduction in sustained calcium signal transduction to BCR stimulation.

Substantial evidence supports the role of B-cells and the human immune system in the pathogenesis of autoimmune and/or inflammatory diseases. Protein-based therapies such as Rituxan, which have been developed to reduce B-cells, represent a way to treat a variety of autoimmune and inflammatory diseases. Autoantibodies and their resulting immune complexes are known to play a pathogenic role in autoimmune and/or inflammatory diseases. Pathogenic responses to these antibodies depend on the signal transduction through Fc receptors, which in turn depends on Syk. Due to the role of Syk in B-cell activation and FcR-dependent signal transduction, inhibitors of Syk can be used as inhibitors of B-cell mediated pathogenic activities including autoantibody production. Therefore, inhibition of Syk enzyme activity in cells is proposed to treat autoimmune diseases through its effect on autoantibody production.

Syk also plays an important role in FCεRI-mediated mast cell degranulation and eosinophil activation. Therefore, Syk is involved in allergic diseases (including asthma).

Syk binds to the phosphorylated y chain of FCεRI (through its SH2 domain) and is critical for downstream signal transduction. Syk-deficient mast cells show lack of degranulation, arachidonic acid and cytokine secretion. This also indicates a pharmacological agent that inhibits Syk activity in mast cells. Treatment with Syk antisense oligonucleotides inhibited antigen-induced infiltration of eosinophils and neutrophils in an animal model of asthma. Syk-deficient eosinophils also showed impaired activation in response to FCεRI stimulation. Therefore, small molecule inhibitors of Syk would be useful in the treatment of allergy-induced inflammatory diseases, including asthma.

Syk is also expressed in mast cells and monocytes and has been shown to be important for the functions of these cells. For example, Syk deficiency in mice is associated with impaired IgE-mediated mast cell activity, which is a significant reduction in the release of TNF-α and other inflammatory cytokines. Syk kinase inhibitors have also been shown to inhibit mast cell degranulation in cellular tests.

VEGFR2, also known as KDR or Flk-1, is identified as a receptor for VEGF and VEGFC, is an early marker of endothelial cell progenitors, and its expression is restricted to endothelial cells in vivo. VEGFR2 has been shown to be a major signal transducer in the development of angiogenesis and pathological conditions such as cancer and diabetic retinopathy. Studies have shown that anti-VEGF can inhibit the expression and activation of pro-inflammatory factors, thereby reducing ocular surface inflammation.

VEGFR2 transduces major signals of angiogenesis through its potent tyrosine kinase activity. However, unlike other representative tyrosine kinase receptors, VEGFR2 does not use the Ras pathway as the primary downstream signal transduction, but rather the phospholipase C protein kinase C pathway to express mitogen-activated protein (MAP) kinase activation and DNA synthesis. Therefore, inhibition of VEGFR2 activity and its downstream signal transduction is an important target for the treatment of diseases involving angiogenesis and inflammation.

In diseases such as tumors, angiogenesis is an important step in the development of a disease. If angiogenesis can be inhibited, (Folkman. 2002, Role of angiogenesis in tumor growth and metastasis, Semin Oncol. 29(6 Suppl 16):15-8; Witmer et al. 2003, Vascular endothelial growth factors and angiogenesis in eye disease, Prog Retin Eye Res. 22:1-29. Vascular endothelial growth factor is a secreted angiogenic mitogen, Science, 246: 1306-1309; vascular endothelial growth factor is a key factor in inducing angiogenesis. Ferrara et al., 2003, The biological properties of VEGF and its receptors, Nature Medicine 9: 9-22). The VEGFR2 protein molecule consists of three parts: extracellular region, transmembrane region and cytoplasmic region. VEGF can bind to the extracellular region of VEGFR2, and the binding can induce the phosphorylation of the tyrosine kinase group in the cytoplasmic region of VEGFR2, thereby initiating intracellular signal transmission, causing the proliferation, and migration of vascular endothelial cells and angiogenesis, and preventing the correction of vascular endothelial cells. Aiming at the key role of VEGFR2 in the process of promoting angiogenesis signal transmission, the combination of VEGF and VEGF2 is inhibited to achieve the effect of preventing angiogenesis and inhibiting inflammation. Abnormal angiogenesis is related to the pathology of many diseases, including cancer, age-related macular degeneration (AMD), proliferative diabetic retinopathy (PDR), and ocular surface inflammation (DED). Thrombospondin-1 (TSP-1) regulates VEGFR-2 signal transduction through CD36 in microvascular endothelial cells, and VEGF-A initiates angiogenesis by binding to VEGFR-2 and inducing its autophosphorylation, and promotes Syk phosphorylation. Activation of Syk in turn further phosphorylates residue y1175 of VEGFR-2 and mediates endothelial cell migration, and in the absence of VEGF-A, the TSP-1-CD36 complex promotes Fyn activation, thereby switching off angiogenesis.

Thus, the inhibition of Syk and VEGFR-2 activities is useful in the treatment of allergic, autoimmune and inflammatory diseases, including but not limited to dry eye and allergic conjunctivitis, retinal inflammatory diseases, age-related macular degeneration (AMD), proliferative diabetic retinopathy (PDR) and retinopathy of prematurity (ROP), cancer, rheumatoid arthritis, glomerulonephritis, multiple vasculitides, idiopathic thrombocytopenia purpura (ITP), myasthenia gravis, allergic rhinitis, chronic obstructive pulmonary disease (COPD), adult respiratory distress syndrome (ARDs) and asthma.

SUMMARY

The invention provides a compound represented by formula (I) or a pharmaceutically acceptable salt thereof, (I)

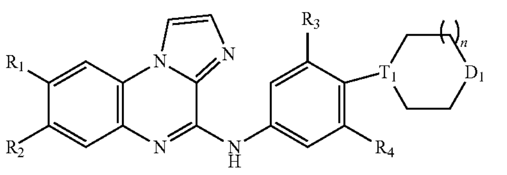

wherein,

- $R_1$ and $R_2$ are each independently selected from H and pyrazolyl, and $R_1$ and $R_2$ are not both pyrazolyl or H;
- $R_3$ and $R_4$ are each independently selected from H, F, Cl, Br, I, OH, $NH_2$, CN, $C_{1-3}$ alkyl and $C_{1-3}$ alkoxy, the $C_{1-3}$ alkyl and $C_{1-3}$ alkoxy are optionally substituted with 1, 2 or 3 halogens;
- $T_1$ is selected from CH and N;
- $D_1$ is selected from —O—, —$C(R_5)(R_6)$—, —$N(R_7)$— and

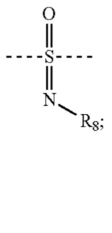

- $R_5$ and $R_6$ are each independently selected from H, F, C, Br, I, OH and $C_{1-3}$ alkyl, and the $C_{1-3}$ alkyl is optionally substituted with 1, 2 or 3 halogens;
- alternatively, $R_5$ and $R_6$ together with the carbon atom to which they are both connected form an oxetanyl group;
- $R_7$ is selected from H,

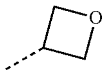

and $C_{1-3}$ alkyl, and the $C_{1-3}$ alkyl is optionally substituted with 1, 2 or 3 halogens;
- $R_8$ is selected from H and —C(=O)—$C_{1-3}$ alkyl;
- n is selected from 1 and 2.

In some embodiments of the invention, the above $R_1$ is selected from H,

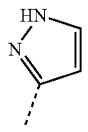

and

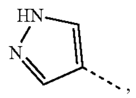

and other variables are defined in the invention.

In some embodiments of the invention, the above $R_2$ is selected from H,

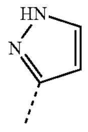

and

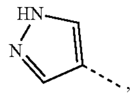

and other variables are defined in the invention.

In some embodiments of the invention, the above $R_3$ is selected from H, F, Cl, Br, I, OH, $NH_2$, CN, $CH_3$ and $CH_3O$, and other variables are defined in the invention.

In some embodiments of the invention, the above $R_4$ is selected from H, F, Cl, Br, I, OH, $NH_2$, CN, $CH_3$ and $CH_3O$, and other variables are defined in the invention.

In some embodiments of the invention, the above $R_5$ is selected from H, F, Cl, Br, I, OH, $NH_2$ and $CH_3$, and other variables are defined in the invention.

In some embodiments of the invention, the above $R_5$ is selected from H, F, Cl, Br, I, OH and $CH_3$, and other variables are defined in the invention.

In some embodiments of the invention, the above $R_5$ is selected from H, F, Cl, Br, I, OH, $NH_2$ and $CH_3$, and other variables are defined in the invention.

In some embodiments of the invention, the above $R_6$ is selected from H, F, Cl, Br, I, OH and $CH_3$, and other variables are defined in the invention.

In some embodiments of the invention, the above $R_5$ and $R_6$ together with the carbon atom to which they are both connected form

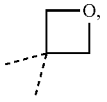

and other variables are defined in the invention.

In some embodiments of the invention, the above $R_7$ is selected from H, $CH_3$ and

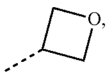

and other variables are defined in the invention.

In some embodiments of the invention, the above $R_8$ is selected from H and —C(=O)—$CH_3$, and other variables are defined in the invention.

In some embodiments of the invention, the above

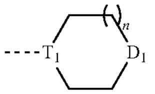

is selected from

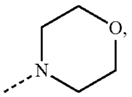 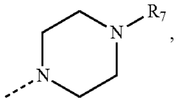 , 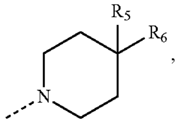 ,

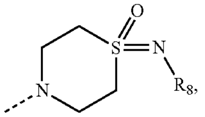 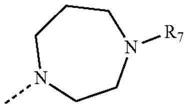 and

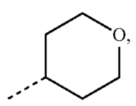

wherein $R_5$, $R_6$, $R_7$ and $R_8$ are defined in the invention, and other variables are defined in the invention.

In some embodiments of the invention, the above

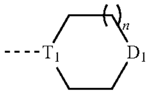

is selected from

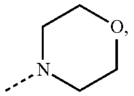 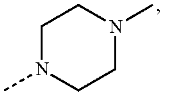 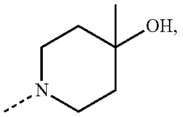

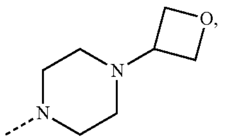 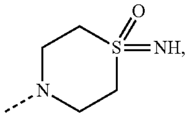

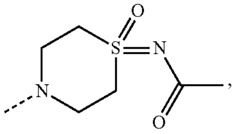 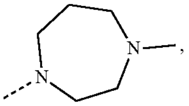

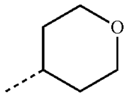 and 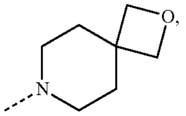

and other variables are defined in the invention.

Further embodiments of the invention are obtained by any combination of the above variables.

In some embodiments of the invention, the above compound or a pharmaceutically acceptable salt thereof is selected from (I-1)

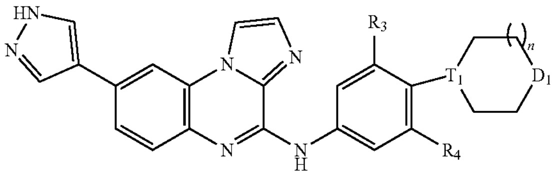

(I-2)

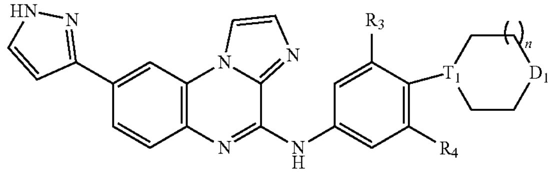

(I-3)

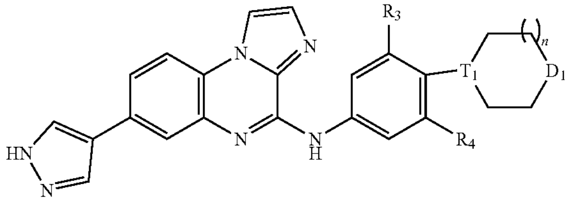

(I-4)

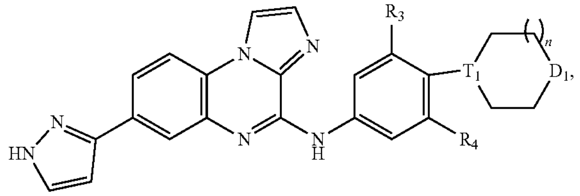

wherein, $R_3$, $R_4$, $T_1$, $D_1$ and n are defined in the invention.

The invention also provides a compound represented by any of the following formula or a pharmaceutically acceptable salt thereof,

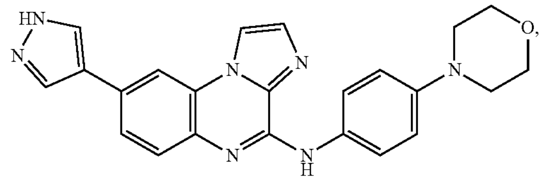

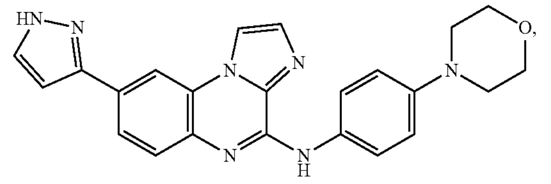

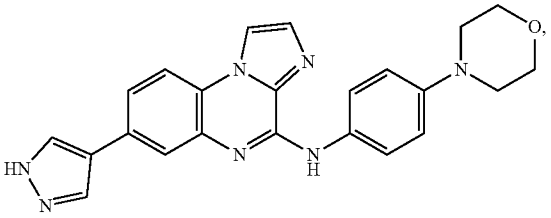

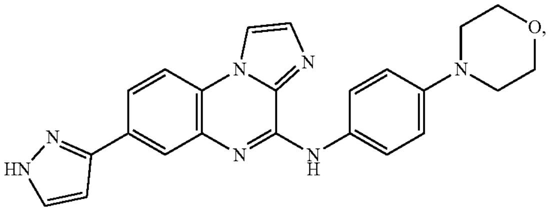

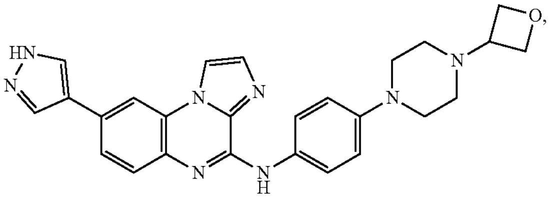

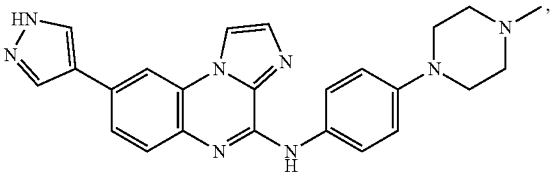

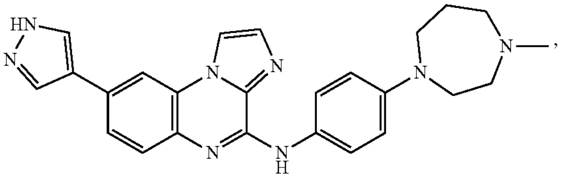

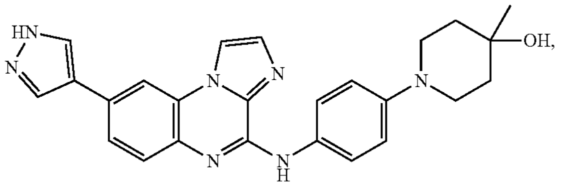

-continued

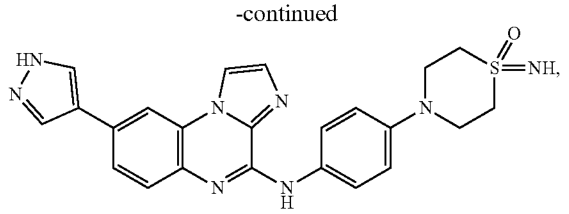

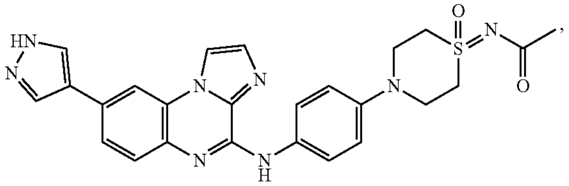

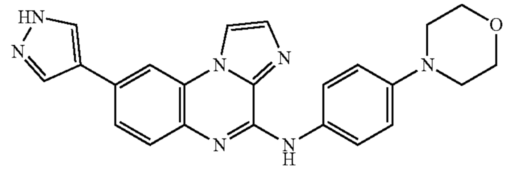

and

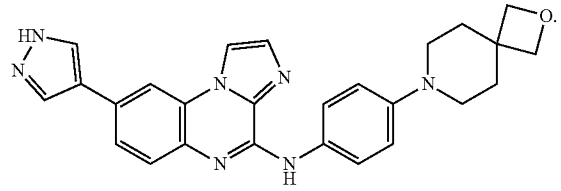

The invention further provides the use of the above compound, or a pharmaceutically acceptable salt thereof, in the preparation of a spleen tyrosine kinase (Syk) and vascular endothelial growth factor 2 (VEGFR2) dual inhibitor related pharmaceutical.

In some embodiments of the invention, the above use is characterized in that the spleen tyrosine kinase (Syk) and vascular endothelial growth factor 2 (VEGFR2) dual inhibitor related pharmaceutical is used for the treatment of allergic, autoimmune and inflammatory diseases such as dry eye and allergic conjunctivitis, retinal inflammatory diseases, age-related macular degeneration (AMD), proliferative diabetic retinopathy (PDR) and retinopathy of prematurity (ROP), cancer, rheumatoid arthritis, glomerulonephritis, multiple vasculitides, idiopathic thrombocytopenic purpura (ITP), myasthenia gravis, allergic rhinitis, chronic obstructive pulmonary disease (COPD), adult respiratory distress syndrome (ARDs) and asthma.

Technical Effect

The compound of the invention, as a kind of spleen tyrosine kinase (Syk) and vascular endothelial growth factor 2 (VEGFR2) dual inhibitor, exhibits good dual inhibitory activity of Syk and VEGFR2, exhibits very good targeting specificity, without off-target selectivity issues, has no significant inhibitory effect on the five main subtypes of CYP450 enzymes (CYP1A2, 2C9, 2C19, 2D6, 3A4), and demonstrates a pharmaceutical effect with statistical significance in the scopolamine-induced mouse dry eye model. Moreover, the compound of the invention has a high eye-to-blood ratio, is suitable for ocular administration, and has a great development prospect.

Definition and Explanation

Unless otherwise specified, the following terms and phrases used herein are intended to have the following meanings. A particular term or phrase should not be considered indeterminate or unclear without specific definitions, but should be understood in its ordinary meaning. When a trade name appears herein, it is intended to refer to its corresponding commercial product or its active ingredient.

As used herein, the term "pharmaceutically acceptable" refers to those compounds, materials, compositions and/or dosage forms that, within the scope of sound medical judgment, are suitable for use in contact with human and animal tissues, without excessive toxicity, irritation, allergic reactions or other problems or complications, commensurate with a reasonable benefit-risk ratio.

The term "pharmaceutically acceptable salts" refers to salts of the compounds of the invention, prepared from compounds with specific substituents discovered by the invention and relatively non-toxic acids or bases. When the compounds of the invention contain relatively acidic functional groups, base addition salts can be obtained by contacting such compounds with a sufficient amount of base in a pure solution or in a suitable inert solvent. Pharmaceutically acceptable base addition salts include sodium, potassium, calcium, ammonium, organic amine or magnesium salts or the like. When the compounds of the invention contain relatively basic functional groups, acid addition salts can be obtained by contacting such compounds with a sufficient amount of acid in a pure solution or in a suitable inert solvent. Examples of pharmaceutically acceptable acid addition salts include inorganic acid salts, and the inorganic acids include, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, etc.; and organic acid salts, and the organic acids include, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, methanesulfonic acid and the like; and also salts of amino acids such as arginine, and salts of organic acids such as glucuronic acid. Certain specific compounds of the invention contain both basic and acidic functional groups and thus can be converted into either base or acid addition salts.

The pharmaceutically acceptable salts of the invention can be synthesized from the acid or base group-containing parent compounds by conventional chemical methods. Generally, such salts are prepared by reacting the free acid or base form of these compounds with a stoichiometric amount of the appropriate base or acid in water or an organic solvent or a mixture of the two.

The compounds of the invention may have particular geometric or stereoisomeric forms. The invention contemplates all such compounds, including cis and trans isomers, (−)- and (+)-enantiomers, (R)- and (S)-enantiomers, diastereoisomers, (D)-isomers, (L)-isomers, racemic mixtures thereof and other mixtures, such as enantiomer or diastereoisomer-riched mixtures, all of the mixtures are within the scope of the invention. Additional asymmetric carbon atoms may be present in substituents such as alkyl. All these isomers, as well as mixtures thereof, are included within the scope of the invention.

Unless otherwise specified, the term "enantiomers" or "optical isomers" refers to stereoisomers that are mirror images of each other.

Unless otherwise specified, the term "cis-trans isomers" or "geometric isomers" refers to those in which a double bond or a single bond of a ring-forming carbon atom is unable to rotate freely.

Unless otherwise specified, the term "diastereoisomers" refers to stereoisomers having two or more chiral centers in the molecule, and the molecules are in a non-mirror-image relationship.

Unless otherwise specified, "(+)" means dextrorotatory, "(−)" means levorotatory, and "(±)" means racemic.

Unless otherwise specified, the absolute configuration of a stereocenter is represented by solid wedge bonds ((  )) and dashed wedge bonds ((  )), and the relative configuration of a stereocenter is represented by solid straight bonds ((  )) and dashed straight bonds ((  )), or a wavy line ((  )) is used to represent a solid wedge bond ((  )) or a dashed wedge bond ((  )), or a wavy line ((  )) is used to represent a solid straight bond ((  )) or a dashed straight bond ((  )).

Unless otherwise specified, the term "enriched in one isomer", "isomer-riched", "enriched in one enantiomer" or "enantiomer-riched" refers to one of the isomers or enantiomers has a content of less than 100%, and the isomer or enantiomer content is greater than or equal to 60%, or greater than or equal to 70%, or greater than or equal to 80%, or greater than or equal to 90%, or greater than or equal to 95%, or greater than or equal to 96%, or greater than or equal to 97%, or greater than or equal to 98%, or greater than or equal to 99%, or greater than or equal to 99.5%, or greater than or equal to 99.6%, or greater than or equal to 99.7%, or greater than or equal to 99.8%, or greater than or equal to 99.9%.

Unless otherwise specified, the term "isomeric excess" or "enantiomeric excess" refers to the difference between the relative percentages of two isomers or two enantiomers. For example, if the content of one isomer or enantiomer is 90% and the content of the other isomer or enantiomer is 10%, then the isomeric or enantiomeric excess (i.e. an ee value) is 80%.

Optically active (R)- and (S)-isomers, as well as D- and L- isomers, can be prepared by chiral synthesis or chiral reagents or other conventional techniques. If one enantiomer of a certain compound of the invention is desired, it can be prepared by asymmetric synthesis or derivatization with a chiral auxiliary, wherein the resulting mixture of diastereoisomers is separated and the auxiliary group is cleaved to provide the desired pure enantiomer. Alternatively, when the molecule contains a basic functional group (such as an amino group) or an acidic functional group (such as a carboxyl group), salts of the diastereoisomers are formed with an appropriate optically active acid or base, and then the diastereoisomers are separated through conventional methods known in the art and then the pure enantiomers are recovered. In addition, the separation of enantiomers and diastereoisomers is usually accomplished by chromatography using a chiral stationary phase, optionally in combination with chemical derivatization (e.g., generating carbamates from amines). The compound of the invention may contain unnatural proportion(s) of atomic isotope(s) at one or more of the atoms that constitute the compound. For example, the compound can be labeled with a radioactive isotope, such as tritium ($^{3}H$), iodine-125 ($^{125}I$) or C-14 ($^{14}C$). For another example, a deuterated pharmaceutical can be formed by replacing hydrogen with deuterium, and the bond between deuterium and carbon is stronger than that between ordinary hydrogen and carbon. Compared with non-deuterated pharmaceuticals, deuterated pharmaceuticals have advantages such as reduced toxic side effects, increased drug stability, enhanced efficacy, and a prolonged pharmaceutical biological half-life. All transformations of the isotopic composition of the compounds of the invention, whether radioactive or not, are included within the scope of the invention.

The term "substituted" means that any one or more hydrogen atoms on a specified atom is replaced by a substituent, which may include deuterium and hydrogen variants, as long as the valence of the specified atom is normal and the substituted compound is stable. When the substituent is oxygen (i.e., =O), it means that two hydrogen atoms are substituted. Oxygen substitution does not occur on aromatic groups. The term "optionally substituted" means that the group may or may not be substituted, and unless otherwise specified, the type and number of the substituents may be arbitrary on a chemically achievable basis.

When any variable (such as R) occurs more than once in the composition or structure of a compound, its definition in each case is independent. Thus, for example, if a group is substituted with 0-2 Rs, the group may optionally be substituted with up to two Rs, with independent options for R in each case. Furthermore, combinations of substituents and/or variants thereof are allowable only if such combinations result in stable compounds.

When the number of a linking group is 0, such as $-(CRR)_0-$, it means that the linking group is a single bond.

When the number of a substituent is 0, it means that the substituent does not exist, for example $-A-(R)_0$ means that the structure is actually -A.

When a substituent is vacant, it means that the substituent does not exist. For example, when X in A-X is vacant, it means that the structure is actually A.

When one of the variables is selected as a single bond, it means that the two groups connected to it are directly connected, for example, when L in A-L-Z represents a single bond, it means that the structure is actually A-Z.

When the bond of a substituent can be cross-linked to two or more atoms on a ring, such a substituent can be bonded to any atom on the ring, for example, a structural unit

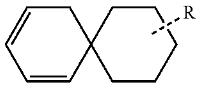 or 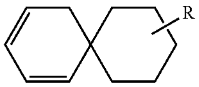

unit means that the cyclohexyl group or cyclohexadiene can be substituted by the substituent R at any position. When it is not specified through which atom the listed substituent is connected to the substituted group, such substituent may be connected through any of its atoms, for example, pyridyl as a substituent may be connected to a substituted group through any one of the carbon atoms on the pyridine ring.

When the linking direction of the listed linking group is not specified, the linking direction is arbitrary, for example, the linking group L in

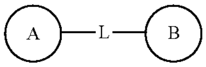

is -M-W—, herein -M-W— can be connected with ring A and ring B in a direction same as the reading direction from left to right to form

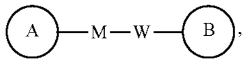, or -M-W— can be connected with ring A and ring B in a direction opposite to the reading direction from left to right to form

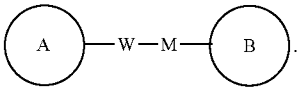.

Combinations of the linking groups, substituents and/or variants thereof are allowable only if such combinations result in stable compounds.

Unless otherwise specified, when a group has one or more linkable sites, any one or more of the sites in the group can be connected to another group(s) by a chemical bond(s). When the linking mode of the chemical bond involves unfixed locations, and there is a H atom(s) at the linkable site, when the chemical bond is linked, the number of the H atom(s) at the site will be correspondingly reduced in accordance with the number of the linked chemical bond(s) so that the resulting group has a corresponding valence. The chemical bond connecting the site to another group can be represented by a straight solid bond (), a straight dashed bond (), or a wavy line (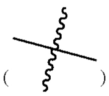).

For example, the straight solid bond in $-OCH_3$ indicates that the group is connected to another group through the oxygen atom in the group; the straight dashed bond in the group

indicates that the group is connected to other groups through the two ends of the nitrogen atom in the group; the wavy line in

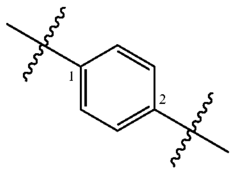 [SMILES: *c1ccc(*)cc1]

indicates that the 1 and 2 carbon atoms in the phenyl group are connected to other groups;

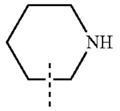

indicates that any linkable site on the piperidinyl group can be connected to another group through a chemical bond, including at least four connecting modes,

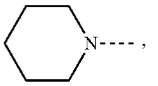 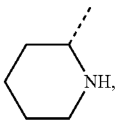 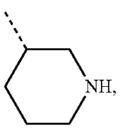 and 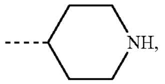

and even though a H atom is drawn on —N—, the connecting modes of

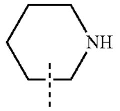

include the group

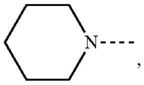

except that when a chemical bond is linked, the number of H at the site will be correspondingly reduced by 1 and the group becomes the corresponding monovalent piperidinyl group.

Unless otherwise specified, the term "halogen" by itself or as a part of another substituent means a fluorine, chlorine, bromine or iodine atom.

Unless otherwise specified, the term "$C_{1-3}$ alkyl" is used to denote a straight or branched chain saturated hydrocarbon group consisting of 1 to 3 carbon atoms. The $C_{1-3}$ alkyl group includes $C_{1-2}$ and $C_{2-3}$ alkyl groups and the like; it can be monovalent (e.g. methyl), divalent (e.g. methylene) or polyvalent (e.g. methine). Examples of $C_{1-3}$ alkyl groups include, but are not limited to, methyl (Me), ethyl (Et), propyl (including n-propyl and isopropyl), and the like.

Unless otherwise specified, the term "$C_{1-3}$ alkoxy" refers to those alkyl groups containing 1 to 3 carbon atoms attached to the remainder of the molecule through an oxygen atom. The $C_{1-3}$ alkoxy groups include $C_{1-2}$, $C_{2-3}$, $C_3$ and $C_2$ alkoxy groups and the like. Examples of $C_{1-3}$ alkoxy groups include, but are not limited to, methoxy, ethoxy, propoxy (including n-propoxy and isopropoxy), and the like.

Unless otherwise specified, $C_{n-n+m}$ or $C_n$-$C_{n+m}$ includes any specific case of n to n+m carbons, for example $C_{1-12}$ includes $C_1$, $C_2$, $C_3$, $C_4$, $C_5$, $C_6$, $C_7$, $C_8$, $C_9$, $C_{10}$, $C_{11}$, and $C_{12}$, and also includes any one of the ranges from n to n+m, for example, $C_{1-12}$ includes $C_{1-3}$, $C_{1-6}$, $C_{1-9}$, $C_{3-6}$, $C_{3-9}$, $C_{3-12}$, $C_{6-9}$, $C_{6-12}$, and $C_{9-12}$, etc.; similarly, an n- to n+m-membered ring means that the number of atoms in the ring is from n to n+m, for example, a 3- to 12-membered ring includes a 3-membered ring, 4-membered ring, 5-membered ring, 6-membered ring, 7-membered ring, 8-membered ring, 9-membered ring, 10-membered ring, 11-membered ring, and 12-membered ring, and also includes any one of the ranges from n to n+m, for example, a 3- to 12-membered ring includes a 3- to 6-membered ring, 3- to 9-membered ring, 5- to 6-membered ring, 5- to 7-membered ring, 6- to 7-membered ring, 6- to 8-membered ring, and 6- to 10-membered ring.

Unless otherwise specified, when a compound has a double bond structure, such as a carbon-carbon double bond, a carbon-nitrogen double bond or a nitrogen-nitrogen double bond, and each atom on the double bond is connected to two different substituents (for a double bond including a nitrogen atom(s), the lone pair of electrons on the nitrogen atom is regarded as a connected substituent), if the atom on the double bond in the compound and its substituents are represented by

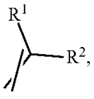

it represents the (Z)-isomer, (E)-isomer of the compound or a mixture of both isomers.

The compounds of the invention can be prepared by a variety of synthetic methods well known to those skilled in the art, including the specific embodiments set forth below, embodiments obtained by combining the above embodiments with other chemical synthesis methods, and alternative equivalent methods well known to those skilled in the art, preferred embodiments include, but are not limited to, the embodiments of the invention.

The structure of the compound of the invention can be confirmed by conventional methods well known to those skilled in the art. If the invention relates to the absolute configuration of the compound, the absolute configuration can be confirmed by conventional technical means in the art. For example, for single crystal X-ray diffraction (SXRD), the cultured single crystal is collected by Bruker D8 venture diffractometer, using a light source of CuKα radiation and a scanning mode of (p/w scanning, and after collecting relevant data, the crystal structure is further analyzed using a direct method (Shelxs97) to confirm the absolute configuration.

The solvents used in the invention are commercially available.

The following acronyms are used in the invention: Syk for tyrosine kinase; VEGFR2 for vascular endothelial growth factor receptor 2; VEGF for vascular endothelial growth factor; CD36 for thrombospondin receptor; DTT for 1,4-dithiothreitol; ATP for adenosine 5'-triphosphate; $MgCl_2$ for magnesium dichloride; $MnCl_2$ for manganese dichloride; EDTA for ethylenediaminetetraacetic acid; HEPES Buffer for 4-hydroxyethylpiperazine ethanesulfonic acid buffer; HTRF for high-throughput screening; DMSO for dimethyl sulfoxide; DIEA for N,N-diisopropylethylamine; CDI for N,N-carbonyldiimidazole; Pd(dppf)$Cl_2$ for 1,1-bisdiphenylphosphine ferrocene palladium dichloride; NaOH for sodium hydroxide; psi for pressure units; KOH for potassium hydroxide; BOC for tert-butoxycarbonyl which is an amine protecting group; HLM for human liver microsomes; NADPH for reduced nicotinamide adenine dinucleotide phosphate; SEM for 2-(trimethylsilyl)ethoxymethyl; and room temperature for a temperature of 15-30 degrees Celsius.

The compounds are named according to conventional nomenclature in the art or using ChemDraw® software, and the supplier catalog names are used for the commercially available compounds.

DETAILED DESCRIPTION

Figure 1:
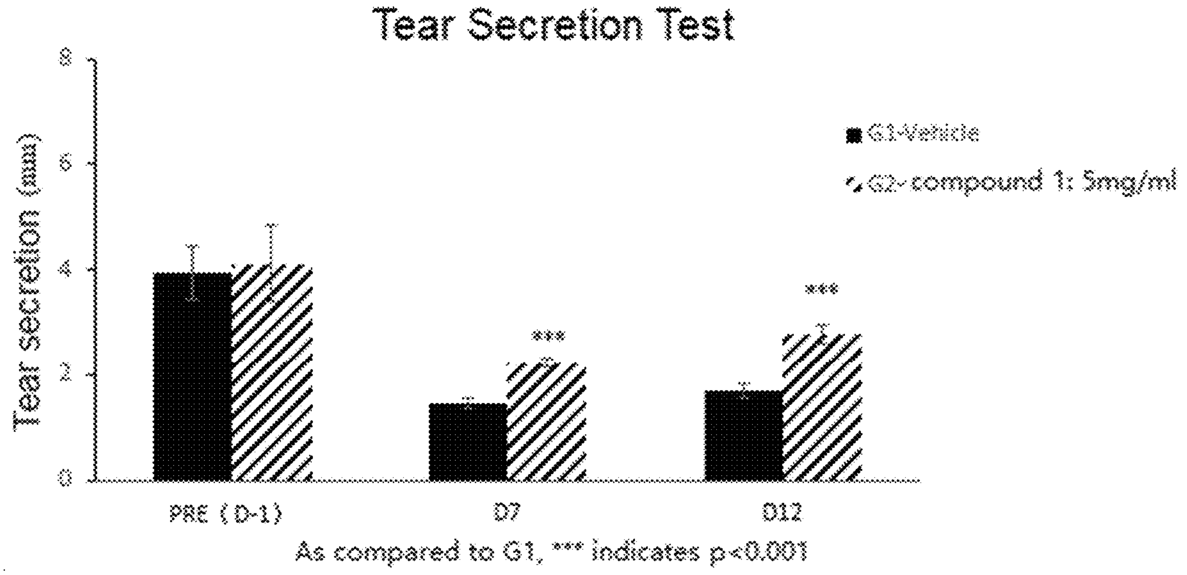
FIG. 1 shows the amounts of tear secretion on the 7th and 12th days after modeling. Note: PRE (D-1) means the day before modeling, D7 means the 7th day, D12 means the 12th day; p means significant difference.

The invention will be described in detail by the following examples which do not adversely limit the invention in anyway. The invention has been described in detail herein, and specific embodiments thereof have also been disclosed. Various changes and modifications, which are made to the specific embodiments of the invention without departing from the spirit and scope of the invention, are apparent to those skilled in the art.

Example 1: Preparation of Compound 1

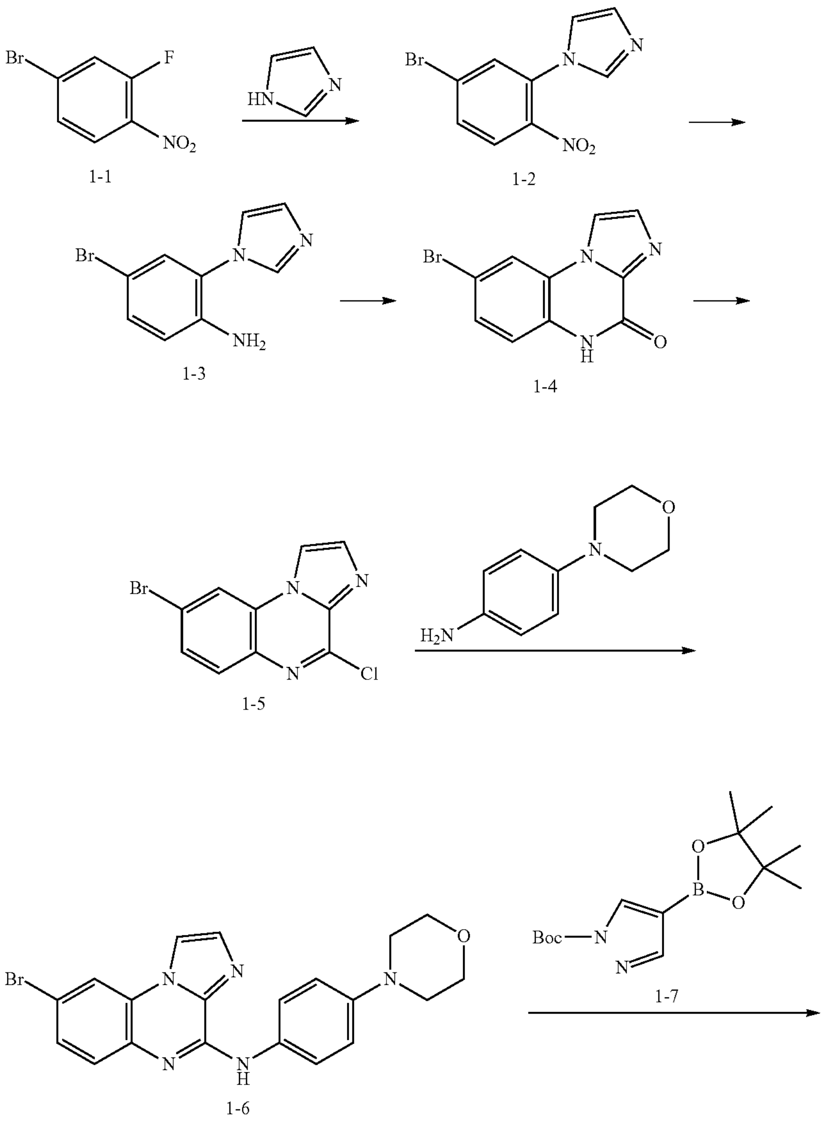

1-1 1-2 1-3 1-4 1-5 1-6 1-7

-continued

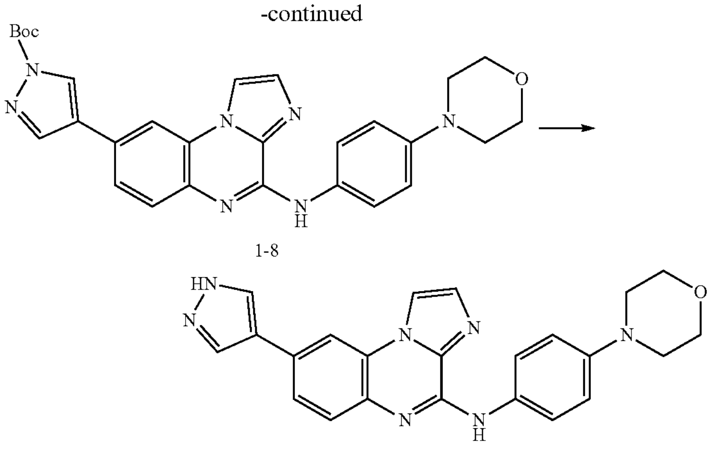

1-8

1

Step 1: Synthesis of Compound 1-2

Imidazole (1.55 g, 22.73 mmol), and DIEA (2.94 g, 22.73 mmol) were added to a solution of 4-bromo-2-fluoro-1-nitrobenzene (5 g, 22.73 mmol) in acetonitrile (100 mL). The reaction solution was stirred at 90° C. for 16 hours. The reaction solution was concentrated, water (100 mL) was added, and the mixture was extracted twice with ethyl acetate (50 mL). The organic phases were combined, dried, filtered and concentrated to obtain compound 1-2.

$^1$H NMR (400 MHz, DMSO-$d_6$) δ=7.79 (s, 1H), 7.34 (s, 1H), 7.30 (dd, J=2.4, 8.7 Hz, 1H), 7.24 (d, J=2.3 Hz, 1H), 7.11 (s, 1H), 6.83 (d, J=8.5 Hz, 1H), 5.18 (s, 2H).

Step 2: Synthesis of Compound 1-3

Stannous chloride dihydrate (20.2 g, 89.52 mmol) was added to a solution of compound 1-2 (4.00 g, 14.92 mmol) in ethanol (240 mL). The reaction solution was stirred at 90° C. for 3 hours. The reaction solution was concentrated under reduced pressure, ethyl acetate (300 mL) was added, the solution was neutralized with saturated sodium bicarbonate solution to pH=9, and a white solid was precipitated. The precipitated solid was filtered off. The filtrate was added with water (100 mL) and extracted twice with ethyl acetate (100 mL). The organic phases were combined, washed with saturated brine (200 mL), dried over anhydrous sodium sulfate, filtered and concentrated to obtain compound 1-3.

$^1$H NMR (400 MHz, DMSO-$d_6$) δ=7.79 (s, 1H), 7.34 (s, 1H), 7.30 (dd, J=2.4, 8.7 Hz, 1H), 7.24 (d, J=2.3 Hz, 1H), 7.11 (s, 1H), 6.83 (d, J=8.5 Hz, 1H), 5.18 (s, 2H).

Step 3: Synthesis of Compound 1-4

Under the protection of nitrogen, CDI (749.18 mg, 4.62 mmol) was added to compound 1-3 (1.1 g, 4.62 mmol) in dichlorobenzene (20 mL). The reaction solution was stirred at 190 degrees Celsius for 2 hours. The reaction solution was cooled to room temperature, filtered, and the filter cake was dried to obtain compound 1-4.

$^1$H NMR (400 MHz, DMSO-$d_6$) δ=11.95 (s, 1H), 8.61 (d, J=1.0 Hz, 1H), 8.45 (d, J=2.0 Hz, 1H), 7.62-7.54 (m, 2H), 7.34-7.25 (m, 1H).

Step 4: Synthesis of Compound 1-5

Compound 1-4 (300 mg, 1.14 mmol) and dimethylaniline (621.65 mg, 5.13 mmol) were added to phosphorus oxychloride (5 mL). The reaction solution was stirred at 110 degrees Celsius for 1.5 hours. The reaction solution was concentrated, and the pH was adjusted to 9 with saturated aqueous sodium bicarbonate solution, and a solid was precipitated, the precipitated solid was filtered, and the filter cake was dried to obtain compound 1-5.

$^1$H NMR (400 MHz, DMSO-$d_6$) δ=9.01 (s, 1H), 8.80 (d, J=2.0 Hz, 1H), 7.95 (d, J=8.8 Hz, 1H), 7.91 (s, 1H), 7.84 (dd, J=2.0, 8.8 Hz, 1H).

Step 5: Synthesis of Compound 1-6

4-morpholinoaniline (170.33 mg, 955.68 μmol) and DIEA (148.21 mg, 1.15 mmol) were added to compound 1-5 (270.0 mg, 955.68 μmol) in isopropanol (3 mL). The reaction solution was stirred at 100 degrees Celsius for 32 hours. The reaction solution was filtered, and the filter cake was dried to obtain compound 1-6.

$^1$H NMR (400 MHz, DMSO-$d_6$) δ=9.65 (s, 1H), 8.74 (d, J=1.0 Hz, 1H), 8.48 (s, 1H), 7.99 (d, J=9.0 Hz, 2H), 7.59-7.55 (m, 2H), 7.08-6.91 (m, 3H), 3.78-3.72 (m, 4H), 3.10-3.05 (m, 4H).

Step 6: Synthesis of Compound 1-8

Compound 1-6 (100 mg, 235.69 μmol), compound 1-7 (83.19 mg, 282.83 μmol), potassium carbonate (97.72 mg, 707.07 μmol) and Pd(dppf)$Cl_2$ (17.25 mg, 23.57 μmol) were added to 1,4-dioxane (4 mL) and water (1 mL). Under the protection of nitrogen, the reaction solution was stirred at 80° C. for 4 hours. The reaction solution was added with water (15 mL), and extracted twice with ethyl acetate (15 mL). The organic phases were combined, washed twice with saturated brine (20 mL), dried over anhydrous sodium sulfate, filtered and concentrated to obtain compound 1-8.

Step 7: Synthesis of Compound 1

Trifluoroacetic acid (1.54 g, 13.51 mmol) was added to a solution of compound 1-8 (110.0 mg, 215.02 μmol) in dichloromethane (1 mL). The reaction solution was stirred at 25 degrees Celsius for 1 hour. The pH of the reaction solution was adjusted to 8 with aqueous ammonia, water (10 mL) was added, and the solution was extracted twice with dichloromethane (10 mL). The organic phases were combined and washed twice with saturated brine (10 mL), dried over anhydrous sodium sulfate, filtered and concentrated.

The crude product was added with 3 mL of acetone, heated to 60 degrees Celsius, stirred for 0.5 hours, then cooled to room temperature, filtered, and vacuum dried to obtain compound 1.

$^1$H NMR (400 MHz, DMSO-$d_6$) δ: 8.81 (s, 1H), 8.43 (s, 1H), 8.23 (s, 2H), 7.92 (d, J=8.8 Hz, 2H), 7.80 (s, 1H), 7.77-7.72 (m, 1H), 7.71-7.63 (m, 1H), 7.07 (d, J=8.8 Hz, 2H), 3.79-3.76 (m, 4H), 3.16 (br. s., 4H); MS (ESI) m/z: 412 $[M+H]^+$.

Example 2: Preparation of Compound 2

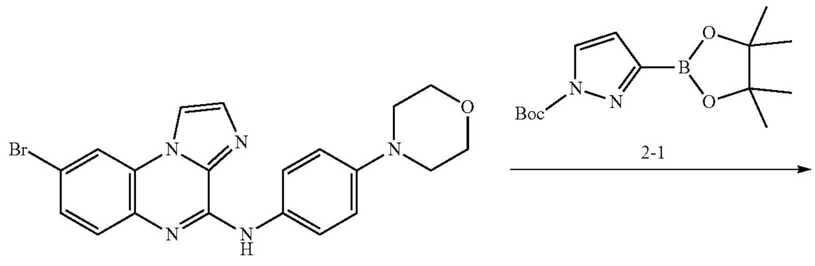

1-6 2-1

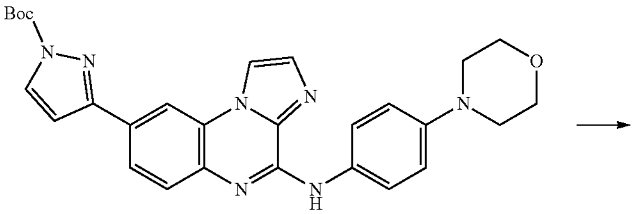

2-2

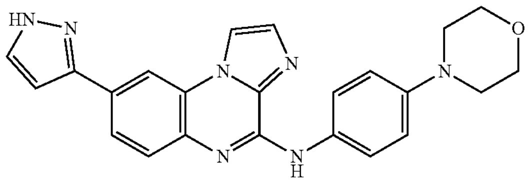

2

Step 1: Synthesis of Compound 2-2

Compound 1-6 (140 mg, 329.96 μmol), compound 2-1 (116.47 mg, 395.95 μmol), potassium carbonate (45.60 mg, 329.96 μmol) and Pd(dppf)$Cl_2$ (24.14 mg, 33 μmol) were added to 1,4-dioxane (4 mL) and water (1 mL). Under the protection of nitrogen, the reaction solution was stirred at 80° C. for 4 hours. The reaction solution was added with water (15 mL), and extracted twice with ethyl acetate (15 mL). The organic phases were combined, washed twice with saturated brine (20 mL), dried over anhydrous sodium sulfate, filtered and concentrated to obtain compound 2-2. MS (ESI) m/z:512 $[M+H]^+$.

Step 2: Synthesis of Compound 2

Trifluoroacetic acid (23.10 g, 202.57 mmol) was added to a solution of compound 2-2 (150.0 mg, 293.22 μmol) in dichloromethane (1 mL). The reaction solution was stirred at 25 degrees Celsius for 2 hours. The pH of the reaction solution was adjusted to 8 with aqueous ammonia, water (10 mL) was added, and the solution was extracted twice with dichloromethane (20 mL). The organic phases were combined and washed twice with saturated brine (10 mL), dried over anhydrous sodium sulfate, filtered and concentrated. The crude product was separated and purified by high performance liquid chromatography (column: 3-Phenomenex Luna C18 75x30 mmx3 μm; mobile phase: [water (0.1% trifluoroacetic acid)-acetonitrile]; B (acetonitrile) %: 45%-75%, 7 min) to obtain compound 2 (trifluoroacetate).

$^1$H NMR (400 MHz, DMSO-$d_6$) δ: 9.76 (br. s., 1H), 8.81 (s, 1H), 8.54 (s, 1H), 8.06-7.90 (m, 3H), 7.81-7.63 (m, 3H), 7.01 (d, J=8.3 Hz, 2H), 6.92 (s, 1H), 3.77 (br. s., 4H), 3.12 (br. s., 2H); MS (ESI) m/z: 412 $[M+H]^+$.

Example 3: Preparation of Compound 3

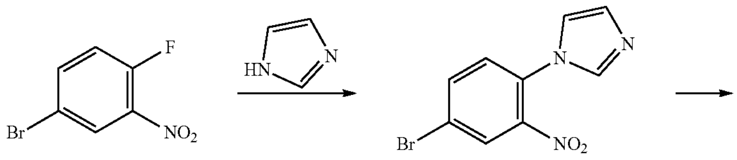

3-1 3-2

-continued

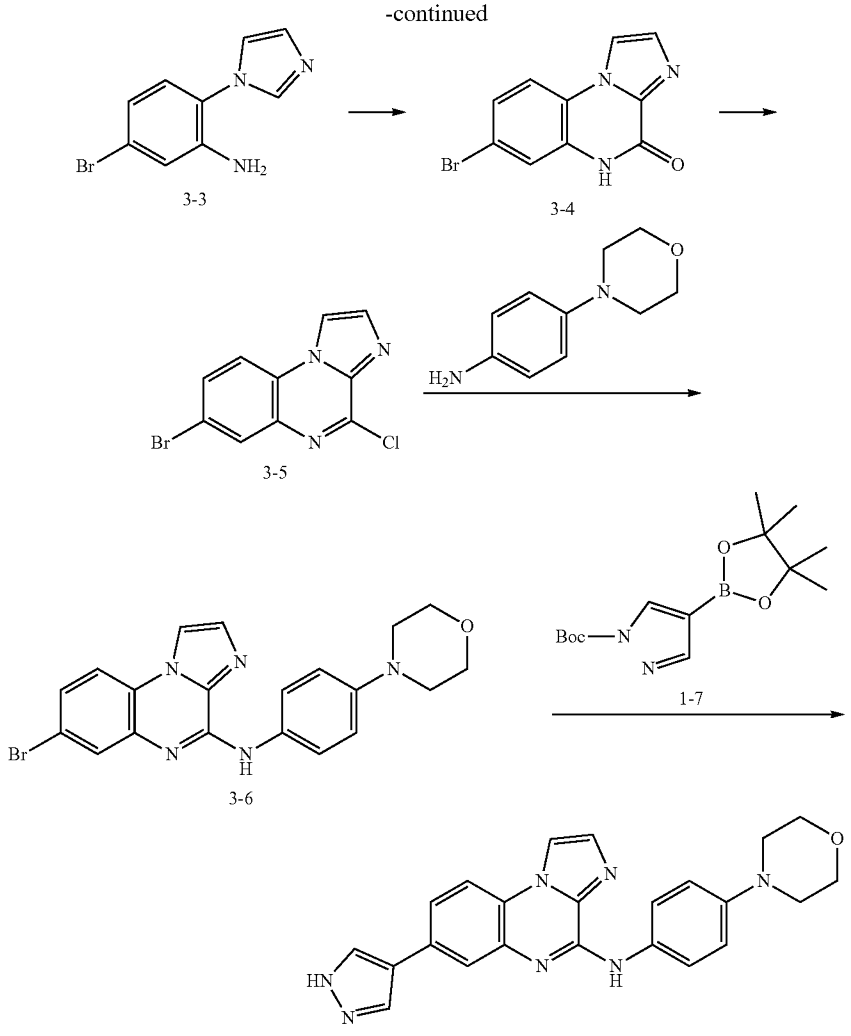

3-3 3-4 3-5 3-6 1-7 3

Step 1: Synthesis of Compound 3-2

Imidazole (3.09 g, 45.45 mmol), and DIEA (5.87 g, 45.45 mmol)) were added to a solution of 4-bromo-1-fluoro-2-nitrobenzene (10 g, 45.45 mmol) in acetonitrile (200 mL). The reaction solution was stirred at 90° C. for 16 hours. The reaction solution was concentrated, water (100 mL) was added, and the mixture was extracted twice with ethyl acetate (50 mL). The organic phases were combined, washed once with saturated brine (50 mL), dried over anhydrous sodium sulfate, filtered and concentrated to obtain compound 3-2.

$^1$H NMR (400 MHz, DMSO-$d_6$) δ=8.19-8.09 (m, 1H), 7.86 (dd, J=2.3, 8.5 Hz, 1H), 7.67-7.56 (m, 1H), 7.39-7.34 (m, 1H), 7.23 (s, 1H), 7.05 (t, J=1.3 Hz, 1H).

Step 2: Synthesis of Compound 3-3

Stannous chloride dihydrate (36.87 g, 163.38 mmol) was added to a solution of compound 3-2 (7.30 g, 27.23 mmol) in ethanol (350 mL). The reaction solution was stirred at 80° C. for 3 hours. The reaction solution was concentrated under reduced pressure, ethyl acetate (300 mL) was added, the solution was neutralized with saturated sodium bicarbonate solution to pH=9, and a white solid was precipitated. The precipitated solid was filtered off. The filtrate was added with water (100 mL) and extracted twice with ethyl acetate (100 mL). The organic phases were combined, washed with saturated brine (300 mL), dried over anhydrous sodium sulfate, filtered and concentrated to obtain compound 3-3.

Step 3: Synthesis of Compound 3-4

Under the protection of nitrogen, CDI (2.23 g, 13.78 mmol) was added to compound 3-3 (1.64 g, 6.89 mmol) in dichlorobenzene (40 mL). The reaction solution was stirred at 190 degrees Celsius for 2 hours. The reaction solution was cooled to room temperature, filtered, and the filter cake was dried to obtain compound 3-4.

$^1$H NMR (400 MHz, DMSO-$d_6$) δ=8.54 (d, J=1.0 Hz, 1H), 8.08 (d, J=8.5 Hz, 1H), 7.60 (d, J=1.3 Hz, 1H), 7.52 (d, J=2.0 Hz, 1H), 7.47 (dd, J=2.1, 8.7 Hz, 1H), 7.06 (s, 1H).

Step 4: Synthesis of Compound 3-5

Compound 3-4 (800 mg, 3.03 mmol) and dimethylaniline (1.66 g, 13.70 mmol) were added to phosphorus oxychloride (10 mL). The reaction solution was stirred at 110 degrees Celsius for 1.5 hours. The reaction solution was concentrated, and the pH was adjusted to 9 with saturated aqueous sodium bicarbonate solution, and a solid was precipitated, the precipitated solid was filtered, and the filter cake was dried and purified by column chromatography (silica gel, petroleum ether/ethyl acetate=100/1 to 2:1) to obtain compound 3-5.

$^1$H NMR (400 MHz, DMSO-$d_6$) δ=8.98 (s, 1H), 8.41 (d, J=8.8 Hz, 1H), 8.25 (d, J=1.8 Hz, 1H), 7.99 (dd, J=2.0, 8.8 Hz, 1H), 7.92 (s, 1H).

Step 5: Synthesis of Compound 3-6

4-morpholinoaniline (174.12 mg, 976.92 μmol) and DIEA (126.26 mg, 976.92 μmol) were added to compound 3-5 (230.0 mg, 814.10 μmol) in isopropanol (5 mL). The reaction solution was stirred at 100 degrees Celsius for 16 hours. The reaction solution was filtered, and the filter cake was dried to obtain compound 3-6.

$^1$H NMR (400 MHz, DMSO-$d_6$) δ=9.72 (s, 1H), 8.68 (d, J=1.3 Hz, 1H), 8.13 (d, J=8.8 Hz, 1H), 8.00 (d, J=9.0 Hz, 2H), 7.80 (d, J=2.3 Hz, 1H), 7.71 (d, J=1.3 Hz, 1H), 7.52 (dd, J=2.1, 8.7 Hz, 1H), 6.95 (d, J=9.0 Hz, 2H), 3.79-3.70 (m, 4H), 3.12-3.00 (m, 4H).

Step 6: Synthesis of Compound 3

Compound 3-6 (90 mg, 212.12 μmol), compound 1-7 (74.87 mg, 254.54 μmol), potassium carbonate (87.95 mg, 636.36 μmol) and Pd(dppf)$Cl_2$ (15.52 mg, 21.21 μmol) were added to 1,4-dioxane (4 mL) and water (1 mL). Under the protection of nitrogen, the reaction solution was stirred at 80° C. for 4 hours. The reaction solution was added with water (15 mL), and extracted twice with ethyl acetate (15 mL). The organic phases were combined and washed twice with saturated brine (20 mL), dried over anhydrous sodium sulfate, filtered and concentrated. The crude product was separated and purified by high performance liquid chromatography (column: 3-Phenomenex Luna C18 75×30 mm×3 μm; mobile phase: [water (0.1% trifluoroacetic acid)-acetonitrile]; B (acetonitrile) %: 45%-75%, 7 min) to obtain compound 3 (trifluoroacetate).

$^1$H NMR (400 MHz, DMSO-$d_6$) δ: 8.74 (s, 1H), 8.25-8.12 (m, 3H), 8.01-7.87 (m, 3H), 7.77 (s, 1H), 7.70 (d, J=8.3 Hz, 1H), 7.08 (d, J=8.3 Hz, 2H), 3.79 (d, J=4.3 Hz, 4H), 3.17 (br. s., 4H); MS (ESI) m/z: 412 [M+H]$^+$.

Example 4: Preparation of Compound 4

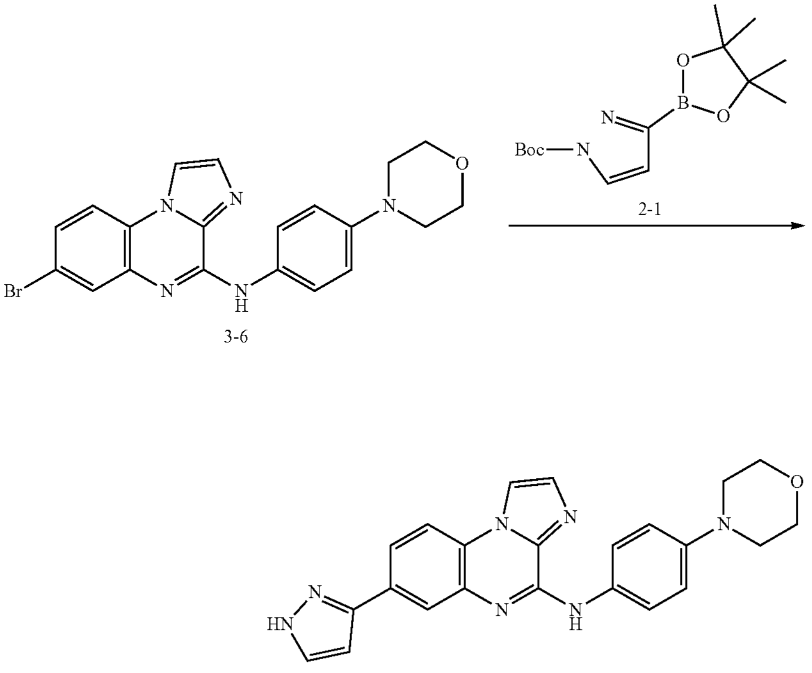

3-6

2-1

4

Compound 3-6 (100 mg, 235.69 μmol), compound 2-1 (83.19 mg, 282.83 μmol), potassium carbonate (97.72 mg, 707.07 μmol) and Pd(dppf)$Cl_2$ (17.25 mg, 23.57 μmol) were added to 1,4-dioxane (4 mL) and water (2 mL). Under the protection of nitrogen, the reaction solution was stirred at 90° C. for 4 hours. The reaction solution was added with water (20 mL), and extracted twice with ethyl acetate (20 mL). The organic phases were combined and washed twice with saturated brine (20 mL), dried over anhydrous sodium sulfate, filtered and concentrated. The crude product was separated and purified by high performance liquid chromatography (column: 3-Phenomenex Luna C18 75×30 mm×3 μm; mobile phase: [water (0.1% trifluoroacetic acid)-acetonitrile]; B (acetonitrile) %: 45%-75%, 7 min) to obtain compound 4 (trifluoroacetate).

$^1$H NMR (400 MHz, DMSO-$d_6$) δ: 8.76 (s, 1H), 8.24 (d, J=8.5 Hz, 1H), 8.17 (s, 1H), 7.95 (d, J=8.0 Hz, 2H), 7.88 (dd, J=1.6, 8.4 Hz, 1H), 7.82-7.73 (m, 2H), 7.10 (d, J=8.8 Hz, 2H), 6.85 (d, J=2.3 Hz, 1H), 3.79 (br. s., 4H), 3.22-3.13 (m, 4H); MS (ESI) m/z: 412 [M+H]$^+$.

Example 5: Preparation of Compound 5
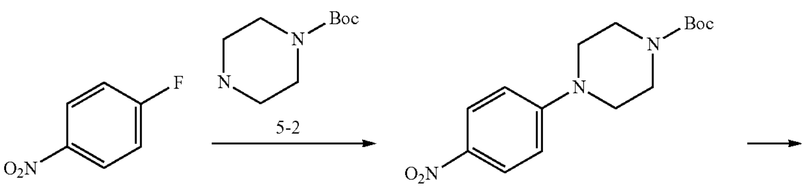
5-1 5-3
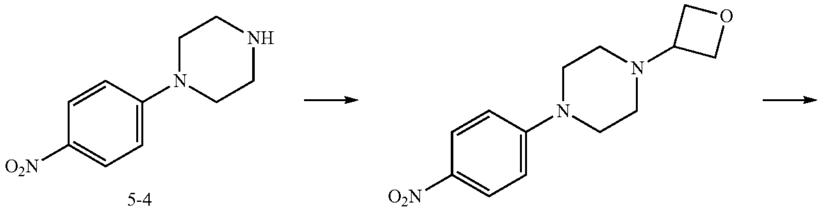
5-4 5-5
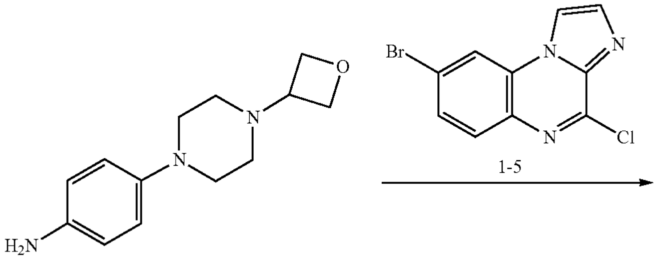
5-6
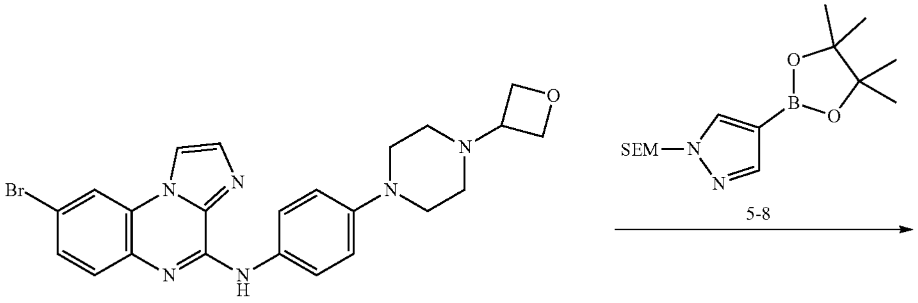
5-7
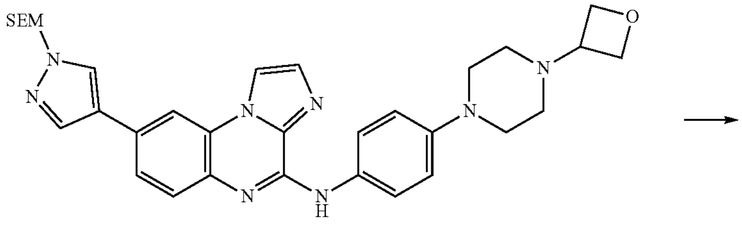
5-9
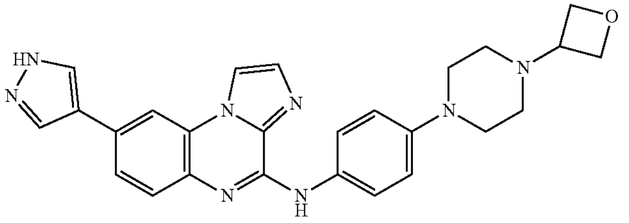
5

Step 1: Synthesis of Compound 5-3

Potassium carbonate (5.88 g, 42.52 mmol), and tert-butyl piperazine-1-carboxylate (3.96 g, 21.26 mmol) were added to a solution of p-fluoronitrobenzene (2 g, 14.17 mmol) in DMSO (20 mL). The reaction solution was stirred at 80 degrees Celsius for 16 hours. The reaction solution was concentrated, water (100 mL) was added, and the mixture was extracted three times with ethyl acetate (50 mL). The organic phases were combined, dried, filtered and concentrated to obtain compound 5-3. [00131]$^{1}$H NMR (400 MHz, DMSO-$d_6$) δ=8.06 (d, J=8.8 Hz, 2H), 7.01 (d, J=9.6 Hz, 2H), 3.47 (s, 8H), 1.42 (s, 9H).

Step 2: Synthesis of Compound 5-4

Compound 5-3 (4.2 g, 13.67 mmol) was added in small batches to a dioxane hydrochloride solution (4 M, 59.81 mL), and the mixture was stirred at room temperature for 16 hours. The reaction solution was concentrated under reduced pressure to obtain compound 5-4 (crude hydrochloride), which was directly used in the next reaction.

$^{1}$H NMR (400 MHz, DMSO-$d_6$) δ=9.45 (br, 1H), 8.11 (d, J=9.6 Hz, 2H), 7.10 (d, J=9.6 Hz, 2H), 3.67-3.69 (m, 4H), 3.20-3.22 (m, 4H)).

Step 3: Synthesis of Compound 5-5

Under the protection of nitrogen, sodium acetate (4.04 g, 49.22 mmol) was added to a solution of compound 5-4 (3.4 g, hydrochloride) in ethanol (40 mL), and the mixture was stirred at room temperature for 1 hour before oxetanone (1.77 g, 14.61 mmol) and zinc chloride (4.47 g, 32.81 mmol) were added, and the mixture was then stirred at room temperature for 2 hours before sodium cyanoborohydride (3.09 g, 49.22 mmol) was added. The reaction solution was stirred at 40 degrees Celsius for 16 hours. The reaction solution was added with water (150 mL), and extracted three times with ethyl acetate (100 mL). The organic phases were combined, washed twice with saturated brine (80 mL), dried over anhydrous sodium sulfate, filtered and concentrated to obtain compound 5-5.

$^{1}$H NMR (400 MHz, DMSO-$d_6$) δ=8.05 (d, J=9.6 Hz, 2H), 7.03 (d, J=9.2 Hz, 2H), 4.45-4.57 (m, 5H), 3.47 (br, 4H), 2.38-2.22 (br, 4H).

Step 4: Synthesis of Compound 5-6

Under the protection of nitrogen, palladium carbon (0.5 g, 2.25 mmol) was added to a solution of compound 5-5 (4.2 g, 15.95 mmol) in methanol (150 mL) and the nitrogen was replaced with hydrogen by a hydrogen balloon three times. The reaction was stirred at room temperature for 16 hours under hydrogen. The reaction solution was filtered, and the filtrate was concentrated and dried to obtain compound 5-6.

MS (ESI) m/z:234 [M+H]$^+$.

Step 5: Synthesis of Compound 5-7

Compound 5-6 (991 mg, 4.25 mmol) and DIEA (686 mg, 5.31 mmol) were added to a solution of compound 1-5 (1.0 g, 3.54 mmol) in isopropanol (10 mL). The reaction solution was stirred at 100 degrees Celsius for 16 hours. The reaction solution was cooled to room temperature, filtered, and the filter cake was dried to obtain compound 5-7.

Step 6: Synthesis of Compound 5-9

Compound 5-7 (200 mg, 417 μmol), compound 5-8 (135.3 mg, 417 μmol), potassium carbonate (173 mg, 1.25 mmol) and Pd(dppf)$Cl_2$ (30.53 mg, 41.72 μmol) were added to 1,4-dioxane (4 mL) and water (5 mL). Under the protection of nitrogen, the reaction solution was stirred at 100° C. for 16 hours. The reaction solution was added with water (30 mL), and extracted three times with ethyl acetate (15 mL). The organic phases were combined, washed twice with saturated brine (20 mL), dried over anhydrous sodium sulfate, filtered and concentrated to obtain compound 5-9.

MS (ESI) m/z:597 [M+H]$^+$.

Step 7: Synthesis of Compound 5

Tetrabutylammonium fluoride (153 mg, 586.5 μmol) and ethylenediamine (70.5 mg, 1.17 mmol) were added to a solution of compound 5-9 (350 mg, 586.5 μmol) in tetrahydrofuran (10 mL). The reaction solution was stirred at 75 degrees Celsius for 16 hours. The pH of the reaction solution was adjusted to 8 with sodium hydroxide solution, water (10 mL) was added, and the solution was extracted twice with dichloromethane (10 mL). The organic phases were combined and washed twice with saturated brine (10 mL), dried over anhydrous sodium sulfate, filtered and concentrated. The crude product was separated by silica gel column chromatography (petroleum ether:ethyl acetate=10%~100%) to obtain compound 5.

$^{1}$H NMR (400 MHz, DMSO-$d_6$) δ=9.44 (s, 1H), 8.74 (d, J=1.0 Hz, 1H), 8.39 (d, J=1.6 Hz, 1H), 8.22 (s, 2H), 8.00 (d, J=9.0 Hz, 3H), 7.75-7.68 (m, 2H), 7.63 (d, J=8.5 Hz, 1H), 6.96 (d, J=9.0 Hz, 2H), 4.61-4.52 (m, 2H), 4.48 (t, J=6.1 Hz, 3H), 3.20-3.03 (m, 4H), 2.42 (br t, J=4.7 Hz, 4H); MS (ESI) m/z: 467 [M+H]$^+$.

Example 6: Preparation of Compound 6

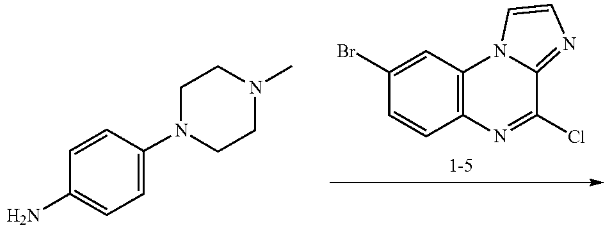

1-5

6-1

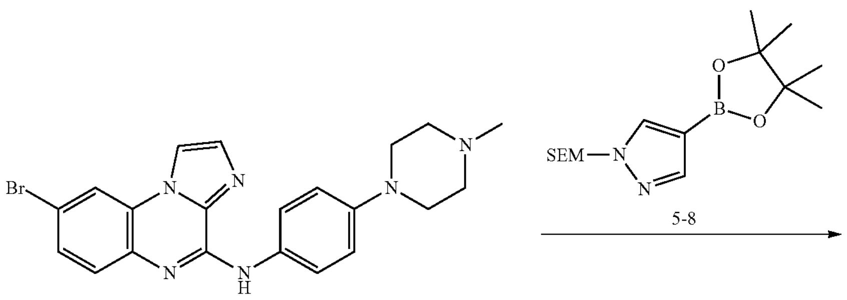

5-8

6-2

-continued

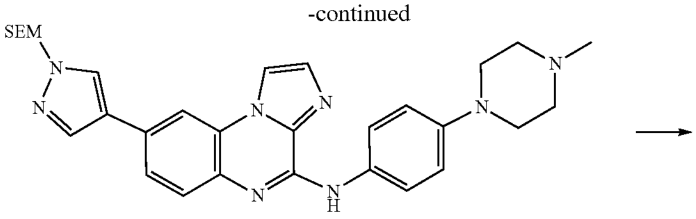

6-3

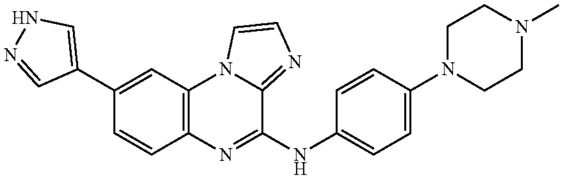

6

Step 1: Synthesis of Compound 6-2

Compound 6-1 (338.55 mg, 1.77 mmol) and DIEA (1.14 g, 8.85 mmol) were added to a solution of compound 1-5 (0.5 g, 1.77 mmol) in dimethyl sulfoxide (7 mL). The reaction solution was stirred at 120 degrees Celsius for 16 hours. After the reaction solution was cooled to room temperature, 50 mL of water was added, a solid was precipitated, filtered, the filter cake was slurried with 10 mL of isopropanol, filtered and dried to obtain compound 6-2.

Step 2: Synthesis of Compound 6-3

Compound 6-2 (400 mg, 914.63 mmol), compound 5-8 (1.19 g, 3.66 mmol), potassium carbonate (379.23 mg, 2.74 mmol) and Pd(dppf)$Cl_2$ (66.92 mg, 91.46 μmol) were added to 1,4-dioxane (12 mL) and water (3 mL). Under the protection of nitrogen, the reaction solution was stirred at 100° C. for 16 hours. The reaction solution was added with water (100 mL), and extracted three times with ethyl acetate (150 mL). The organic phases were combined and washed twice with saturated brine (100 mL), dried over anhydrous sodium sulfate, filtered and concentrated. The crude product was separated by silica gel column chromatography (dichloromethane/methanol, methanol: 0%~10%) to obtain compound 6-3.

MS (ESI) m/z:555 $[M+H]^+$.

Step 3: Synthesis of Compound 6

Compound 6-3 (280 mg, 504.72 μmol) was added to dioxane hydrochloride (4 M, 5 mL). The reaction solution was stirred at 25 degrees Celsius for 16 hours. The pH of the reaction solution was adjusted to 8 with 2 M aqueous sodium hydroxide solution, water (10 mL) was added, and the solution was extracted twice with dichloromethane (10 mL). The organic phases were combined and washed twice with saturated brine (10 mL), dried over anhydrous sodium sulfate, filtered and concentrated. The crude product was added with 3 mL of acetone, and the mixture was stirred for 0.5 hours, filtered, and the filter cake was dried to obtain compound 6.

$^1$H NMR (400 MHz, DMSO-$d_6$) δ=10.80 (br s, 1H), 8.99 (s, 1H), 8.56 (s, 1H), 8.29 (s, 2H), 8.03 (s, 1H), 7.94 (br s, 2H), 7.87-7.81 (m, 1H), 7.79-7.68 (m, 1H), 7.11 (br d, J=8.9 Hz, 2H), 5.52 (s, 1H), 3.84 (br d, J=11.3 Hz, 3H), 3.51 (br d, J=11.0 Hz, 4H), 2.83 (br d, J=4.4 Hz, 4H); MS (ESI) m/z: 425 $[M+H]^+$.

Example 7: Preparation of Compound 7

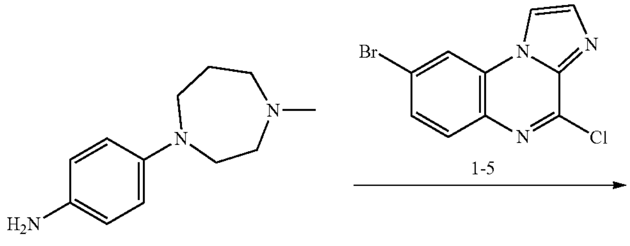

1-5

7-1

-continued

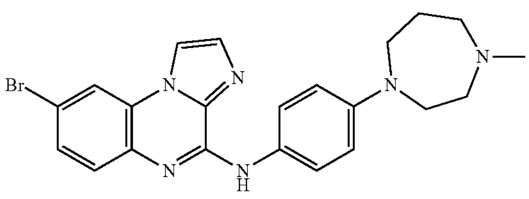

7-2

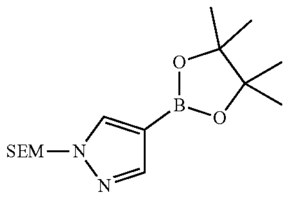

5-8

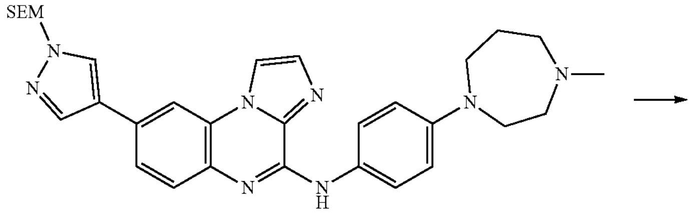

7-3

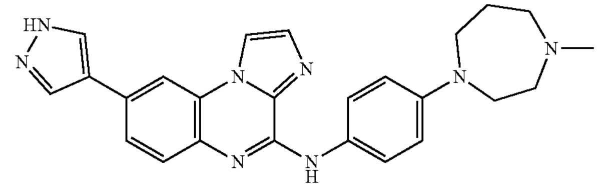

7

Step 1: Synthesis of Compound 7-2

Compound 7-1 (362.85 mg, 1.77 mmol) and DIEA (1.14 g, 8.85 mmol) were added to a solution of compound 1-5 (0.5 g, 1.77 mmol) in dimethyl sulfoxide (7 mL). The reaction solution was stirred at 120 degrees Celsius for 16 hours. After the reaction solution was cooled to room temperature, 50 mL of water was added, a solid was precipitated, filtered, the filter cake was slurried with 10 mL of isopropanol, filtered and dried to obtain compound 7-2.

Step 2: Synthesis of Compound 7-3

Compound 7-2 (123 mg, 272.51 μmol), compound 5-8 (441.87 mg, 1.36 mmol), potassium carbonate (112.99 mg, 817.53 μmol) and Pd(dppf)$Cl_2$ (19.94 mg, 27.25 μmol) were added to 1,4-dioxane (4 mL) and water (1 mL). Under the protection of nitrogen, the reaction solution was stirred at 100° C. for 16 hours. The reaction solution was added with water (50 mL), and extracted three times with ethyl acetate (100 mL). The organic phases were combined and washed twice with saturated brine (50 mL), dried over anhydrous sodium sulfate, filtered and concentrated. The crude product was separated by silica gel column chromatography (dichloromethane:methanol: 0%~10%) to obtain compound 7-3. MS (ESI) m/z:569 $[M+H]^+$.

Step 3: Synthesis of Compound 7

Compound 7-3 (127 mg, 223.28 μmol) was added to dioxane hydrochloride (4 M, 5 mL). The reaction solution was stirred at 25 degrees Celsius for 16 hours. The pH of the reaction solution was adjusted to 8 with 2 M aqueous sodium hydroxide solution, water (10 mL) was added, and the solution was extracted twice with dichloromethane (10 mL). The organic phases were combined and washed twice with saturated brine (10 mL), dried over anhydrous sodium sulfate, filtered and concentrated. The crude product was separated by silica gel column chromatography (dichloromethane/methanol, methanol: 0%~20%) to obtain compound 7.

$^1$H NMR (400 MHz, DMSO-$d_6$) δ=11.20 (br s, 1H), 9.17 (d, J=1.1 Hz, 1H), 8.68 (s, 1H), 8.37 (s, 2H), 8.19 (s, 1H), 7.96-7.68 (m, 2H), 7.46 (s, 1H), 7.33 (s, 1H), 7.20 (s, 1H), 6.96 (br d, J=8.8 Hz, 2H), 3.96-3.74 (m, 2H), 3.74-3.60 (m, 1H), 3.56-3.34 (m, 5H), 3.31-3.03 (m, 2H), 2.81 (d, J=4.8 Hz, 3H); MS (ESI) m/z: 439 $[M+H]^+$.

Example 8: Preparation of Compound 8

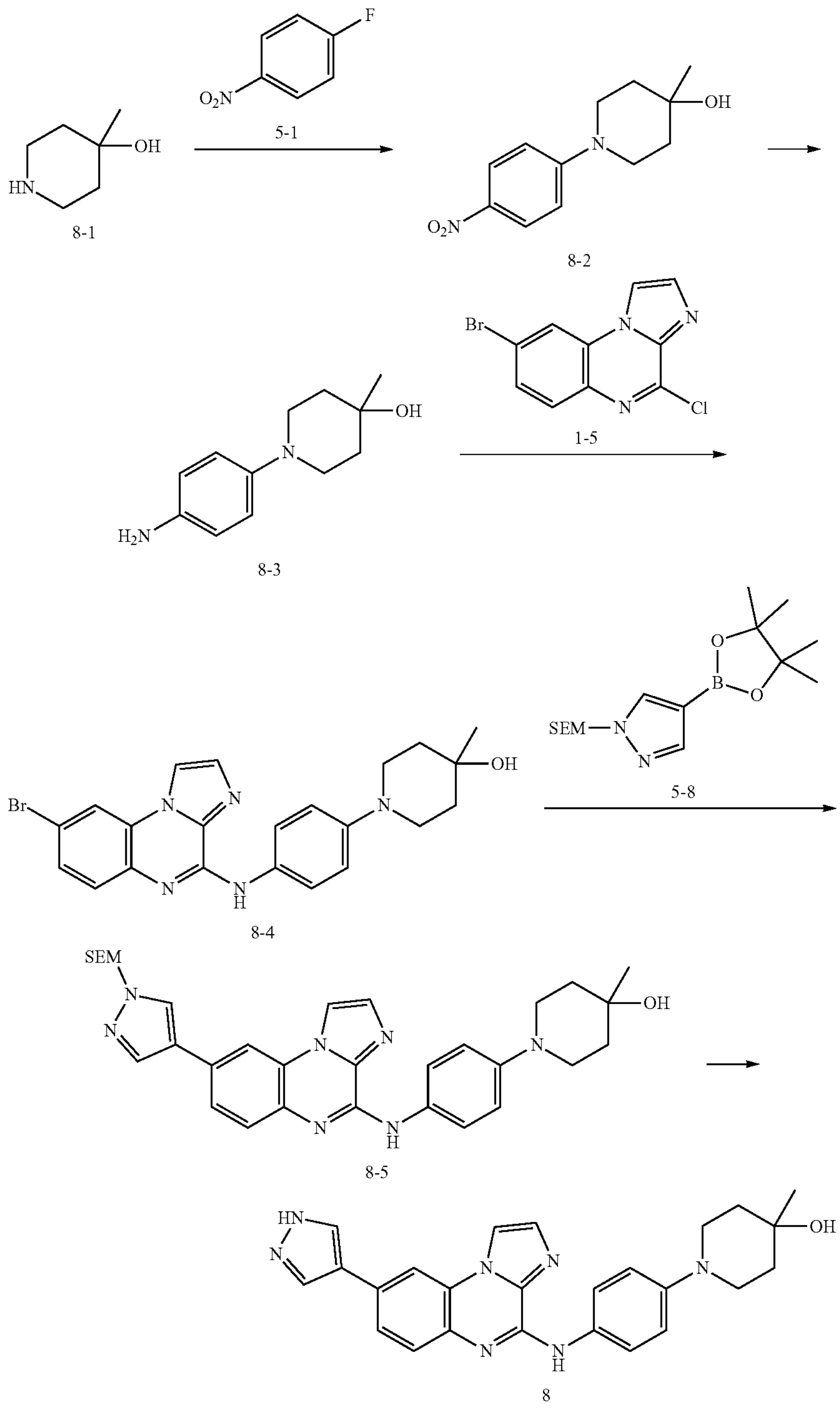

8-1

5-1

8-2

1-5

8-3

5-8

8-4

8-5

8

Step 1: Synthesis of Compound 8-2

Potassium carbonate (2.94 g, 21.26 mmol), compound 8-1 (1.06 g, 9.21 mmol) were added to a solution of compound 5-1 (1 g, 7.09 mmol) in DMSO (20 mL). The reaction solution was stirred at 100 degrees Celsius for 16 hours. The reaction solution was concentrated, water (50 mL) was added, and the mixture was extracted three times with ethyl acetate (50 mL). The organic phases were combined, dried, filtered and concentrated to obtain compound 8-2. MS (ESI) m/z:237 $[M+H]^+$.

Step 2: Synthesis of Compound 8-3

Under the protection of nitrogen, ammonium chloride (1.19 g, 22.22 mmol) and iron powder (2.48 g, 44.44 mmol) were added to a solution of compound 8-2 (1.5 g, 15.95 mmol) in ethanol (8 mL) and water (2 mL). The reaction solution was stirred at 100 degrees Celsius for 16 hours. The reaction solution filtered and the filtrate was added with water (50 mL), and extracted three times with ethyl acetate (50 mL). The organic phases were combined, dried, filtered, concentrated and dried to obtain compound 8-3. MS (ESI) m/z:207 $[M+H]^+$.

Step 3: Synthesis of Compound 8-4

Compound 8-3 (401.63 mg, 1.95 mmol) and DIEA (1.14 g, 8.85 mmol) were added to a solution of compound 1-5 (0.5 g, 1.77 mmol) in dimethyl sulfoxide (7 mL). The reaction solution was stirred at 120 degrees Celsius for 16 hours. After the reaction solution was cooled to room temperature, 50 mL of water was added, a solid was precipitated, filtered, the filter cake was slurried with 10 mL of isopropanol, filtered and dried to obtain compound 8-4.

Step 4: Synthesis of Compound 8-5

Compound 8-4 (340 mg, 751.64 μmol), compound 5-8 (731.26 mg, 2.25 mmol), potassium carbonate (311.65 mg, 2.25 mmol) and $Pd(dppf)Cl_2$ (55 mg, 75.16 μmol) were added to 1,4-dioxane (4 mL) and water (1 mL). Under the protection of nitrogen, the reaction solution was stirred at 100° C. for 16 hours. The reaction solution was added with water (50 mL), and extracted three times with dichloromethane (100 mL). The organic phases were combined and washed twice with saturated brine (50 mL), dried over anhydrous sodium sulfate, filtered and concentrated. The crude product was separated by silica gel column chromatography (dichloromethane/tetrahydrofuran, tetrahydrofuran: 0%~100%) to obtain compound 8-5. MS (ESI) m/z: 570 $[M+H]^+$.

Step 5: Synthesis of Compound 8

Compound 8-5 (350 mg, 614.28 μmol) was added to dioxane hydrochloride (4 M, 5 mL). The reaction solution was stirred at 25 degrees Celsius for 16 hours. The pH of the reaction solution was adjusted to 8 with 2 M aqueous sodium hydroxide solution, water (10 mL) was added, and the solution was extracted twice with dichloromethane (10 mL). The organic phases were combined and washed twice with saturated brine (10 mL), dried over anhydrous sodium sulfate, filtered and concentrated. The crude product was separated by silica gel column chromatography (dichloromethane/methanol, methanol: 0%~20%) to obtain compound 8.

$^1H$ NMR (400 MHz, DMSO-$d_6$) δ=12.71-12.02 (m, 1H), 10.29 (br s, 1H), 8.91 (s, 1H), 8.53 (s, 1H), 8.37 (br d, J=7.5 Hz, 2H), 8.29 (s, 2H), 7.93 (s, 1H), 7.84 (br d, J=8.4 Hz, 3H), 7.80 (s, 1H), 7.77 (s, 1H), 3.24-2.97 (m, 1H), 2.67 (s, 1H), 1.80 (br s, 3H), 1.49-0.33 (m, 6H); MS (ESI) m/z: 440 $[M+H]^+$.

Example 9: Preparation of Compound 9

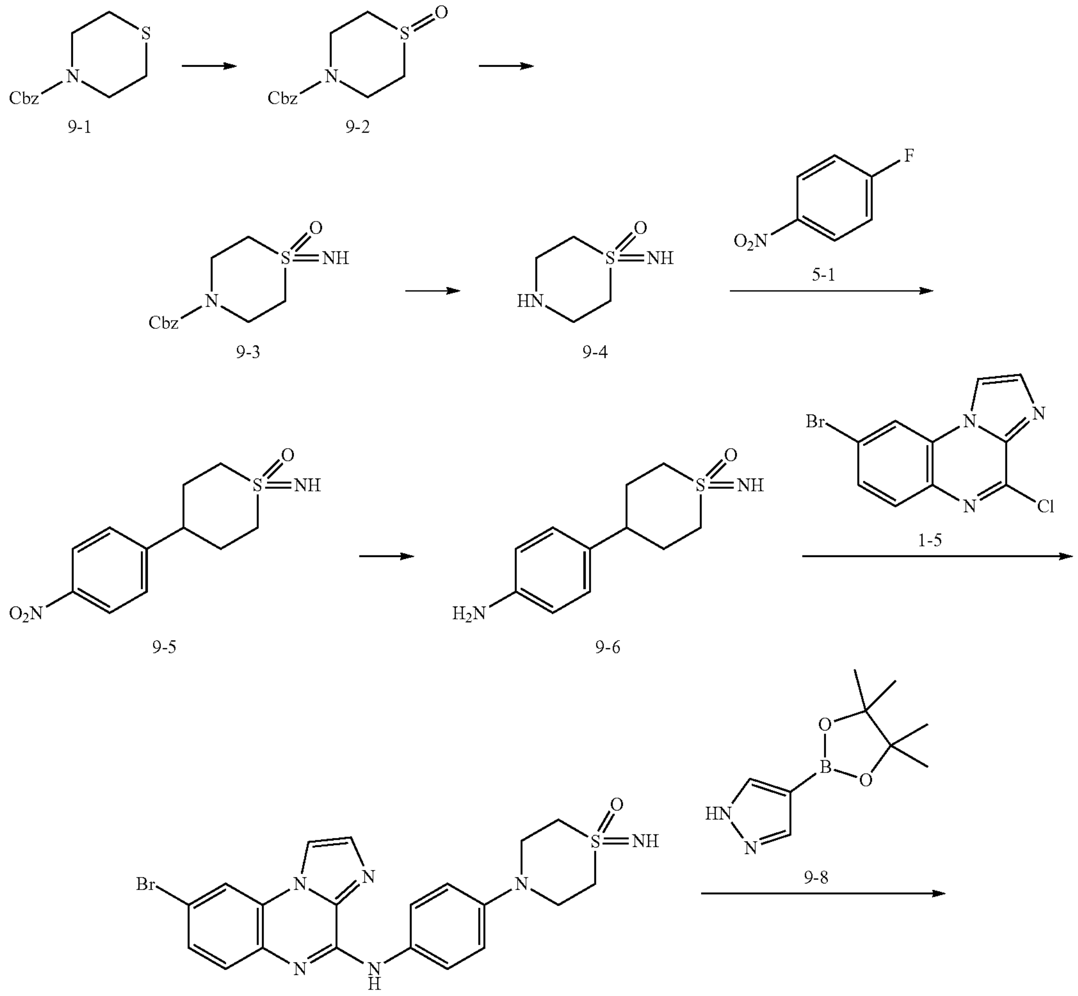
9-1 9-2 9-3 9-4 5-1 9-5 9-6 1-5 9-8 9-7

-continued

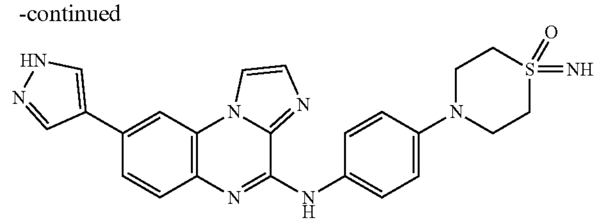

9

Step 1: Synthesis of Compound 9-2

A solution of compound 9-1 (45 g, 189.62 mmol) in methanol (500 mL) and water (200 mL) was cooled to 0 degrees Celsius, and added with sodium periodate (44.61 g, 208.58 mmol). The reaction solution was stirred at 20 degrees Celsius for 16 hours. The reaction solution was filtered and the filter cake was washed three times with ethyl acetate (50 mL). The organic phases were combined, dried over anhydrous sodium sulfate, filtered and concentrated to obtain compound 9-2.

Step 2: Synthesis of Compound 9-3

Under the protection of nitrogen, trifluoroacetamide (17.85 g), rhodium acetate (523.43 mg), magnesium oxide (12.73 g), diacetoxyiodobenzene (38.15 g) and potassium carbonate (54.56 g) were added to a solution of compound 9-2 (20 g, 78.95 mmol) in dichloromethane (300 mL). The reaction solution was stirred at 20 degrees Celsius for 16 hours. The reaction solution was filtered and the filter cake was washed three times with dichloromethane (100 mL). The organic phases were combined, dried over anhydrous sodium sulfate, filtered and concentrated to obtain a crude product which was separated by silica gel column chromatography (petroleum ether/ethyl acetate:ethyl acetate=0%~50%) to obtain compound 9-3.

Step 3: Synthesis of Compound 9-4

Compound 9-3 (16.0 g) was added to a solution of hydrobromic acid (45%, w/v) in acetic acid (60 mL). The reaction solution was stirred at 20 degrees Celsius for 10 hours. The pH of the reaction solution was adjusted to 8 with 2 M aqueous sodium hydroxide solution, water (100 mL) was added, and the solution was extracted three times with dichloromethane (150 mL). The organic phases were combined, washed twice with saturated brine (100 mL), dried over anhydrous sodium sulfate, filtered and concentrated to obtain compound 9-4.

Step 4: Synthesis of Compound 9-5

Potassium carbonate (2.94 g, 21.26 mmol), compound 9-4 (1.14 g, 8.50 mmol) were added to a solution of compound 5-1 (1 g, 7.09 mmol) in DMSO (10 mL). The reaction solution was stirred at 100 degrees Celsius for 16 hours. The reaction solution was concentrated, water (50 mL) was added, and the mixture was extracted three times with ethyl acetate (50 mL). The organic phases were combined, dried over anhydrous sodium sulfate, filtered and concentrated to obtain compound 9-5. MS (ESI) m/z:256 $[M+H]^+$.

Step 5: Synthesis of Compound 9-6

Under the protection of nitrogen, ammonium chloride (1.05 g, 19.59 mmol) and iron powder (1.09 g, 19.59 mmol) were added to a solution of compound 9-5 (1.0 g, 3.92 mmol) in ethanol (20 mL) and water (5 mL). The reaction solution was stirred at 90 degrees Celsius for 1 hour. The reaction solution was filtered and the filtrate was added with water (50 mL), and extracted three times with ethyl acetate (50 mL). The organic phases were combined, dried over anhydrous sodium sulfate, filtered and concentrated to obtain compound 9-6. MS (ESI) m/z:226 $[M+H]^+$.

Step 6: Synthesis of Compound 9-7

Compound 9-6 (0.3 g, 1.33 mmol) and DIEA (516.25 mg, 3.99 mmol) were added to a solution of compound 1-5 (376.18 mg, 1.33 mmol) in dimethyl sulfoxide (10 mL). The reaction solution was stirred at 120 degrees Celsius for 16 hours. After the reaction solution was cooled to room temperature, 50 mL of water was added, a solid was precipitated, filtered, the filter cake was slurried with 10 mL of isopropanol, filtered and dried to obtain compound 9-7.

Step 7: Synthesis of Compound 9

Compound 9-7 (200 mg, 424.29 μmol), compound 9-8 (164.66 mg, 848.58 μmol), potassium carbonate (175.92 mg, 1.27 mmol) and Pd(dppf)$Cl_2$ (31.05 mg, 42.43 μmol) were added to 1,4-dioxane (8 mL) and water (2 mL). Under the protection of nitrogen, the reaction solution was stirred at 100° C. for 16 hours. The reaction solution was added with water (50 mL), and extracted three times with dichloromethane (100 mL). The organic phases were combined and washed twice with saturated brine (50 mL), dried over anhydrous sodium sulfate, filtered and concentrated. The crude product was separated and purified by high performance liquid chromatography (column: 3-Phenomenex Luna C18 75×30 mm×3 μm; mobile phase: [water (0.1% trifluoroacetic acid)-acetonitrile]; B (acetonitrile) %: 45%-75%, 7 min) to obtain compound 9 (trifluoroacetate).

$^1H$ NMR (400 MHz, DMSO-$d_6$): δ=10.75 (br s, 1H), 9.08 (s, 1H), 8.62 (s, 1H), 8.32 (s, 2H), 8.14 (s, 1H), 7.97 (br d, J=7.5 Hz, 2H), 7.83-7.89 (m, 1H), 7.76-7.81 (m, 1H), 7.18 (br d, J=9.0 Hz, 2H), 4.28 (br d, J=14.6 Hz, 4H), 4.08 (br d, J=13.6 Hz, 2H), 3.76 (br t, J=10.8 Hz, 2H), 3.59-3.67 (m, 2H); MS (ESI) m/z: 459 $[M+H]^+$.

Example 10: Preparation of Compound 10

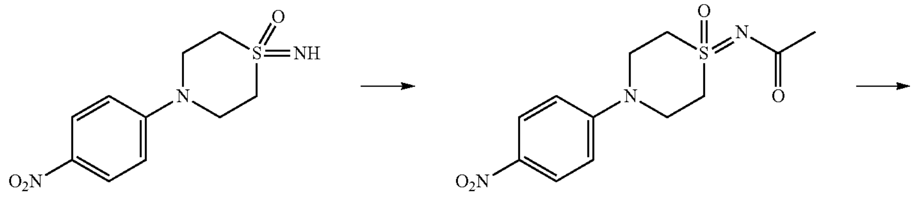

9-5 10-1

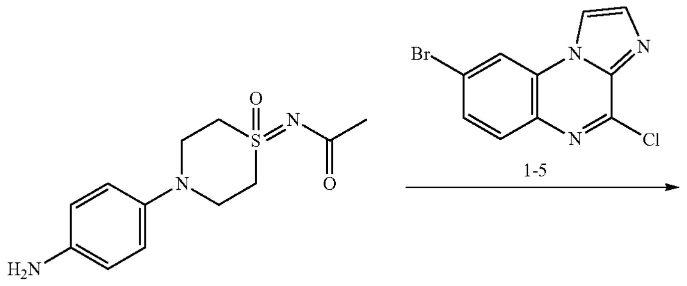

1-5

10-2

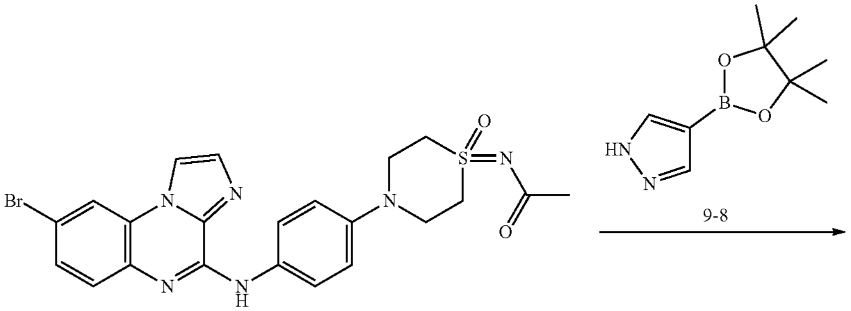

9-8

10-3

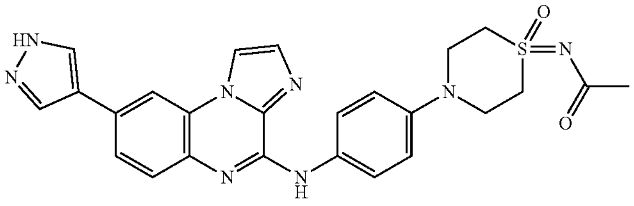

10

Step 1: Synthesis of Compound 10-1

Triethylamine (817.81 μl) and acetyl chloride (209.65 μl) were added to a solution of compound 9-5 (0.5 g, 1.96 mmol) in dichloromethane (10 mL). The reaction solution was stirred at 25 degrees Celsius for 2 hours. The reaction solution was added with water (50 mL), and extracted three times with dichloromethane (100 mL). The organic phases were combined, washed twice with saturated brine (50 mL), dried over anhydrous sodium sulfate, filtered and concentrated to obtain compound 10-1.

Step 2: Synthesis of Compound 10-2

Under the protection of nitrogen, ammonium chloride (449.76 mg) and iron powder (469.55 mg) were added to a solution of compound 10-1 (0.5 g, 1.68 mmol) in ethanol (20 mL) and water (5 mL). The reaction solution was stirred at 90 degrees Celsius for 1 hour. The reaction solution was filtered and the filtrate was added with water (50 mL), and extracted three times with ethyl acetate (50 mL). The organic phases were combined, dried, filtered, concentrated and dried to obtain compound 10-2. MS (ESI) m/z:268 $[M+H]^+$.

Step 3: Synthesis of Compound 10-3

Compound 10-2 (0.2 g) and DIEA (390.91 μl) were added to a solution of compound 1-5 (211.35 mg) in dimethyl sulfoxide (10 mL). The reaction solution was stirred at 120 degrees Celsius for 16 hours. After the reaction solution was cooled to room temperature, 50 mL of water was added, a solid was precipitated, filtered, the filter cake was slurried with 10 mL of isopropanol, filtered and dried to obtain compound 10-3.

Step 4: Synthesis of Compound 10

Compound 10-3 (200 mg), compound 9-8 (151.18 mg), potassium carbonate (161.52 mg) and Pd(dppf)$Cl_2$ (28.50 mg) were added to 1,4-dioxane (8 mL) and water (2 mL). Under the protection of nitrogen, the reaction solution was stirred at 100° C. for 16 hours. The reaction solution was added with water (50 mL), and extracted three times with dichloromethane (100 mL). The organic phases were combined, washed twice with saturated brine (50 mL), dried over anhydrous sodium sulfate, filtered and concentrated to obtain a crude product which was separated and purified by silica gel column chromatography (dichloromethane/methanol, methanol: 0%~10%) to obtain compound 10.

$^1$H NMR (400 MHz, DMSO-$d_6$): δ=13.01 (br s, 1H), 9.55 (s, 1H), 8.76 (s, 1H), 8.42 (s, 1H), 8.33 (br s, 1H), 8.09 (br d, J=9.0 Hz, 2H), 7.72-7.78 (m, 2H), 7.64 (d, J=8.5 Hz, 1H), 7.07 (br d, J=9.0 Hz, 2H), 3.87-3.95 (m, 2H), 3.59-3.68 (m, 3H), 3.41 (br d, J=11.3 Hz, 2H), 3.31 (br s, 2H), 1.99 (s, 3H); MS (ESI) m/z: 501 [M+H]$^+$.

Example 11: Preparation of Compound 11

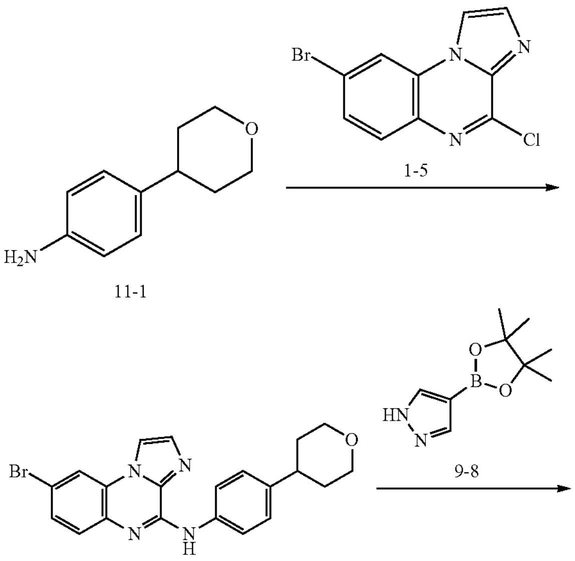

11-1

1-5

9-8

11-2

-continued

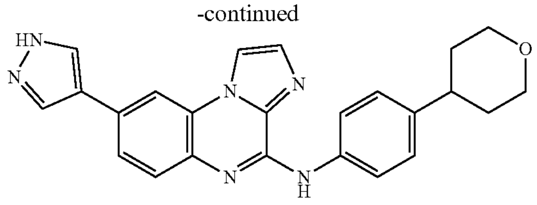

11

Step 1: Synthesis of Compound 11-2

Under the protection of nitrogen, compound 1-5 (300 mg, 1.06 mmol) and compound 11-1 (225.85 mg, 1.27 mmol) were mixed and stirred at 120 degrees Celsius for 16 hours. After the reaction solution was cooled to room temperature, 10 mL of dichloromethane and 2 mL of methanol were added, the mixture was stirred for 15 minutes, filtered, and the filter cake was collected and dried under vacuum to obtain compound 11-2. MS (ESI) m/z:423, 425[M+H]$^+$.

Step 2: Synthesis of Compound 11

Compound 11-2 (100 mg), compound 9-8 (236 mg), potassium carbonate (97.75 mg) and Pd(dppf)$Cl_2$ (17.29 mg) were added to 1,4-dioxane (4 mL) and water (1 mL). Under the protection of nitrogen, the reaction solution was stirred at 100° C. for 16 hours. The reaction solution was added with water (20 mL), and extracted three times with dichloromethane (30 mL). The organic phases were combined and washed twice with saturated brine (30 mL), dried over anhydrous sodium sulfate, filtered and concentrated. The crude product was separated and purified by silica gel column chromatography (dichloromethane/methanol, methanol: 0%~10%) to obtain compound 11.

$^1$H NMR (400 MHz, DMSO-$d_6$): δ=10.61 (br s, 1H), 9.05 (s, 1H), 8.60 (s, 1H), 8.32 (s, 2H), 8.12 (s, 1H), 8.00 (br d, J=8.1 Hz, 2H), 7.84-7.91 (m, 1H), 7.76-7.82 (m, 1H), 7.33 (br d, J=8.4 Hz, 2H), 5.75 (s, 1H), 3.96 (br d, J=10.5 Hz, 2H), 3.45 (td, J=10.7, 3.6 Hz, 2H), 2.73-2.84 (m, 1H), 1.64-1.78 (m, 4H); MS (ESI) m/z: 411 [M+H]$^+$.

Example 12: Preparation of Compound 12

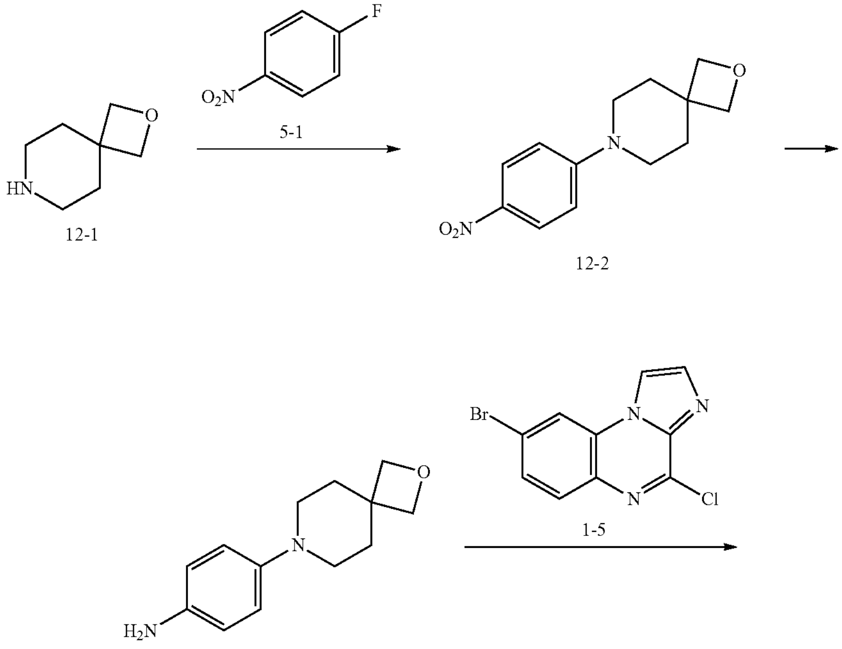

5-1

12-1

12-2

1-5

12-3

-continued

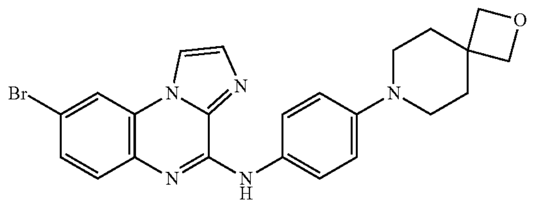

12-4

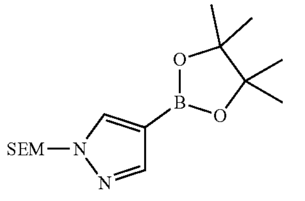

5-8

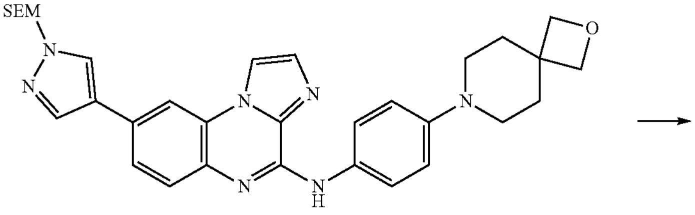

12-5

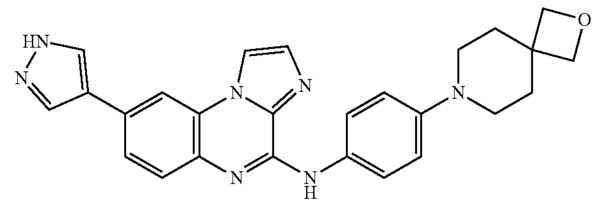

12

Step 1: Synthesis of Compound 12-2

Potassium carbonate (1.47 g), compound 12-1 (585.89 mg) were added to a solution of compound 5-1 (0.5 g) in DMSO (20 mL). The reaction solution was stirred at 100 degrees Celsius for 16 hours. The reaction solution was concentrated, water (50 mL) was added, and the mixture was extracted three times with ethyl acetate (50 mL). The organic phases were combined, dried over anhydrous sodium sulfate, filtered and concentrated to obtain compound 12-2. MS (ESI) m/z:249 $[M+H]^+$.

Step 2: Synthesis of Compound 12-3

Under the protection of nitrogen, ammonium chloride (603.26 mg) and iron powder (1.26 g) were added to a solution of compound 12-2 (0.8 g) in ethanol (8 mL) and water (2 mL). The reaction solution was stirred at 100 degrees Celsius for 16 hours. The reaction solution was filtered and the filtrate was added with water (50 mL), and extracted three times with ethyl acetate (50 mL). The organic phases were combined, dried over anhydrous sodium sulfate, filtered and concentrated to obtain compound 12-3. MS (ESI) m/z:219 $[M+H]^+$.

Step 3: Synthesis of Compound 12-4

Compound 12-3 (154.53 mg) and DIEA (123.30 μl) were added to a solution of compound 1-5 (200 mg) in isopropanol (2 mL). The reaction solution was stirred at 120 degrees Celsius for 16 hours. The reaction solution was cooled to room temperature, added with water (50 mL), and extracted three times with ethyl acetate (50 mL). The organic phases were combined, dried over anhydrous sodium sulfate, filtered and concentrated. The crude product was separated and purified by silica gel column chromatography (dichloromethane/tetrahydrofuran, tetrahydrofuran: 0%~20%) to obtain compound 12-4. MS (ESI) m/z:464, 466$[M+H]^+$.

Step 4: Synthesis of Compound 12-5

Compound 12-4 (126.54 mg), compound 5-8 (441.87 mg), potassium carbonate (112.99 mg) and Pd(dppf)$Cl_2$ (19.94 mg) were added to 1,4-dioxane (8 mL) and water (2 mL). Under the protection of nitrogen, the reaction solution was stirred at 100° C. for 16 hours. The reaction solution was added with water (50 mL), and extracted three times with dichloromethane (100 mL). The organic phases were combined and washed twice with saturated brine (50 mL), dried over anhydrous sodium sulfate, filtered and concentrated. The crude product was separated by silica gel column chromatography (dichloromethane/tetrahydrofuran, tetrahydrofuran: 0%~100%) to obtain compound 12-5. MS (ESI) m/z:582 $[M+H]^+$.

Step 5: Synthesis of Compound 12

Compound 12-5 (50 mg) was added to dioxane hydrochloride (4 M, 5 mL). The reaction solution was stirred at 25 degrees Celsius for 16 hours. The pH of the reaction solution was adjusted to 8 with 2 M aqueous sodium hydroxide solution, water (10 mL) was added, and the solution was extracted twice with dichloromethane (10 mL). The organic phases were combined, washed twice with saturated brine (10 mL), dried over anhydrous sodium sulfate, filtered and concentrated to obtain compound 12.

$^1H$ NMR (400 MHz, DMSO-$d_6$) δ=10.14 (br, 1H), 8.84-8.86 (m, 1H), 8.51 (s, 1H), 8.42 (d, J=8.9 Hz, 2H), 8.27 (s, 1H), 7.87-7.62 (m, 3H), 7.33-7.10 (m, 2H), 6.67 (s, 1H), 5.75 (s, 1H), 3.98-3.91 (m, 4H), 3.71 (s, 4H), 0.98-0.68 (m, 4H); MS (ESI) m/z: 452 $[M+H]^+$.

Biological Test Data:

Experimental Example 1: In Vitro Test of the Compound's Inhibitory Effect on Syk Kinase (Enzymatic Experiment)

Experimental Purpose:

The interaction between the substrate and the enzyme was detected by HTRF, using the IC50 value of the compound as an indicator to evaluate the inhibitory effect of the compound on Syk kinase.

Experimental Materials:

Syk kinase (Invitrogen, PV3857)
DTT (Sigma #43815)
ATP (Sigma #A7699)
$MgCl_2$ (Sigma #63020)
$MnCl_2$ (Sigma #M1787)
EDTA (Invitrogen #15575-020)
HEPES Buffer (Invitrogen #15630-080)
HTRF® KinEASE™ TK (Cisbio #62TKOPEC, 20000 tests)
Low volume, 384-well, white polystyrene plate (Greiner #784075)
384 Well Microplates (Greiner #781946)
Centrifuge (Eppendorf #5810R)
Pipette (Eppendorf)
Pipette (Greiner)
Pipette gun (Eppendorf)
Mutidorp Pipette
POD 810 Plate Assembler Automatic Microplate Pretreatment System
Envision Reader Experimental Steps and Methods:

a) Compound dilution and plate-making:

1) The compound powder was weighed, dissolved in a certain amount of DMSO at an initial concentration of 10 mM.
2) The compound was diluted to a concentration of 0.74 mM, and plated with POD18, 135 nL per well, the starting compound concentration was 10 μM, and there were 11 concentration points, with 3-fold descending serial dilutions.

b) Enzyme-substrate reaction stage:

1) Preparation and dilution of the experimental buffer: the 5×HTRF Buffer in the kit was diluted to 1×, and specified amounts of DTT and $MgCl_2$ solutions were added for use.
2) SYK enzyme reaction solution was prepared with 1×HTRF Buffer so that the final reaction concentration of SYK kinase was 0.0156 ng/μL.
3) TK-Substrate-biotin/ATP mixture was prepared so that the final substrate concentration was controlled at 0.2 μM. ATP concentration was controlled at 2 μM.
4) The solution and the mixture were added with a Mutidorp pipette, SYK enzyme solution and TK-Substrate-biotin/ATP mixture were each added 5 μL per well, and incubated with 23 solution for 1 hour.

c) Detection stage:

1) 13.33 mL of ethylenediaminetetraacetic acid solution was added to the detection buffer of the kit, and specified amounts of Eu-labeled antibody and XL-665 were added to prepare the detection solution.
2) The solution was added with a Mutidorp pipette, 10 μL of detection solution per well, and incubated with 23 solution for 1 hour. The reaction of the enzyme and substrate mixture was stopped.
3) After centrifugation, the reading was obtained on Envision.

d) Data analyzation: the data was analyzed using XL-Fit and the $IC_{50}$ value of the compound was calculated.

Experimental Results:

The experimental results are shown in Table 1.

Experimental Example 2: In Vitro Test of the Compound's Inhibitory Effect on VEGFR2 Kinase (Enzymatic Experiment)

Experimental Purpose:

The VEGFR2 kinase assay kit is intended for measuring VEGFR2 kinase activity using Kinase-Glo®MAX as a detection reagent, and compound screening and analysis were conducted using the $IC_{50}$ value of the compound as an indicator.

Experimental Methods and Procedures:

The ADP-GLO™ Kinase Assay is an analytical reaction in which a luminescent kinase is used to determine the adenosine diphosphate formed by the kinase; ADP is converted to ATP, i.e., an optical signal is generated by Ultra-Glo™ luciferase. The optical signal is positively correlated with ADP quantity and kinase activity. This assay is ideal for determining the activity of the compound, making it ideal for primary screening and kinase selectivity analysis. The ADP-Glo™ Kinase Assay can be used to monitor the activity of virtually any ADP-producing enzyme such as a kinase orATPase:

1) The enzyme, substrate, ATP and inhibitor were diluted in a kinase buffer;
2) 384-well plate: 1 μL of inhibitor or (5% dimethyl sulfoxide solution), 2 μL of KDR enzyme, 2 μL of matrix/ATP mixture;
3) the mixture was incubated at room temperature for 60 minutes;
4) 5 μL of ADP-GLO™ reagent was added;
5) the mixture was incubated for 40 minutes at room temperature;
6) 10 μL of kinase detection reagent was added;
7) the mixture was incubated at room temperature for 30 minutes;
8) the luminescence was recorded (integration time 0.5-1 sec). The data was shown in relative light units (rlu), which was directly related to the amount of ATP produced. There was correlation between the percent of the conversion from ATP to ADP for each kinase amount and the corresponding signal-to-background ratio.
9) Data analysis: (a) KDR enzyme was titrated with 50 μM of ATP, and the luminescent signal produced by KDR enzyme was shown; (b) staurosporine dose response was generated with 1.5 ng of KDR to determine the $IC_{50}$ value of the inhibitor.

Experimental results: the results are shown in Table 1:

TABLE 1

Experimental data of the inhibition of Syk enzyme and VEFGR2 enzyme by the invention compounds

| Compound No. | $IC_{50}$ (nM) for inhibition of Syk enzyme | $IC_{50}$ (nM) for inhibition of VEFGR2 enzyme |
|---|---|---|
| Compound 1 | 15 | 23 |
| Compound 2 | 125 | 31 |
| Compound 5 | 17 | 19 |
| Compound 6 | 50 | 44 |

TABLE 1-continued

Experimental data of the inhibition of Syk enzyme and VEFGR2 enzyme by the invention compounds

| Compound No. | $IC_{50}$ (nM) for inhibition of Syk enzyme | $IC_{50}$ (nM) for inhibition of VEFGR2 enzyme |
|---|---|---|
| Compound 7 | 34 | 42 |
| Compound 8 | 30 | 31 |
| Compound 9 | 23 | 22 |
| Compound 10 | 11 | 41 |
| Compound 11 | 34 | 56 |
| Compound 12 | 315 | 88 |

The results showed: the compound of the invention has significant inhibitory effect on spleen tyrosine kinase (Syk) and vascular endothelial growth factor 2 (VEGFR2).

Experimental Example 3: Activity Inhibition Test of the Compound on 67 Off-Target Kinases (Enzymatic Experiment)

Experimental Purpose:

In order to investigate the specificity of the inhibition of the target by the compound, in this study, the activity and selectivity of test compound 1 on the off-target kinases in related pathways were tested on the Eurofins kinaseProfiler™ platform, and compound screening and analysis were conducted using $IC_{50}$ value as the indicator.

Experimental Methods and Procedures:

Compound 1 was detected for each selected kinase using the standard Eurofins Kinase Profiler™ protocol, which followed the relevant standard operating procedures. The $IC_{50}$ values of the inhibitory activity of the test compound 1 on 67 kinases including Abl(h), B-Raf(h), BTK(h) and JAK(h) were analyzed.

Experimental results: the experimental results are shown in Table 2:

TABLE 2

$IC_{50}$ of the inhibition of sixty-seven off-target kinases by compound 1

| Kinase Name | $IC_{50}$ (nM) Compound 1 | Kinase Name | $IC_{50}$ (nM) Compound 1 |
|---|---|---|---|
| Abl(h) | 152 | JNK1α1(h) | 1172 |
| ACTR2(h) | >10,000 | JNK2α2(h) | >10,000 |
| BRK(h) | 775 | JNK3(h) | 279 |
| B-Raf(h) | 91 | PDGFRα(h) | 2702 |
| CDK2/cyclinA(h) | >10,000 | MAPK1(h) | >10,000 |
| CDK4/cyclinD3(h) | >10,000 | MAP4K4(h) | 63 |
| CDK6/cyclinD3(h) | >10,000 | MAPKAP-K2(h) | >10,000 |
| CSK(h) | >10,000 | MEK1(h) | >10,000 |
| CHK1(h) | >10,000 | MEK2(h) | >10,000 |
| CK1ε(h) | 385 | MKK4(m) | >10,000 |
| FGFR1(h) | 847 | MKK6(h) | >10,000 |
| FGFR3(h) | >10,000 | mTOR(h) | >10,000 |
| Flt1(h) | 104 | mTOR/FKBP12(h) | >10,000 |
| Fyn(h) | 373 | MSK1(h) | >10,000 |
| IKKα(h) | 946 | PKA(h) | >10,000 |
| IKKβ(h) | >10,000 | PKBα(h) | >10,000 |
| Flt3(h) | 12 | ROCK-II(h) | 499 |
| Aurora-B(h) | 232 | Ret(h) | 756 |
| BTK(h) | 1039 | Ros(h) | >10,000 |
| c-kit(h) | 2843 | Rse(h) | >10,000 |
| cSRC(h) | 367 | SAPK2a(h) | >10,000 |
| EGFR(h) | >10,000 | SAPK2b(h) | >10,000 |
| ErbB2(h) | >10,000 | SAPK3(h) | >10,000 |
| FAK(h) | 469 | SAPK4(h) | >10,000 |
| FGFR2(h) | >10,000 | Src(1-530)(h) | 827 |

TABLE 2-continued $IC_{50}$ of the inhibition of sixty-seven off-target kinases by compound 1

| Kinase Name | $IC_{50}$ (nM) Compound 1 | Kinase Name | $IC_{50}$ (nM) Compound 1 |
|---|---|---|---|
| Hck(h)activated | 418 | Src(T341M)(h) | 1006 |
| Itk(h) | 1849 | TGFBR1(h) | >10,000 |
| JAK1(h) | 663 | Tie2(h) | 2059 |
| JAK2(h) | 141 | TrkA(h) | 112 |
| JAK3(h) | 550 | Txk(h) | 227 |
| Lck(h)activated | 1311 | TYK2(h) | 117 |
| Lyn(h) | 934 | Yes(h) | 204 |
| IR(h) | >10,000 | | |

The results showed: the compound of the invention exhibited very good target specificity, and had no other off-target selectivity problems.

Experimental Example 4: Evaluation of the Compound's Inhibition of Cytochrome P450 Enzymes In Vitro Experimental Purpose:

In order to investigate the activity of the compound on human liver microsomal CYP450 enzyme, Liquid Chromatography-Mass Spectrometry/Mass Spectrometry (LC-MS/MS) method was used in this study to determine the inhibitory effect of compound 1 on five main subtypes (CYP1A2, 2C9, 2C19, 2D6, 3A4) of human hepatocyte CYP450 enzyme, and compound screening and analysis were conducted using $IC_{50}$ value as the indicator.

Experimental Methods and Procedures:

1) A test compound and a standard inhibitor working solution (100×) were prepared;
2) microsomes were taken out of a −80° C. freezer, thawed on ice, labeled with the date, and put back in the freezer immediately after use;
3) 20 microliters of matrix solution was added to the corresponding wells;
4) 20 microliters of phosphate buffered saline was added to the blank wells;
5) 2 microliters of the test compound and positive control working solution were added to the corresponding wells;
6) 2 microliters of solvent was added to each of the inhibitor-free wells and the blank wells;
7) human liver microsome working solution was prepared;
8) 158 microliters of HLM working solution was added to all wells of the incubation plate;
9) the plate was heated in a 37° C. water bath for about 10 minutes;
10) NADPH cofactor solution was prepared;
11) 20 microliters of NADPH cofactor was added to all of the incubation wells;
12) all CYPs were subjected to mixed culture in a 37° C. water bath for 10 minutes;
13) at a certain point in time, the reaction was stopped by adding 400 microliters of cold solution (200 ng/mL of tolbutamide in acetonitrile and 200 ng/mL of Labetalol in acetonitrile);
14) the samples were centrifuged at 4000 rpm for 20 minutes to precipitate proteins;
15) 200 microliters of supernatant was transferred into 100 microliters of high performance liquid chromatography water, and shaked for 10 minutes;
16) LC/MS/MS analysis was started.

Experimental Results:

The experimental results are shown in Table 3:

TABLE 3

| CYPs | $IC_{50}$ (nM) Compound 1 |
|---|---|
| CYP1A2 | >50 |
| CYP2C9 | >50 |
| CYP2C19 | >50 |
| CYP2D6 | >50 |
| CYP3A4-M | >50 |

The results showed: the compound of the invention had no significant inhibitory effect on the five main subtypes (CYP1A2, 2C9, 2C19, 2D6, and 3A4) of CYP450 enzyme.

Experimental Example 5: Pharmacokinetic Evaluation of Ocular Administration to Mouse Experimental Purpose:

In order to investigate the eye-to-blood ratio of the in vivo exposure amounts of the compound after ocular administration thereof, LC-MS/MS method was used in this study to determine the exposure amounts of compound 1 in cornea and plasma after the ocular administration of the compound 1 to a mouse, where compound screening and analysis were conducted by using the drug concentration at the same time point as an indicator.

Experimental Methods and Procedures:

C57BL/6 mice, weighing 18-20 g, were randomly divided into 4 groups after 3-5 days of acclimatization, with each group including three mice, and the mice were administered by eye drops at 5 μL for each eye.

The test animals (C57BL/6 mice) were not fasted before administration, but drank water freely before and during the experiment.

About 0.05 mL of blood was collected from saphenous vein at 1 hour and 3 hours following the eye drop administration, anticoagulated with commercial EDTA-K2, and transferred to a centrifuge for centrifugation. After blood sampling from saphenous vein, the corneas were collected under isoflurane anesthesia. At each of the time points, the plasma and corneas of the mice in the same group were pooled for detection.

Treatment of Plasma and Cornea:

Plasma: within 30 minutes the plasma was transferred to be subject to centrifugation at 4° C., 3200 g for 10 minutes, and 20 μL of plasma was taken from each mouse. At each time point, the plasma of the mice in the same group was pooled for detection.

Cornea: the cornea was removed, rinsed twice with pre-cooled normal saline, dried with a paper towel, and put into a 1.5 mL centrifuge tube, weighed with an analytical balance by a peeling method, and finally the body weight was weighed. At each time point, the corneas of the mice in the same group were pooled for detection.

Corneal homogenization method: 1 g of cornea was added to 9 mL of pre-cooled methanol: 15 mM phosphate buffer solution=1:2, an ultrasonic cell disruptor (No. 2 amplitude rod, amplitude 50%, working for 5 s, stopping for 5 s, and ultrasonic treatment for 3 min) was used.

Experimental Results

The experimental results are shown in Table 4:

TABLE 4

Drug concentrations in plasma and corneal and eye-to-blood ratio of compound 1 administered to mouse by eye drop

| | Compound 1 | |
|---|---|---|
| Administration dosage | 0.1 mg/animal | |
| Time point (hour) | 1 hour | 3 hours |
| Drug concentration in corneal (nmol/kg) | 6670 | 2910 |
| Drug concentration in plasma (nM) | 10.4 | 6.8 |
| eye-to-blood ratio | 641 | 427 |

The results showed: the compound of the invention had a high eye-to-blood ratio and was suitable for ocular administration.

Example 6: Pharmacodynamic Test of Mouse Dry Eye Model Induced by Subcutaneous Injection of Scopolamine Experimental Purpose:

Dry eye syndrome, also known as keratoconjunctivitis sicca, is a common ophthalmic disease, which is mostly caused by ocular surface damage or tear film instability due to abnormal tear quality or quantity or dynamics. Dry eye syndrome is often accompanied by symptoms such as itching, dryness and foreign body sensation in the eyes, which have a serious impact on the vision and quality of life of the patients. The purpose of this experiment is to use mouse dry eye model induced by subcutaneous injection of scopolamine, and administer vehicle and compound 1 to the mice through eye drops, to evaluate the improvement of compound 1 on the dry eye model, and to explore the effective dose of the sample for test.

Experimental Methods and Procedures:

12 animals were selected from 20 female C57BL/6J mice and divided into two groups according to the tear test results of each animal before the experiment. There were 6 animals per group.

From the day 1 to day 12 of the experiment, dry eye was induced in mice by subcutaneous injection of scopolamine hydrobromide solution, 4 times/day, 0.1 mL/mouse/time, and the interval between two injections was 3±0.5 h.

From the 1st to the 12th days of the experiment, the animals were given vehicle and 0.5% compound 1 (i.e., 5 mg/mL) by eye drops, 4 times/day, 3 μL/eye/time, and the interval between two administrations was 3±0.5 h. Please be noted that the modeling agent must be administered before eye drop administration (except for inspections on day 7 and day 12).

Before modeling, on day 7 and day 12, all experimental animals were subjected to tear test and corneal fluorescent staining score. The tear test on day 7 and day 12 was performed 30 minutes after the second administration, and the corneal fluorescent staining score was performed 30 minutes after the third administration.

On day 13 of the experiment, the blood samples of the first three animals of the second group were collected at 1 hour after the administration, and then the animals were euthanized, and their eyeballs were collected for collecting the corneas; and the blood samples of the last three animals of the second group were collected 3 hours after the administration, and then the animals were euthanized, and their eyeballs were collected for collecting the corneas.

The day of modeling was designed as the first day of the experiment.

Drug for Delivery:

1) A desired amount of test sample was weighed in a suitable container.

2) A desired volume of 25% (w/v) 2-hydroxypropyl-β-cyclodextrin and 0.2% (v/v) castor oil sterile aqueous solution for injection were added to the above container, and the mixture was stirred until it was visually uniform, and the mixture can be heated and/or sonicated in a 37±2° C. water bath if necessary. The pH was measured and recorded, and the pH was adjusted to be between 7.0 and 7.5 with hydrochloric acid or sodium hydroxide at an appropriate concentration.

3) Under a laminar flow hood, the prepared test sample was filtered into a sterile container with a 0.22 μm GV filter membrane and then packaged for use.

The formulated drug for delivery was stored in a refrigerator at 2° C. to 8° C., protected from light, and used within 2 days. At least 30 minutes before administration, the formulated drug for delivery was removed from the refrigerator to reach room temperature.

Molding Preparation:

1) A desired amount of molding agent was weighed in a suitable container.

2) A desired volume of normal saline was added to the above container and vortexed until the modeling agent was visually dissolved.

3) Under a laminar flow hood, the preparation was filtered with a 0.22 μm GV filter membrane into a sterile container.

The formulated molding preparation was stored in a refrigerator at 2° C. to 8° C., protected from light, and used within 7 days. At least 30 minutes before administration, the formulated molding preparation was removed from the refrigerator to reach room temperature.

Experimental Results:

Tear Secretion Test:

1) About 1 g of phenol red powder was weighed in a suitable container;
2) 20-30 mL of normal saline was added and blended continuously until the solution was saturated;
3) the saturated solution was filtered through a filter paper into another clean container;
4) a cotton thread was put into the filtered reagent and soaked for 5-10 min; and
5) the soaked cotton thread was taken out and dried for later use, and it was used up better within five days.

Before the formal modeling of the experimental animals, there was an adaptive tear test once a day for at least 2 days.

A tear secretion test was performed on both eyes of all the experimental animals at least 30 minutes after the second administration before the modeling on day 7 and day 12, respectively. The left eye of each animal was tested first, and after the tear secretion test on the left eyes of all the experimental animals was completed, the right eye of each animal was tested.

During the test, the phenol red cotton thread was inserted into the lower eyelid near the lateral canthus of the eye to be tested of the mouse using tweezers at one time, while timing for 30 seconds, then the cotton thread was taken out, and the length of the tear trace was measured with a vernier caliper. If the cotton thread fell off during the test, the second measurement was not taken until the animal stood still for 10 minutes or more. The experimental results of the tear secretion on day 7 and day 12 after modeling are shown in FIG. 1.

Corneal Fluorescein Staining

Corneal fluorescent staining was scored for all experimental animals at least 30 minutes after the third administration before modeling on day 7 and day 12, respectively.

Each animal was scored with the left eye first and then the right eye.

First, about 1 μL of 1% sodium fluorescein was instilled on the cornea of the eye to be tested through a pipette, the upper and lower eyelids of the eye to be tested were closed several times, the cornea was rinsed with normal saline several times, and the corneal fluorescence staining was scored for the eye to be tested using a hand-held slit lamp.

Figure 2:
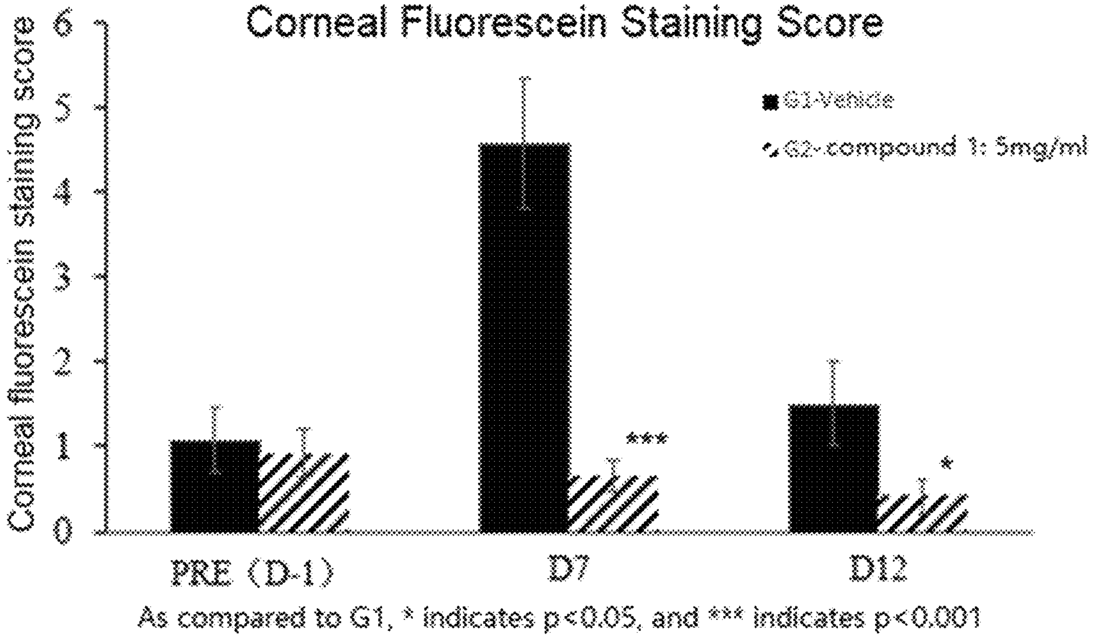
FIG. 2 shows the corneal fluorescence staining scores on the 7th and 12th days after modeling. Note: PRE (D-1) means the day before modeling, D7 means the 7th day, D12 means the 12th day; p means significant difference.

The scoring standard was: the animal cornea was divided into 5 regions, upper, lower, nasal, temporal and central regions, each region was scored from 0-3 points, and the monocular score was the sum of the scores of the five regions. 0 points, no staining; 1 point, light staining, punctate staining in less than 5 areas; 2 points, moderate staining, punctate staining but no plaque staining; 3 points, heavy staining, obvious fluorescent plaques. For comparison between groups, the mean value of the sum of eye scores in each group was used for comparison. The corneal fluorescent staining score results on day 7 and day 12 after modeling are shown in FIG. 2.

The results showed: the compound of the invention exhibited statistically significant efficacy in the scopolamine-induced mouse dry eye model.

What is claimed:

1. A compound represented by formula (I) or a pharmaceutically acceptable salt thereof, (I)

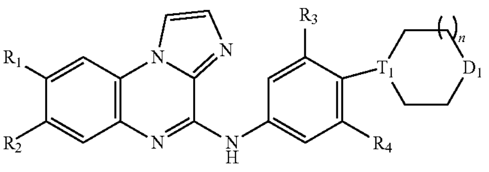

wherein, $R_1$ and $R_2$ are each independently selected from H and pyrazolyl, and $R_1$ and $R_2$ are not both pyrazolyl or H;

$R_3$ and $R_4$ are each independently selected from H, F, Cl, Br, I, OH, $NH_2$, CN, $C_{1-3}$ alkyl and $C_{1-3}$ alkoxy, wherein $C_{1-3}$ alkyl and $C_{1-3}$ alkoxy are optionally substituted with 1, 2 or 3 halogens;

$T_1$ is selected from CH and N;

$D_1$ is selected from —O—, —$C(R_5)(R_6)$—, —$N(R_7)$— and

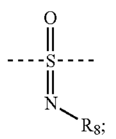

$R_5$ and $R_6$ are each independently selected from OH and $C_{1-3}$ alkyl;

alternatively, $R_5$ and $R_6$ together with a carbon atom to which they are both connected form an oxetanyl group;

$R_7$ is selected from H,

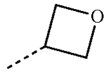

and $C_{1-3}$ alkyl, wherein $C_{1-3}$ alkyl is optionally substituted with 1, 2 or 3 halogens;

$R_8$ is selected from H and —C(=O)—$C_{1-3}$ alkyl; and n is selected from 1 and 2.

2. The compound or the pharmaceutically acceptable salt thereof according to claim 1, wherein $R_1$ is selected from H,

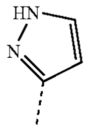
and
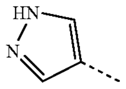
.

3. The compound or the pharmaceutically acceptable salt thereof according to claim 1, wherein $R_2$ is selected from H,

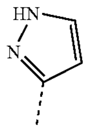
and
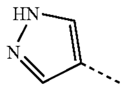
.

4. The compound or the pharmaceutically acceptable salt thereof according to claim 1, wherein $R_3$ is selected from H, F, Cl, Br, I, OH, $NH_2$, CN, $CH_3$ and $CH_3O$.

5. The compound or the pharmaceutically acceptable salt thereof according to claim 1, wherein $R_4$ is selected from H, F, Cl, Br, I, OH, $NH_2$, CN, $CH_3$ and $CH_3O$.

6. The compound or the pharmaceutically acceptable salt thereof according to claim 1, wherein $R_5$ is selected from OH and $CH_3$.

7. The compound or the pharmaceutically acceptable salt thereof according to claim 1, wherein $R_6$ is selected from and $CH_3$.

8. The compound or the pharmaceutically acceptable salt thereof according to claim 1, wherein $R_5$ and $R_6$ together with the carbon atom to which they are both connected form

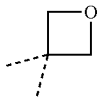

9. The compound or the pharmaceutically acceptable salt thereof according to claim 1, wherein $R_7$ is selected from H, $CH_3$ and

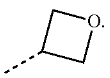

10. The compound or the pharmaceutically acceptable salt thereof according to claim 1, wherein $R_8$ is selected from H and —C(=O)—$CH_3$.

11. The compound or the pharmaceutically acceptable salt thereof according to claim 1, wherein

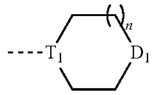

is selected from

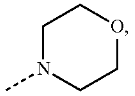
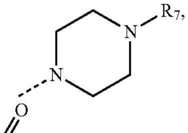
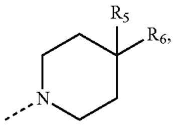
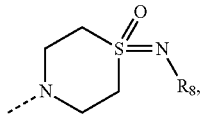
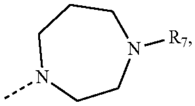
and
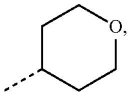

wherein $R_8$, $R_6$, $R_7$ and $R_8$ are defined according to claim 1.

12. The compound or the pharmaceutically acceptable salt thereof according to claim 11, wherein

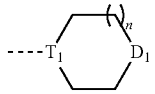

is selected from

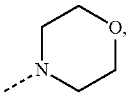
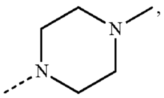
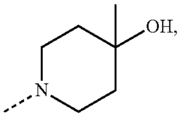
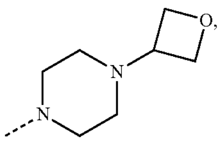
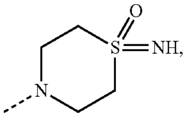
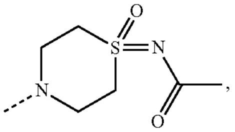
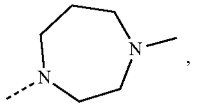
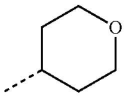
and
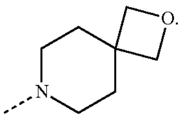

13. The compound or the pharmaceutically acceptable salt thereof according to claim 1, wherein the compound is selected from:

(I-1)
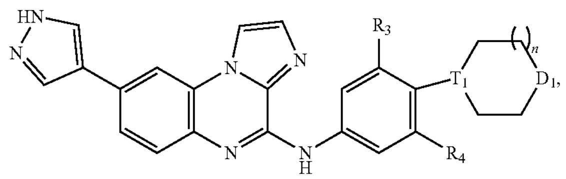
(I-2)
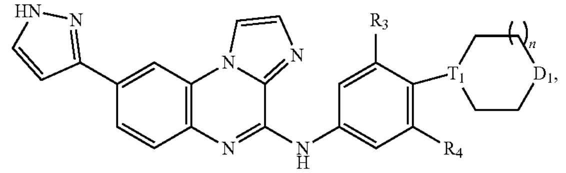
(I-3)
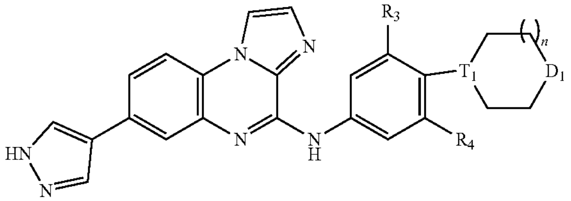
and
(I-4)
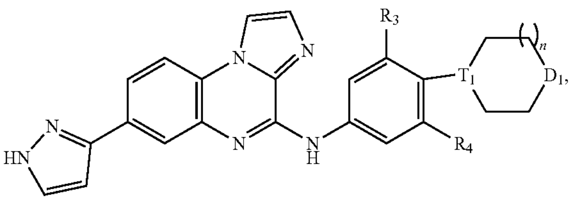
wherein, $R_3$, $R_4$, $T_1$, $D_1$ and n are defined according to claim 1.
14. A compound represented by any of the following formula or a pharmaceutically acceptable salt thereof,
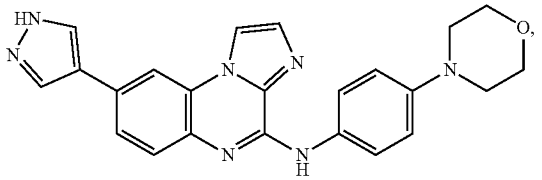
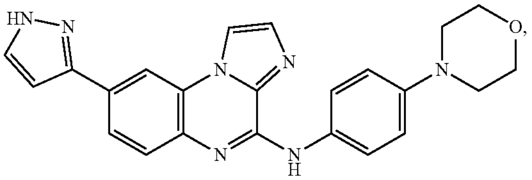
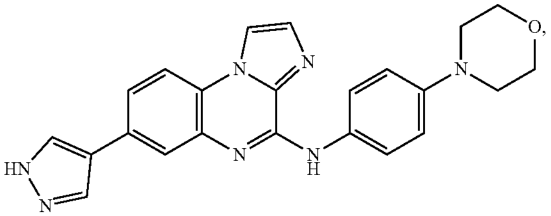
-continued
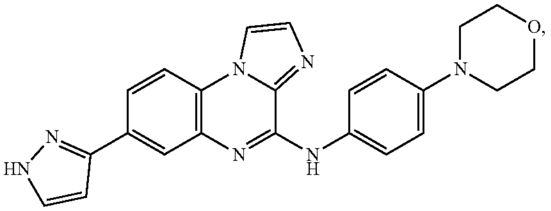
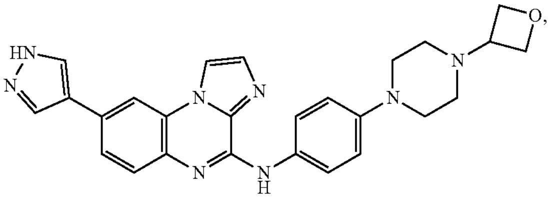
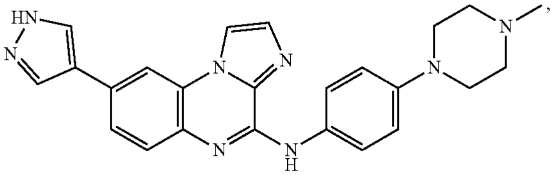
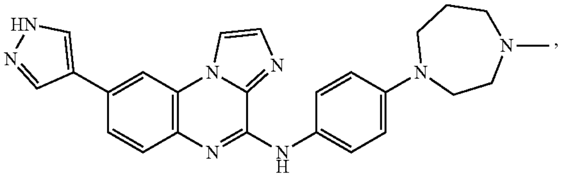
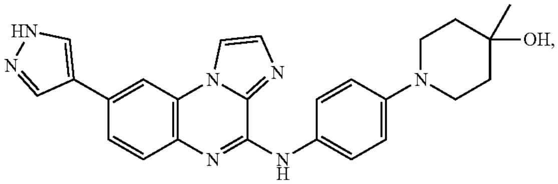
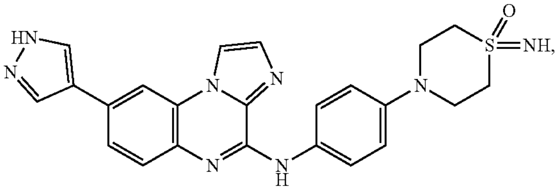
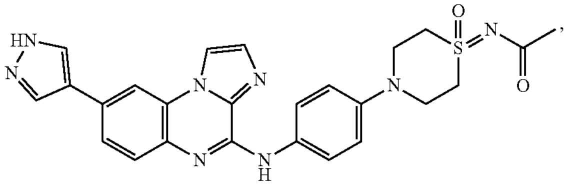
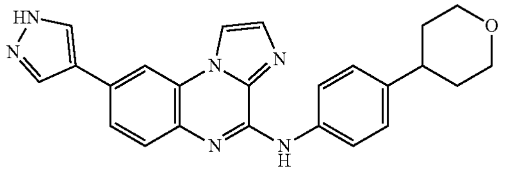
and
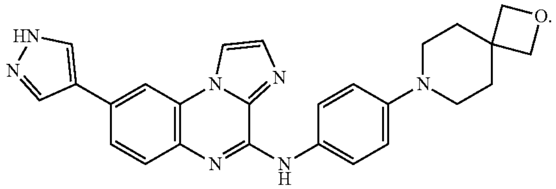

15. A method for preparing a compound of formula 1, comprising:

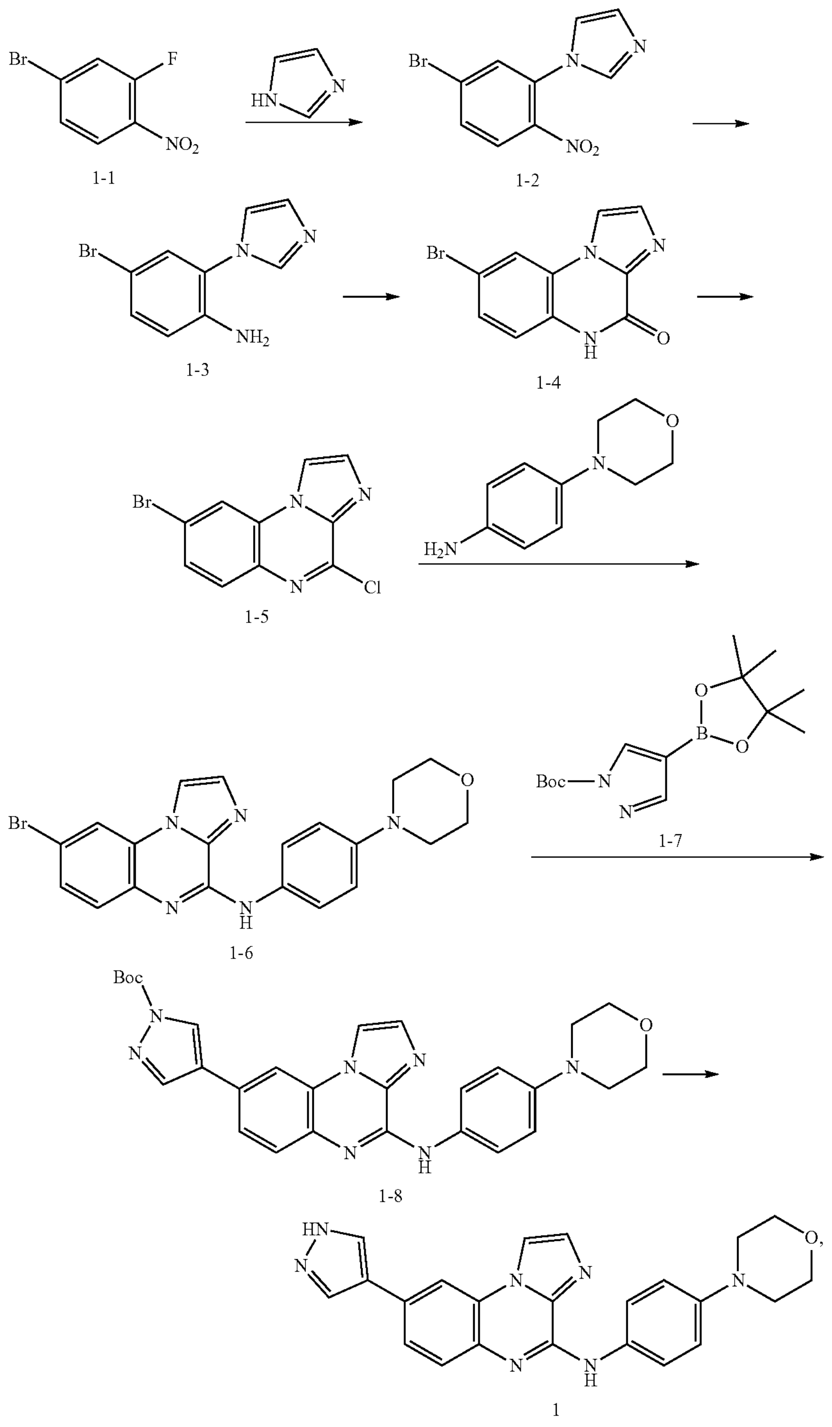

step 1 of synthesizing a compound of formula 1-2 by reacting a compound of formula 1-1 with imidazole;

step 2 of synthesizing a compound of formula 1-3 from the compound of formula 1-2; step 3 of synthesizing a compound of formula 1-4 from the compound of formula 1-3; step 4 of synthesizing a compound of formula 1-5 from the compound of formula 1-4; step 5 of synthesizing a compound of formula 1-6 by reacting the compound of formula 1-5 with 4-morpholinoaniline;

step 6 of synthesizing a compound of formula 1-8 by reacting the compound of formula 1-6 with a compound of formula 1-7; and step 7 of synthesizing the compound of formula 1 from the compound of formula 1-8.

16. The method according to claim 15, wherein:

step 1 comprises adding imidazole and DIEA to a solution of the compound of formula 1-1 in acetonitrile, stirring the reaction solution at 90° C. for 16 hours, concentrating the reaction solution, adding water, and extracting the mixture twice with ethyl acetate, and then combining, drying, filtering and concentrating the organic phases from the extraction to obtain the compound of formula 1-2;

step 2 comprises adding stannous chloride dihydrate to a solution of the compound of formula 1-2 in ethanol, stirring the reaction solution at 90° C. for 3 hours, concentrating the reaction solution under reduced pressure, adding ethyl acetate, neutralizing the solution with saturated sodium bicarbonate solution to pH=9 to precipitate a white solid, filtering off the precipitated solid, adding to the filtrate with water, extracting the filtrate twice with ethyl acetate, and combining, washing with saturated brine, drying over anhydrous sodium sulfate, filtering and concentrating the organic phases from the extraction to obtain the compound of formula 1-3;

step 3 comprises adding CDI to the compound of formula 1-3 in dichlorobenzene under the protection of nitrogen, stirring the reaction solution at 190 degrees Celsius for 2 hours, cooling the reaction solution to room temperature, filtering the reaction solution, and drying the filter cake from the filtering to obtain the compound of formula 1-4;

step 4 comprises adding the compound of formula 1-4 and dimethylaniline to phosphorus oxychloride, stirring the reaction solution at 110 degrees Celsius for 1.5 hours, concentrating the reaction solution, adjusting the pH to 9 with saturated aqueous sodium bicarbonate solution to precipitate a solid, filtering the precipitated solid, and drying the filter cake from the filtering to obtain the compound of formula 1-5;

step 5 comprises adding 4-morpholinoaniline and DIEA to the compound of formula 1-5 in isopropanol, stirring the reaction solution at 100 degrees Celsius for 32 hours, filtering the reaction solution, and drying the filter cake from the filtering to obtain the compound of formula 1-6;

step 6 comprises adding the compound of formula 1-6, the compound of formula 1-7, potassium carbonate and $Pd(dppf)Cl_2$ to 1,4-dioxane and water, stirring the reaction solution at 80° C. for 4 hours under the protection of nitrogen, adding the reaction solution with water, extracting the reaction solution twice with ethyl acetate, and combining, washing twice with saturated brine, drying over anhydrous sodium sulfate, filtering and concentrating the organic phases from the extraction to obtain the compound of formula 1-8; and step 7 comprises adding trifluoroacetic acid to a solution of the compound of formula 1-8 in dichloromethane, stirring the reaction solution at 25 degrees Celsius for 1 hour, adjusting the pH of the reaction solution to 8 with aqueous ammonia, adding water, and extracting the reaction solution twice with dichloromethane, then combining, washing twice with saturated brine, drying over anhydrous sodium sulfate, filtering and concentrating the organic phases from the extraction, adding acetone to the crude product, and heating to 60 degrees Celsius, stirring for 0.5 hours, cooling to room temperature, filtering, and vacuum drying the crude product to obtain the compound of formula 1.

17. A method for preparing a compound of formula 2, comprising:

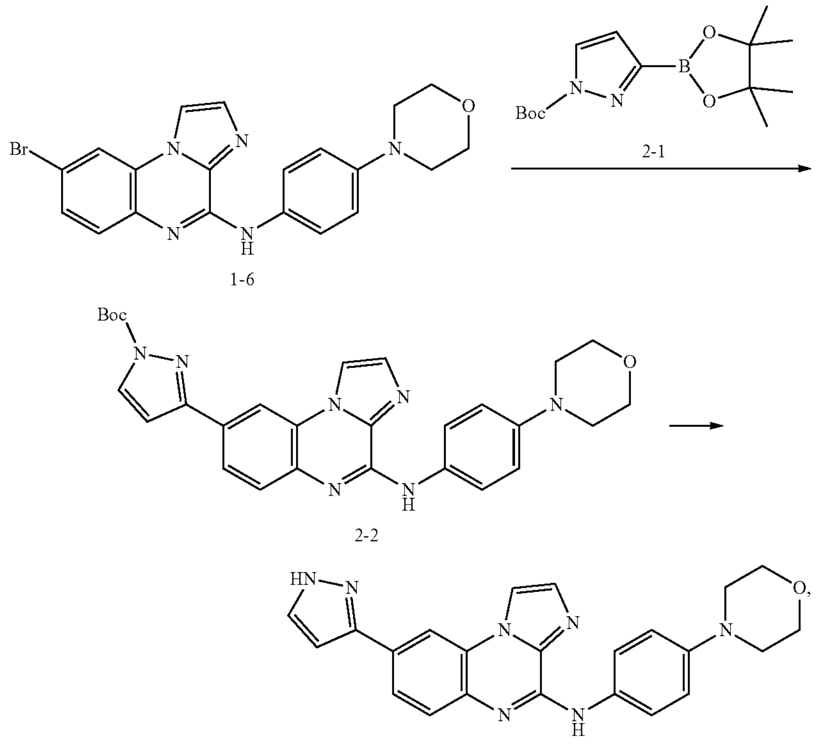

1-6

2-1

2-2

2 step 1 of synthesizing a compound of formula 2-2 by reacting a compound of formula 1-6 with a compound of formula 2-1; and step 2 of synthesizing a compound of formula 2 from the compound of formula 2-2.

18. The method according to claim 17, wherein:

step 1 comprises adding the compound of formula 1-6, the compound of formula 2-1, potassium carbonate and Pd(dppf)$Cl_2$ to 1,4-dioxane and water, stirring the reaction solution at 80° C. for 4 hours under the protection of nitrogen, adding water to the reaction solution, and extracting the mixture twice with ethyl acetate, and then combining, washing twice with saturated brine, drying over anhydrous sodium sulfate, filtering and concentrating the organic phases from the extraction to obtain the compound of formula 2-2; and step 2 comprises adding trifluoroacetic acid to a solution of the compound of formula 2-2 in dichloromethane; stirring the reaction solution at 25 degrees Celsius for 2 hours, adjusting the pH of the reaction solution to 8 with aqueous ammonia, adding water, extracting the solution twice with dichloromethane, then combining, washing twice with saturated brine, drying over anhydrous sodium sulfate, filtering and concentrating the organic phases from the extraction, and separating and purifying the crude product by high performance liquid chromatography to obtain the compound of formula 2.

19. A method for preparing a compound of formula 3, comprising:

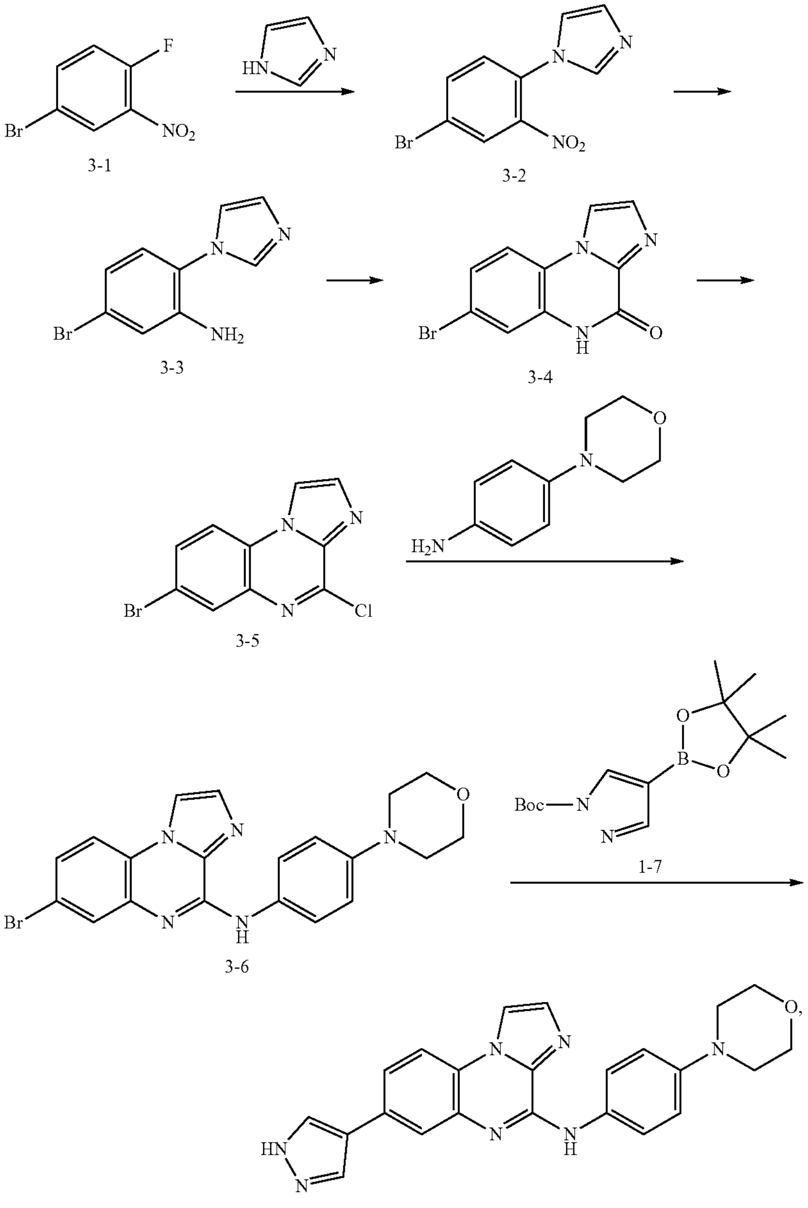

3-1

3-2

3-3

3-4

3-5

3-6

1-7

3 step 1 of synthesizing a compound of formula 3-2 by reacting a compound of formula 3-1 with imidazole;

step 2 of synthesizing a compound of formula 3-3 from the compound of formula 3-2; step 3 of synthesizing a compound of formula 3-4 from the compound of formula 3-3; step 4 of synthesizing a compound of formula 3-5 from the compound of formula 3-4; step 5 of synthesizing a compound of formula 3-6 by reacting the compound of formula 3-5 with 4-morpholinoaniline; and step 6 of synthesizing the compound of formula 3 by reacting the compound of formula 3-6 with a compound of formula 1-7.

20. The method according to claim 1, wherein:

step 1 comprises adding imidazole and DIEA to a solution of the compound of formula 3-1 in acetonitrile, stirring the reaction solution at 90° C. for 16 hours, concentrating the reaction solution, adding water, extracting the mixture twice with ethyl acetate, and then combining, washing once with saturated brine, drying over anhydrous sodium sulfate, filtering and concentrating the organic phases from the extraction to obtain the compound of formula 3-2;

step 2 comprises adding stannous chloride dihydrate to a solution of the compound of formula 3-2 in ethanol, stirring the reaction solution at 80° C. for 3 hours, concentrating the reaction solution under reduced pressure, adding ethyl acetate, neutralizing the solution with saturated sodium bicarbonate solution to pH=9 to precipitate a white solid, filtering off the precipitated solid, adding water to the filtrate, extracting the filtrate twice with ethyl acetate, and combining, washing with saturated brine, drying over anhydrous sodium sulfate, filtering and concentrating the organic phases from the extraction to obtain the compound of formula 3-3;

step 3 comprises adding CDI to the compound of formula 3-3 in dichlorobenzene under the protection of nitrogen, stirring the reaction solution at 190 degrees Celsius for 2 hours, cooling the reaction solution to room temperature, filtering the reaction solution, and drying the filter cake from the filtering to obtain the compound of formula 3-4;

step 4 comprises adding the compound of formula 3-4 and dimethylaniline to phosphorus oxychloride, stirring the reaction solution at 110 degrees Celsius for 1.5 hours, concentrating the reaction solution, adjusting the pH to 9 with saturated aqueous sodium bicarbonate solution to precipitate a solid, filtering the precipitated solid, drying the filter cake from the filtering, and purifying the filter cake by column chromatography to obtain the compound of formula 3-5;

step 5 comprises adding 4-morpholinoaniline and DIEA to the compound of formula 3-5 in isopropanol, stirring the reaction solution at 100 degrees Celsius for 16 hours, filtering the reaction solution, and drying the filter cake from the filtering to obtain the compound of formula 3-6; and step 6 comprises adding the compound of formula 3-6, the compound of formula 1-7, potassium carbonate and Pd(dppf)$Cl_2$ to 1,4-dioxane and water, stirring the reaction solution at 80° C. under the protection of nitrogen, adding water to the reaction solution, extracting the reaction solution twice with ethyl acetate, then combining, washing twice with saturated brine, drying over anhydrous sodium sulfate, filtering and concentrating the organic phases from the extraction to obtain a crude product, and separating and purifying the crude product by high performance liquid chromatography to obtain the compound of formula 3.

21. A method for preparing a compound of formula 4, comprising synthesizing the compound of formula 4 by reacting a compound of formula 3-6 with a compound of formula 2-1,

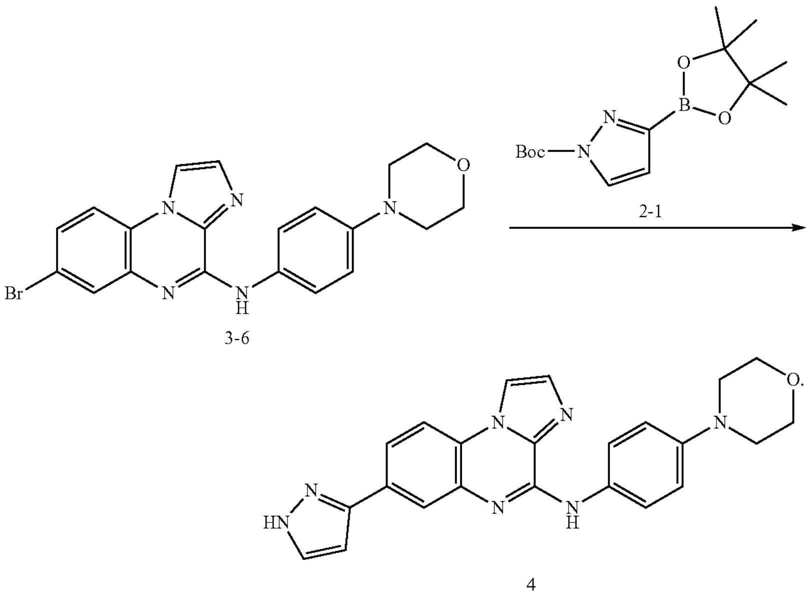

3-6

2-1

4

22. The method according to claim 21, comprising adding the compound of formula 3-6, the compound of formula 2-1, potassium carbonate and Pd(dppf)$Cl_2$ to 1,4-dioxane and water, stirring the reaction solution at 90° C. for 4 hours under the protection of nitrogen, adding water to the reaction solution, and extracting the mixture twice with ethyl acetate, then combining, washing twice with saturated brine, drying over anhydrous sodium sulfate, filtering and concentrating the organic phases from the extraction to obtain a crude product, and separating and purifying the crude product by high performance liquid chromatography to obtain the compound of formula 4.

23. A method for preparing a compound of formula 5, comprising:
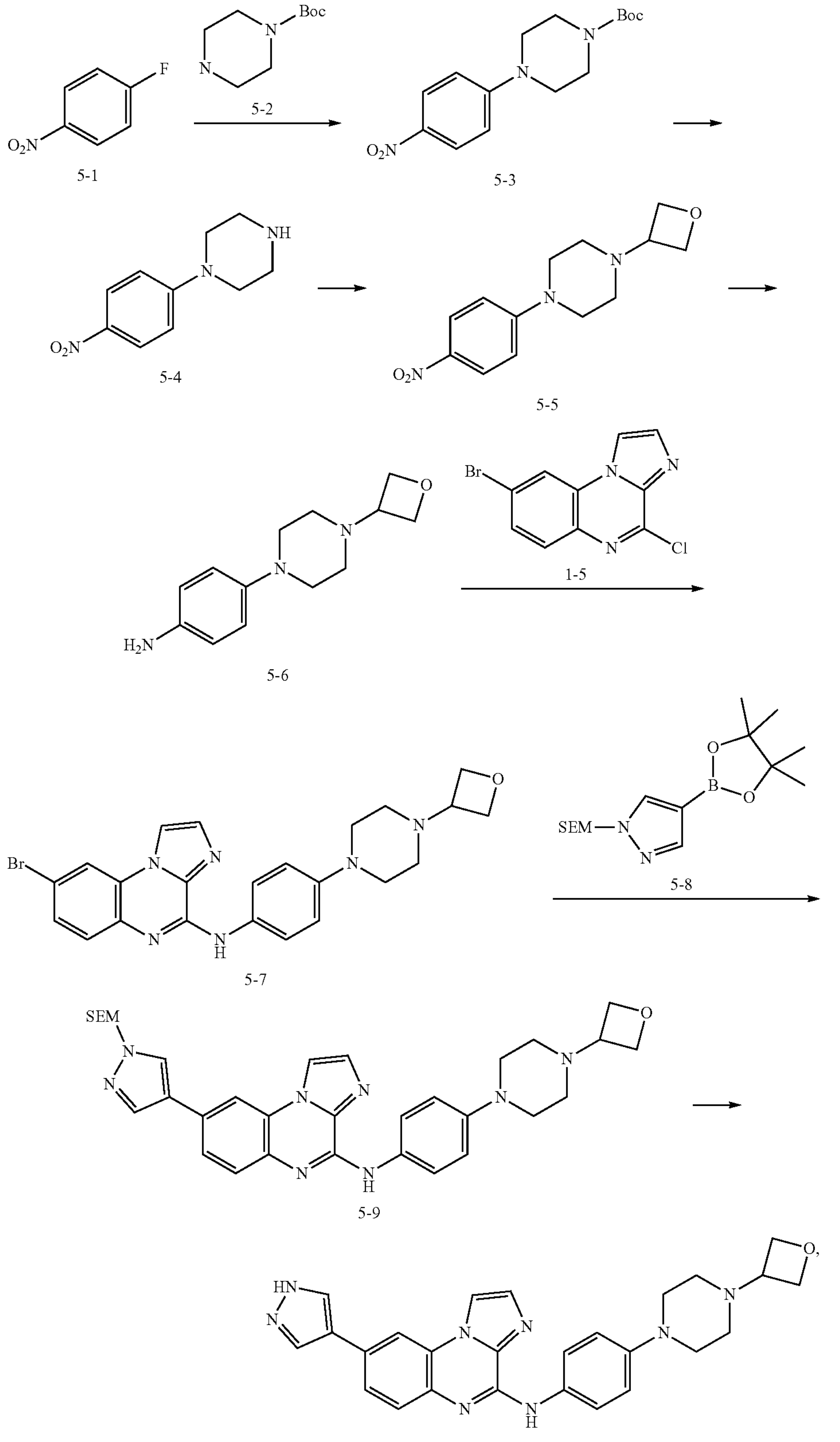
5-1 5-2 5-3
5-4 5-5
5-6 1-5
5-7 5-8
5-9
5 step 1 of synthesizing a compound of formula 5-3 by reacting a compound of formula 5-1 with a compound of formula 5-2;

step 2 of synthesizing a compound of formula 5-4 from the compound of formula 5-3; step 3 of synthesizing a compound of formula 5-5 from the compound of formula 5-4; step 4 of synthesizing a compound of formula 5-6 from the compound of formula 5-5; step 5 of synthesizing a compound of formula 5-7 by reacting the compound of formula 5-5 with the compound of formula 5-6;

step 6 of synthesizing a compound of formula 5-9 by reacting the compound of formula 5-7 with a compound of formula 5-8; and step 7 of synthesizing the compound of formula 5 from the compound of formula 5-9.

24. The method according to claim 23, wherein:

step 1 comprises adding potassium carbonate and the compound of formula 5-2 to a solution of the compound of formula 5-1 in DMSO, stirring the reaction solution at 80 degrees Celsius for 16 hours, concentrating the reaction solution, adding water, and extracting the mixture three times with ethyl acetate, and then combining, drying, filtering and concentrating the organic phases from the extraction to obtain the compound of formula 5-3;

step 2 comprises adding the compound of formula 5-3 in small batches to a dioxane hydrochloride solution, stirring the mixture at room temperature for 16 hours, and concentrating the reaction solution under reduced pressure to obtain the compound of formula 5-4;

step 3 comprises adding sodium acetate to a solution of the compound of formula 5-4 in ethanol under the protection of nitrogen, stirring the mixture at room temperature for 1 hour before adding oxetanone and zinc chloride, then stirring the mixture at room temperature for 2 hours before adding sodium cyanoborohydride, stirring the mixture at 40 degrees Celsius for 16 hours, then adding water to the reaction solution, extracting the mixture three times with ethyl acetate, and then combining, washing twice with saturated brine, drying over anhydrous sodium sulfate, filtering and concentrating the organic phases from the extraction to obtain the compound of formula 5-5;

step 4 comprises adding palladium carbon to a solution of the compound of formula 5-5 in methanol under the protection of nitrogen, then replacing the nitrogen with hydrogen by a hydrogen balloon three times, stirring the reaction at room temperature for 16 hours under hydrogen, then filtering the reaction solution, and concentrating and drying the filtrate to obtain the compound of formula 5-6;

step 5 comprises adding the compound of formula 5-6 and DIEA to a solution of the compound of formula 1-5 in isopropanol, stirring the reaction solution at 100 degrees Celsius for 16 hours, cooling the reaction solution to room temperature, filtering the reaction solution, and drying the filter cake from the filtering to obtain the compound of formula 5-7;

step 6 comprises adding the compound of formula 5-7, the compound of formula 5-8, potassium carbonate and Pd(dppf)$Cl_2$ to 1,4-dioxane and water, stirring the reaction solution at 100° C. for 16 hours under the protection of nitrogen, adding water to the reaction solution, extracting the mixture three times with ethyl acetate, and combining, washing twice with saturated brine, drying over anhydrous sodium sulfate, filtering and concentrating the organic phases from the extraction to obtain the compound of formula 5-9; and step 7 comprises adding tetrabutylammonium fluoride and ethylenediamine to a solution of the compound of formula 5-9 in tetrahydrofuran, stirring the reaction solution at 75 degrees Celsius for 16 hours, adjusting the pH of the reaction solution to 8 with sodium hydroxide solution, adding water, extracting the solution twice with dichloromethane, then combining, washing twice with saturated brine, drying over anhydrous sodium sulfate, filtering and concentrating the organic phases from the extraction to obtain a crude product, and separating the crude product by silica gel column chromatography to obtain the compound of formula 5.

25. A method for preparing a compound of formula 6, comprising:

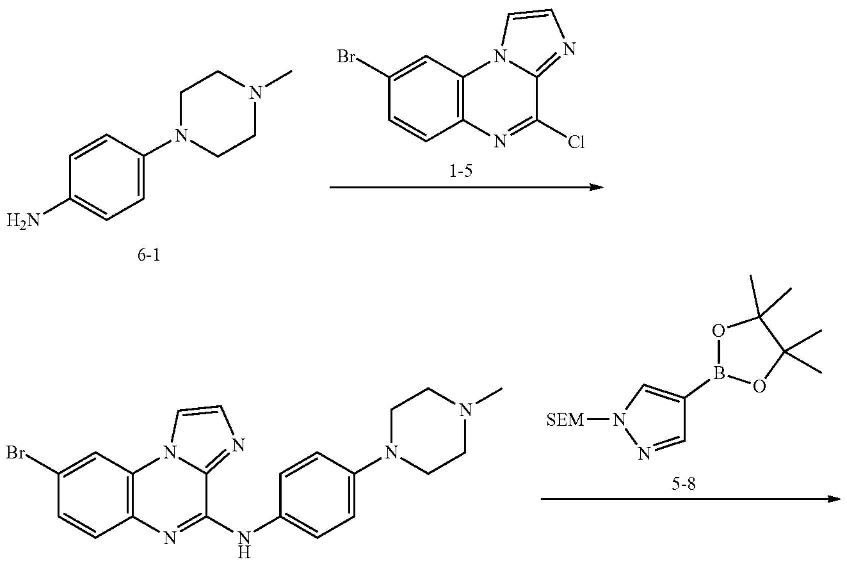

6-1

6-2

-continued

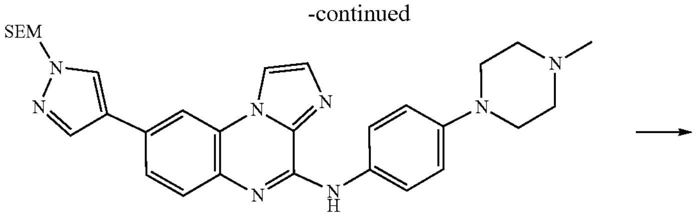

6-3

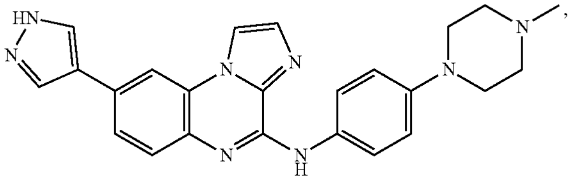

6 step 1 of synthesizing a compound of formula 6-2 by reacting a compound of formula 6-1 with a compound of formula 1-5;

step 2 of synthesizing a compound of formula 6-3 by reacting the compound of formula 6-2 with a compound of formula 5-8; and step 3 of synthesizing the compound of formula 6 from the compound of formula 6-3.

26. The method according to claim 25, wherein:

step 1 comprises adding the compound of formula 6-1 and DIEA to a solution of compound of formula 1-5 in dimethyl sulfoxide, stirring the reaction solution at 120 degrees Celsius for 16 hours, cooling the reaction solution to room temperature, then adding water to precipitate a solid, filtering the mixture, slurrying the filter cake from the filtering with isopropanol, and filtering and drying the slurry to obtain the compound of formula 6-2;

step 2 comprises adding the compound of formula 6-2, the compound of formula 5-8, potassium carbonate and $Pd(dppf)Cl_2$ to 1,4-dioxane and water, then stirring the reaction solution at 100° C. for 16 hours under the protection of nitrogen, adding water to the reaction solution, extracting the solution three times with ethyl acetate, combining, washing twice with saturated brine, drying over anhydrous sodium sulfate, filtering and concentrating the organic phases from the extraction to obtain a crude product, and separating the crude product by silica gel column chromatography to obtain the compound of formula 6-3; and step 3 comprises adding the compound of formula 6-3 to dioxane hydrochloride, stirring the reaction solution at 25 degrees Celsius for 16 hours, adjusting the pH of the reaction solution to 8 with aqueous sodium hydroxide solution, adding water, extracting the solution twice with dichloromethane, then combining, washing twice with saturated brine, drying over anhydrous sodium sulfate, filtering and concentrating the organic phases from the extraction to obtain a crude product, adding acetone to the crude product, stirring the mixture for 0.5 hours, filtering the mixture, and drying the filter cake from the filtering to obtain the compound of formula 6.

27. A method for preparing a compound of formula 7, comprising:

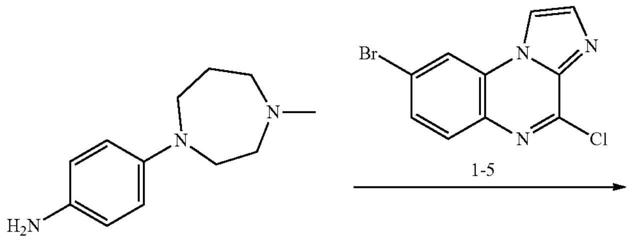

1-5

7-1

-continued

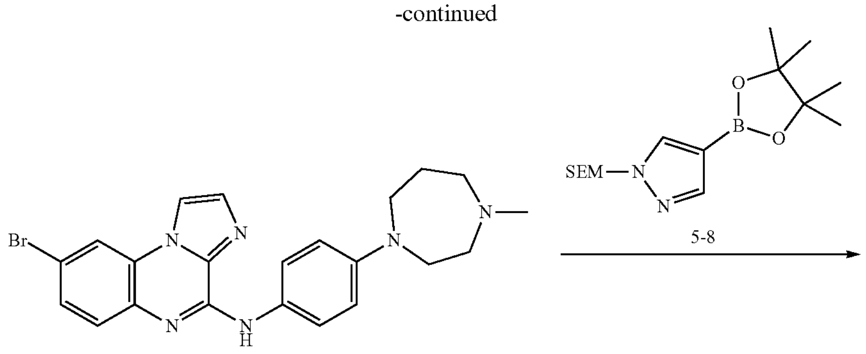

5-8

7-2

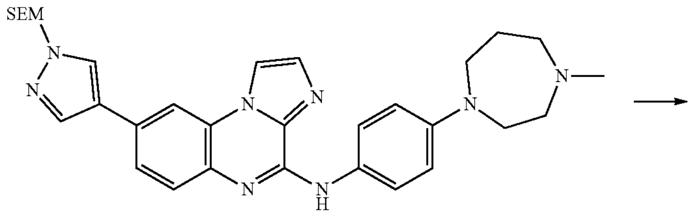

7-3

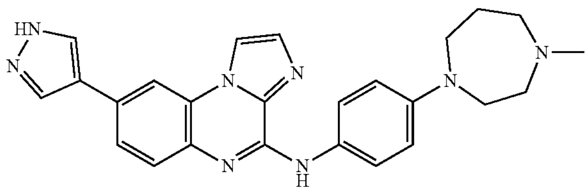

,

7 step 1 of synthesizing a compound of formula 7-2 by reacting a compound of formula 7-1 with a compound of formula 1-5;

step 2 of synthesizing a compound of formula 7-3 by reacting the compound of formula 7-2 with a compound of formula 5-8; and step 3 of synthesizing the compound of formula 7 from the compound of formula 7-3.

28. The method according to claim 27, wherein:

step 1 comprises adding the compound of formula 7-1 and DIEA to a solution of compound of formula 1-5 in dimethyl sulfoxide, stirring the reaction solution at 120 degrees Celsius for 16 hours, cooling the reaction solution to room temperature, then adding water to precipitate a solid, filtering the mixture, slurrying the filter cake from the filtering with isopropanol, and filtering and drying the slurry to obtain the compound of formula 7-2;

step 2 comprises adding the compound of formula 7-2, the compound of formula 5-8, potassium carbonate and $Pd(dppf)Cl_2$ to 1,4-dioxane and water, then stirring the reaction solution at 100° C. for 16 hours under the protection of nitrogen, adding water to the reaction solution, extracting the solution three times with ethyl acetate, combining, washing twice with saturated brine, drying over anhydrous sodium sulfate, filtering and concentrating the organic phases from the extraction to obtain a crude product, and separating the crude product by silica gel column chromatography to obtain the compound of formula 7-3; and step 3 comprises adding the compound of formula 7-3 to dioxane hydrochloride, stirring the reaction solution at 25 degrees Celsius for 16 hours, adjusting the pH of the reaction solution to 8 with aqueous sodium hydroxide solution, adding water, extracting the solution twice with dichloromethane, then combining, washing twice with saturated brine, drying over anhydrous sodium sulfate, filtering and concentrating the organic phases from the extraction to obtain a crude product, and separating the crude product by silica gel column chromatography to obtain the compound of formula 7.

29. A method for preparing a compound of formula 8, comprising:
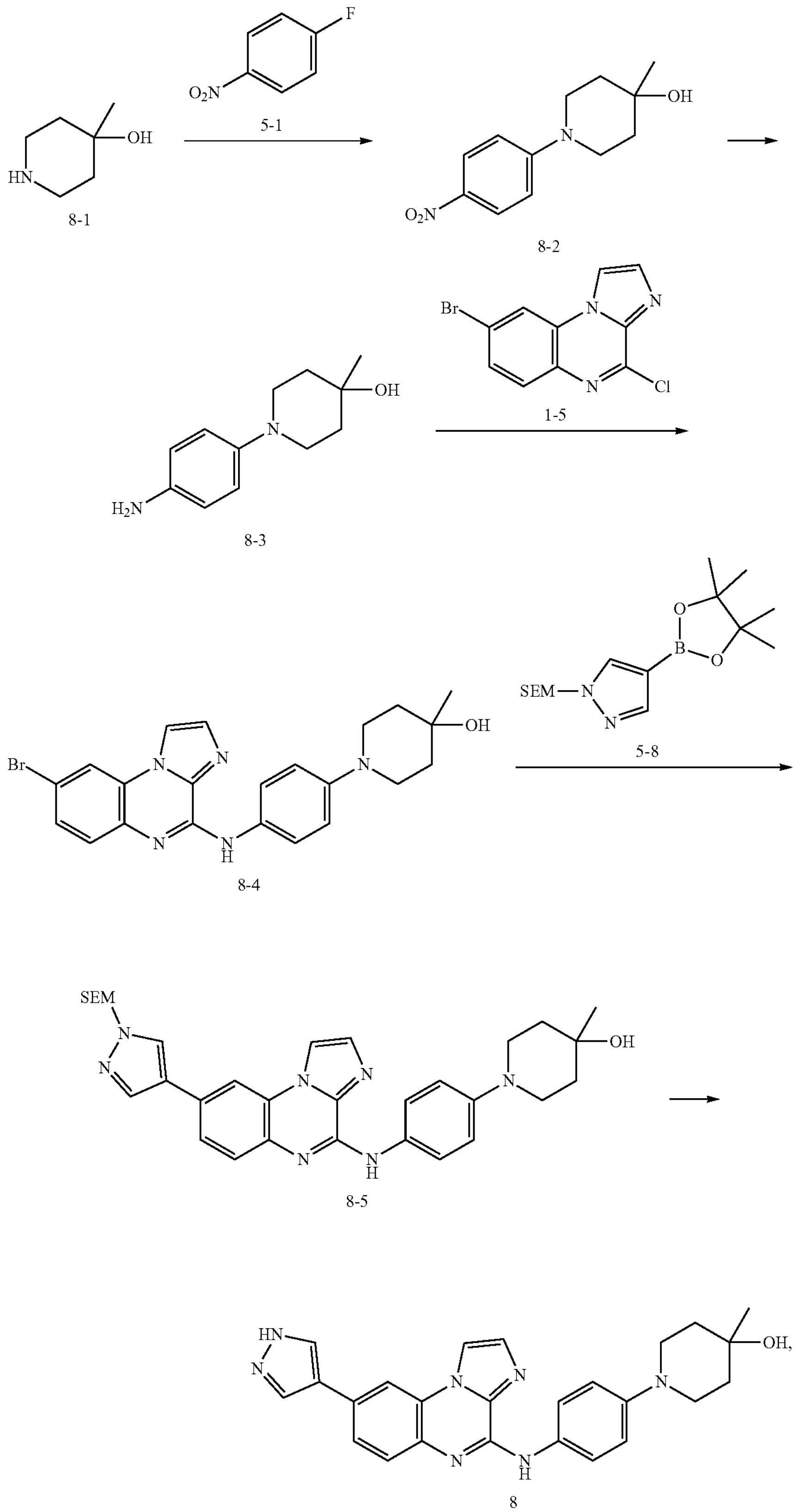
8-1
5-1
8-2
1-5
8-3
5-8
8-4
8-5
8 step 1 of synthesizing a compound of formula 8-2 by reacting a compound of formula 8-1 with a compound of formula 5-1;

step 2 of synthesizing a compound of formula 8-3 from the compound of formula 8-2; step 3 of synthesizing a compound of formula 8-4 by reacting the compound of formula 8-3 with a compound of formula 1-5;

step 4 of synthesizing a compound of formula 8-5 by reacting the compound of formula 8-4 with a compound of formula 5-8; and step 5 of synthesizing the compound of formula 8 from the compound of formula 8-5.

30. The method according to claim 29, wherein:

step 1 comprises adding potassium carbonate and the compound of formula 8-1 to a solution of the compound of formula 5-1 in DMSO, stirring the reaction solution at 100 degrees Celsius for 16 hours, concentrating the reaction solution, adding water, and extracting the mixture three times with ethyl acetate, and combining, drying, filtering and concentrating the organic phases from the extraction to obtain the compound of formula 8-2;

step 2 comprises adding ammonium chloride and iron powder to a solution of the compound of formula 8-2 in ethanol and water under the protection of nitrogen, stirring the reaction solution at 100 degrees Celsius for 16 hours, then filtering the reaction solution, adding water to the filtrate, extracting the mixture three times with ethyl acetate, and combining, drying, filtering and concentrating the organic phases from the extraction to obtain the compound of formula 8-3;

step 3 comprises adding the compound of formula 8-3 and DIEA to a solution of the compound of formula 1-5 in dimethyl sulfoxide, stirring the reaction solution at 120 degrees Celsius for 16 hours, then cooling the reaction solution to room temperature, adding water to precipitate a solid, filtering the mixture, slurrying the filter cake from the filtering with isopropanol, and filtering and drying the slurry to obtain the compound of formula 8-4;

step 4 comprises adding the compound of formula 8-4, the compound of formula 5-8, potassium carbonate and Pd(dppf)$Cl_2$ to 1,4-dioxane and water, then stirring the reaction solution at 100° C. for 16 hours under the protection of nitrogen, adding water to the reaction solution, extracting the solution three times with dichloromethane, combining, washing twice with saturated brine, drying over anhydrous sodium sulfate, filtering and concentrating the organic phases from the extraction to obtain a crude product, and separating the crude product by silica gel column chromatography to obtain the compound of formula 8-5; and step 5 comprises adding the compound of formula 8-5 to dioxane hydrochloride, stirring the reaction solution at 25 degrees Celsius for 16 hours, then adjusting the pH of the reaction solution to 8 with aqueous sodium hydroxide solution, adding water, extracting the solution twice with dichloromethane, then combining, washing twice with saturated brine, drying over anhydrous sodium sulfate, filtering and concentrating the organic phases from the extraction to obtain a crude product, and separating the crude product by silica gel column chromatography to obtain the compound of formula 8.

31. A method for preparing a compound of formula 9, comprising:

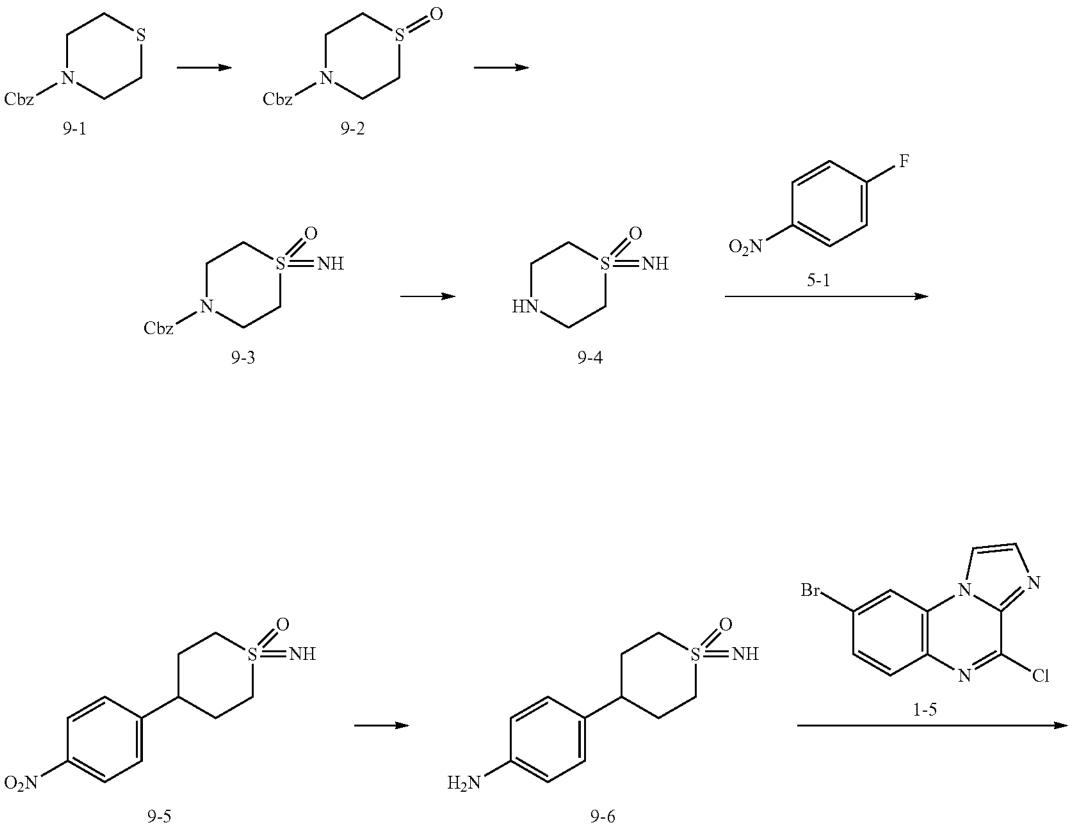

9-1
9-2
9-3
9-4
9-5
9-6

-continued

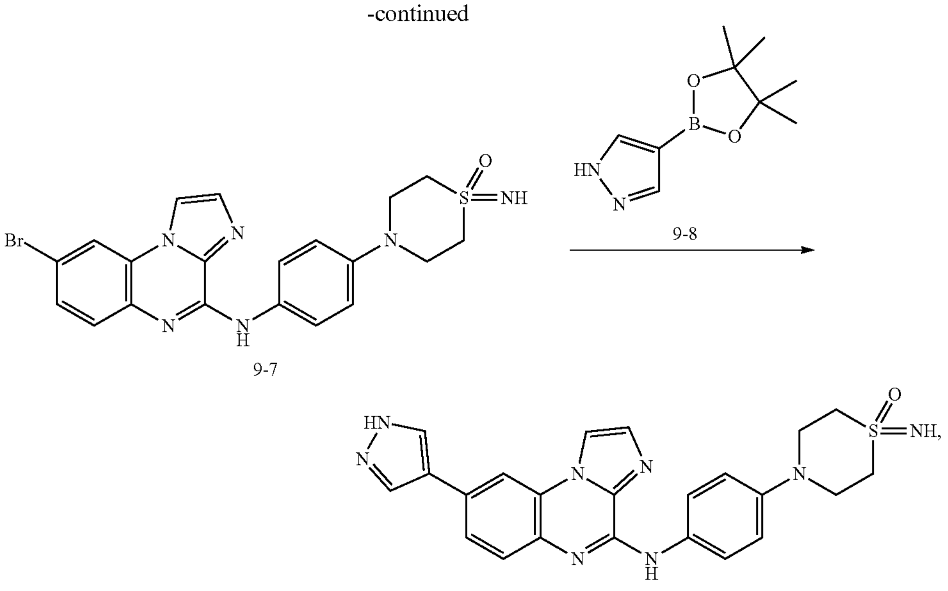

9-7 9-8 9 step 1 of synthesizing a compound of formula 9-2 from a compound of formula 9-1;

step 2 of synthesizing a compound of formula 9-3 from the compound of formula 9-2; step 3 of synthesizing a compound of formula 9-4 from the compound of formula 9-3; step 4 of synthesizing a compound of formula 9-5 by reacting the compound of formula 9-4 with a compound of formula 5-1;

step 5 of synthesizing a compound of formula 9-6 from the compound of formula 9-5;

step 6 of synthesizing a compound of formula 9-7 by reacting the compound of formula 9-6 with a compound of formula 1-5; and step 7 of synthesizing the compound of formula 9 by reacting the compound of formula 9-7 with a compound of formula 9-8.

32. The method according to claim 31, wherein:

step 1 comprises cooling a solution of the compound of formula 9-1 in methanol and water to 0 degrees Celsius, adding sodium periodate to the solution, stirring the reaction solution at 20 degrees Celsius for 16 hours, filtering the reaction solution, washing the filter cake from the filtering three times with ethyl acetate, and combining, drying over anhydrous sodium sulfate, filtering and concentrating the organic phases from the washing to obtain the compound of formula 9-2;

step 2 comprises adding trifluoroacetamide, rhodium acetate, magnesium oxide diacetoxyiodobenzene and potassium carbonate to a solution of the compound of formula 9-2 in dichloromethane under the protection of nitrogen, stirring the reaction solution at 20 degrees Celsius for 16 hours, then filtering the reaction solution, washing the filter cake from the filtering three times with dichloromethane, combining, drying over anhydrous sodium sulfate, filtering and concentrating the organic phases from the washing to obtain a crude product, and separating and purifying the crude product by silica gel column chromatography to obtain the compound of formula 9-3;

step 3 comprises adding the compound of formula 9-3 to a solution of hydrobromic acid in acetic acid, stirring the reaction solution at 20 degrees Celsius for 10 hours, then adjusting the pH of the reaction solution to 8 with aqueous sodium hydroxide solution, adding water, extracting the solution three times with dichloromethane, and combining, washing twice with saturated brine, drying over anhydrous sodium sulfate, filtering and concentrating the organic phases from the extraction to obtain the compound of formula 9-4;

step 4 comprises adding potassium carbonate and the compound of formula 9-4 to a solution of the compound of formula 5-1 in DMSO, stirring the reaction solution at 100 degrees Celsius for 16 hours, concentrating the reaction solution, adding water, and extracting the mixture three times with ethyl acetate, and combining, drying over anhydrous sodium sulfate, filtering and concentrating the organic phases from the extraction to obtain the compound of formula 9-5, step 5 comprises adding ammonium chloride and iron powder to a solution of the compound of formula 9-5 in ethanol and water under the protection of nitrogen, stirring the reaction solution at 90 degrees Celsius 1 hour, then filtering the reaction solution, adding water to the filtrate, extracting the mixture three times with ethyl acetate, and combining, drying, filtering and concentrating the organic phases from the extraction to obtain the compound of formula 9-6;

step 6 comprises adding the compound of formula 9-6 and DIEA to a solution of the compound of formula 1-5 in dimethyl sulfoxide, stirring the reaction solution at 120 degrees Celsius for 16 hours, then cooling the reaction solution to room temperature, adding water to precipitate a solid, filtering the mixture, slurrying the filter cake from the filtering with isopropanol, and filtering and drying the slurry to obtain the compound of formula 9-7; and step 7 comprises adding the compound of formula 9-7, the compound of formula 9-8 potassium carbonate and $Pd(dppf)Cl_2$ to 1,4-dioxane and water, then stirring the reaction solution at 100° C. for 16 hours under the protection of nitrogen, adding water to the reaction solution, extracting the solution three times with dichloromethane, combining, washing twice with saturated brine, drying over anhydrous sodium sulfate, filtering and concentrating the organic phases from the extraction to obtain a crude product, and separating and purifying the crude product by silica gel column chromatography to obtain the compound of formula 9.

33. A method for preparing a compound of formula 10, comprising:

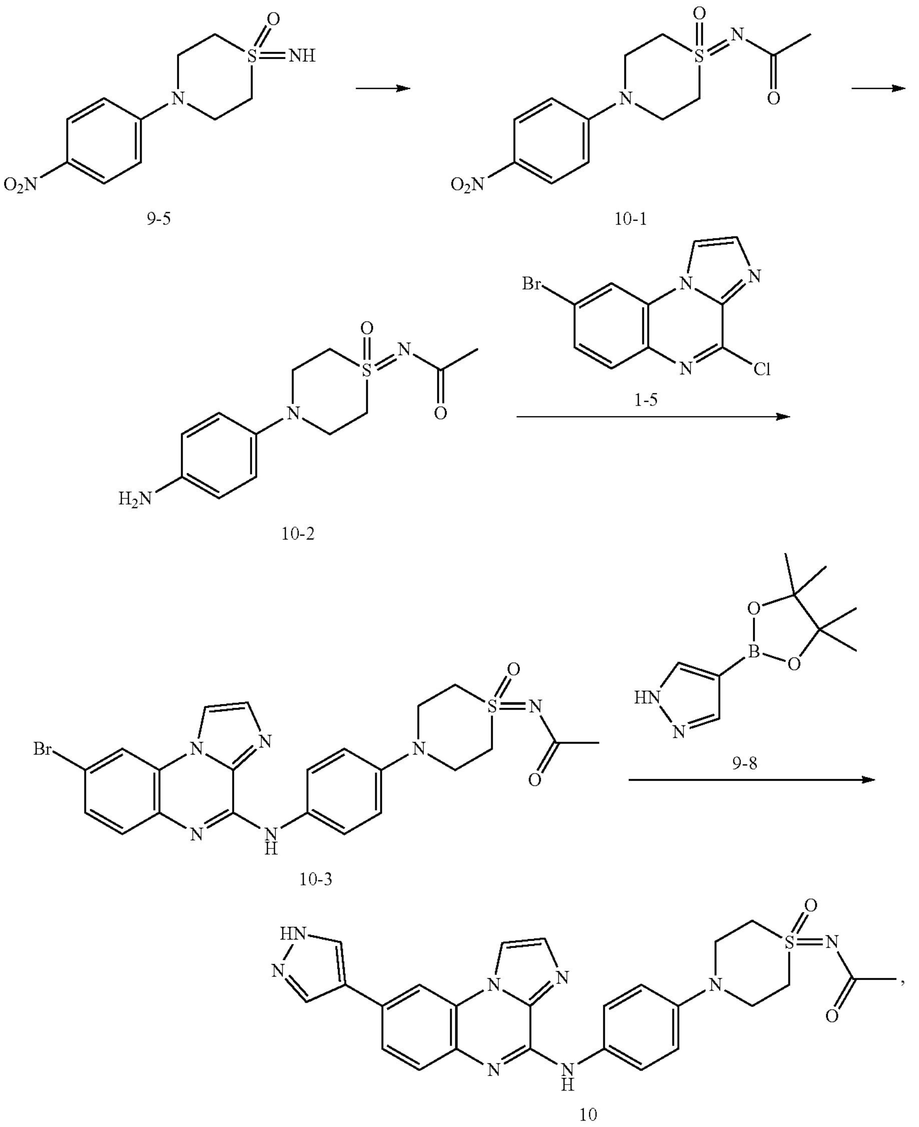

9-5 10-1 1-5 10-2 9-8 10-3 10 step 1 of synthesizing a compound of formula 10-1 from a compound of formula 9-5;

step 2 of synthesizing a compound of formula 10-2 from the compound of formula 10-1;

step 3 of synthesizing a compound of formula 10-3 by reacting the compound of formula 10-2 with a compound of formula 1-5; and step 4 of synthesizing the compound of formula 10 by reacting the compound of formula 10-3 with a compound of formula 9-8.

34. The method according to claim 33, wherein:

step 1 comprises adding triethylamine and acetyl chloride to a solution of the compound of formula 9-5 in dichloromethane, stirring the reaction solution at 25 degrees Celsius for 2 hours, adding water to the reaction solution, extracting the mixture three times with dichloromethane, and combining, washing twice with saturated brine, drying over anhydrous sodium sulfate, filtering and concentrating the organic phases from the extraction to obtain the compound of formula 10-1;

step 2 comprises adding ammonium chloride and iron powder to a solution of the compound of formula 10-1 in ethanol and water under the protection of nitrogen, stirring the reaction solution at 90 degrees Celsius 1 hour, then filtering the reaction solution, adding water to the filtrate, extracting the mixture three times with ethyl acetate, and combining, drying, filtering and concentrating the organic phases from the extraction to obtain the compound of formula 10-2;

step 3 comprises adding the compound of formula 10-2 and DIEA to a solution of the compound of formula 1-5 in dimethyl sulfoxide, stirring the reaction solution at 120 degrees Celsius for 16 hours, then cooling the reaction solution to room temperature, adding water to precipitate a solid, filtering the mixture, slurrying the filter cake from the filtering with isopropanol, and filtering and drying the slurry to obtain the compound of formula 10-3; and step 4 comprises adding the compound of formula 10-3, the compound of formula 9-8, potassium carbonate and Pd(dppf)$Cl_2$ to 1,4-dioxane and water, then stirring the reaction solution at 100° C. for 16 hours under the protection of nitrogen, adding water to the reaction solution, extracting the solution three times with dichloromethane, combining, washing twice with saturated brine, drying over anhydrous sodium sulfate, filtering and concentrating the organic phases from the extraction to obtain a crude product, and separating and purifying the crude product by silica gel column chromatography to obtain the compound of formula 10.

35. A method for preparing a compound of formula 11, comprising:

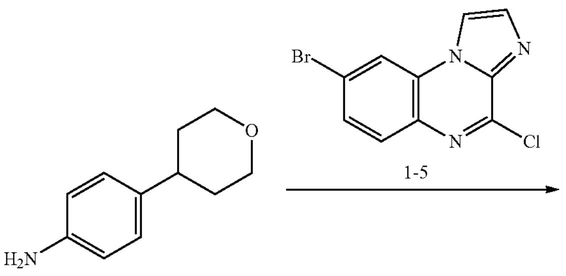

11-1

1-5

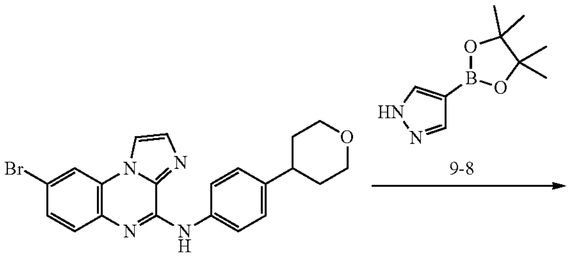

11-2

9-8

-continued

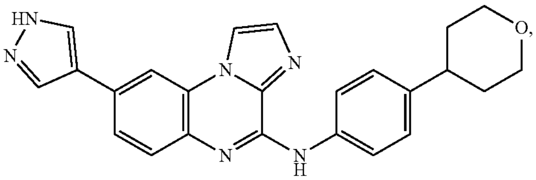

11 step 1 of synthesizing a compound of formula 11-2 by reacting the compound of formula 11-1 with a compound of formula 1-5; and step 2 of synthesizing the compound of formula 11 by reacting the compound of formula 11-2 with a compound of formula 9-8.

36. The method according to claim 35, wherein:

step 1 comprises mixing the compound of formula 1-5 and the compound of formula 11-1 and stirring the mixture at 120 degrees Celsius for 16 hours under the protection of nitrogen, cooling the reaction solution to room temperature, adding dichloromethane and methanol and stirring the mixture for 15 minutes, filtering the mixture, collecting and drying the filter cake from the filtering under vacuum to obtain the compound of formula 11-2; and step 2 comprises adding the compound of formula 11-2, the compound of formula 9-8, potassium carbonate and Pd(dppf)$Cl_2$ to 1,4-dioxane and water, then stirring the reaction solution at 100° C. for 16 hours under the protection of nitrogen, adding water to the reaction solution, extracting the solution three times with dichloromethane, combining, washing twice with saturated brine, drying over anhydrous sodium sulfate, filtering and concentrating the organic phases from the extraction to obtain a crude product, and separating and purifying the crude product by silica gel column chromatography to obtain the compound of formula 11.

37. A method for preparing a compound of formula 12, comprising:

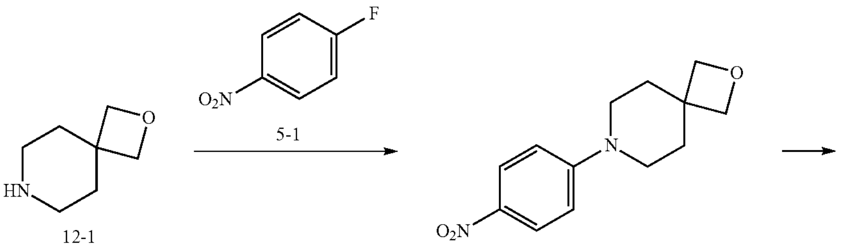

12-1

5-1

12-2

-continued

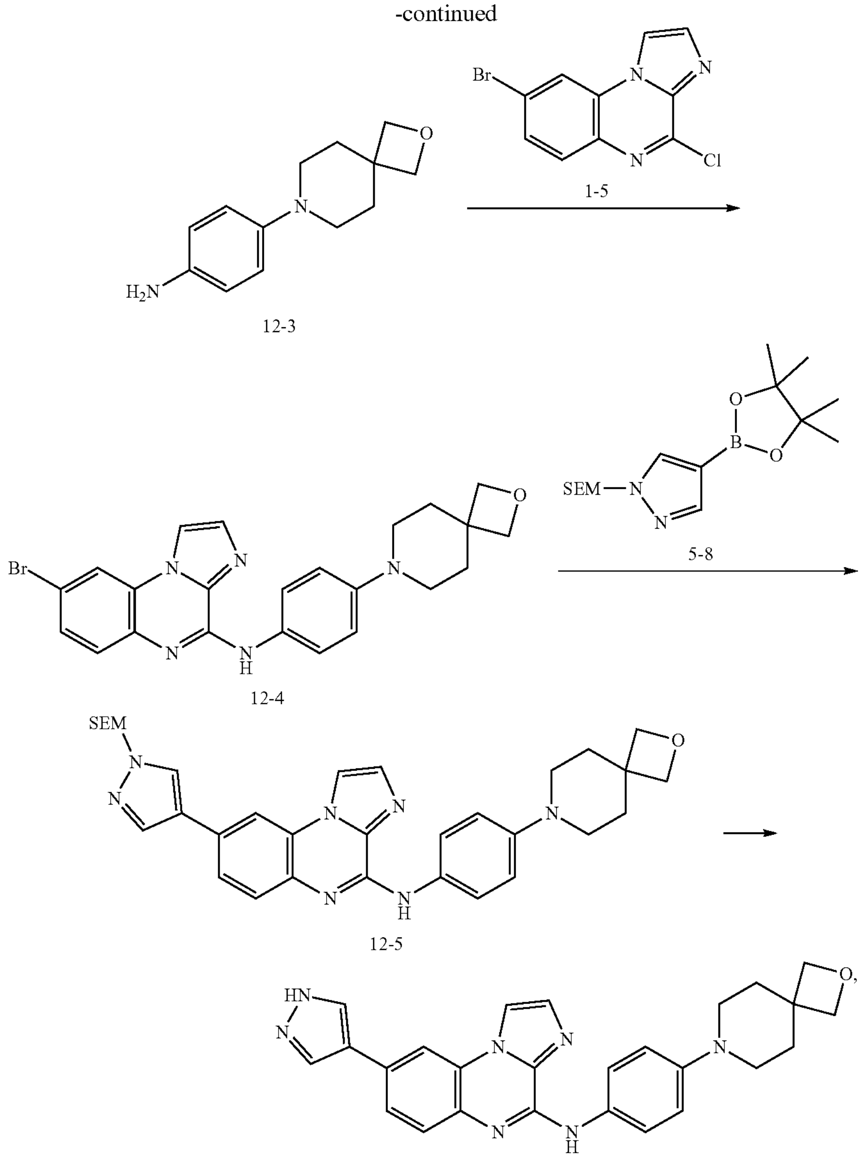

1-5

12-3

5-8

12-4

12-5

12 step 1 of synthesizing a compound of formula 12-2 by reacting a compound of formula 12-1 with a compound of formula 5-1;

step 2 of synthesizing a compound of formula 12-3 from the compound of formula 12-2;

step 3 of synthesizing a compound of formula 12-4 by reacting the compound of formula 12-3 with a compound of formula 1-5;

step 4 of synthesizing a compound of formula 12-5 by reacting the compound of formula 12-4 with a compound of formula 5-8; and step 5 of synthesizing the compound of formula 12 from the compound of formula 12-5.

38. The method according to claim 37, wherein:

step 1 comprises adding potassium carbonate and the compound of formula 12-1 to a solution of the compound of formula 5-1 in DMSO, stirring the reaction solution at 100 degrees Celsius for 16 hours, concentrating the reaction solution, adding water, and extracting the mixture three times with ethyl acetate, and combining, drying, filtering and concentrating the organic phases from the extraction to obtain the compound of formula 12-2;

step 2 comprises adding ammonium chloride and iron powder to a solution of the compound of formula 12-2 in ethanol and water under the protection of nitrogen, stirring the reaction solution at 100 degrees Celsius for 16 hours, then filtering the reaction solution, adding water to the filtrate, extracting the mixture three times with ethyl acetate, and combining, drying, filtering and concentrating the organic phases from the extraction to obtain the compound of formula 12-3;

step 3 comprises adding the compound of formula 12-3 and DIEA to a solution of the compound of formula 1-5 in isopropanol, stirring the reaction solution at 120 degrees Celsius for 16 hours, then cooling the reaction solution to room temperature, adding water, extracting the solution three times with ethyl acetate, and combining, drying, filtering and concentrating the organic phases from the extraction to obtain the compound of formula 12-4;

step 4 comprises adding the compound of formula 12-4, the compound of formula 5-8, potassium carbonate and Pd(dppf)$Cl_2$ to 1,4-dioxane and water, then stirring the reaction solution at 100° C. for 16 hours under the protection of nitrogen, adding water to the reaction solution, extracting the solution three times with dichloromethane, combining, washing twice with saturated brine, drying over anhydrous sodium sulfate, filtering and concentrating the organic phases from the extraction to obtain a crude product, and separating the crude product by silica gel column chromatography to obtain the compound of formula 12-5; and step 5 comprises adding the compound of formula 12-5 to dioxane hydrochloride, stirring the reaction solution at 25 degrees Celsius for 16 hours, then adjusting the pH of the reaction solution to 8 with aqueous sodium hydroxide solution, adding water, extracting the solution twice with dichloromethane, and then combining, washing twice with saturated brine, drying over anhydrous sodium sulfate, filtering and concentrating the organic phases to obtain the compound of formula 12.

39. A method of inhibiting spleen tyrosine kinase (Syk) and vascular endothelial growth factor 2 in a subject, comprising administering a therapeutically effective amount of the compound or pharmaceutically acceptable salt thereof according to claim 1 to the subject in need thereof.

40. A method of treating a disease selected from the group consisting of dry eye, allergic conjunctivitis, age-related macular degeneration, proliferative diabetic retinopathy and retinopathy of prematurity, the method comprising administering a therapeutically effective amount of the compound or pharmaceutically acceptable salt thereof according to claim 1 to the subject in need thereof.

* * * * *